US009226885B2

(12) United States Patent
Ott

(10) Patent No.: US 9,226,885 B2
(45) Date of Patent: *Jan. 5, 2016

(54) PERSONAL CARE AND MEDICINAL PRODUCTS INCORPORATING BOUND ORGANOSULFUR GROUPS

(75) Inventor: David M. Ott, Oakland, CA (US)

(73) Assignee: Allium Vitalis Incorporated, Berkeley, CA (US)

( * ) Notice: Subject to any disclaimer, the term of this patent is extended or adjusted under 35 U.S.C. 154(b) by 1017 days.

This patent is subject to a terminal disclaimer.

(21) Appl. No.: 11/441,292

(22) Filed: May 24, 2006

(65) Prior Publication Data

US 2006/0269488 A1 Nov. 30, 2006

Related U.S. Application Data

(60) Provisional application No. 60/684,357, filed on May 24, 2005.

(51) Int. Cl.
*A61Q 17/04* (2006.01)
*A61Q 19/00* (2006.01)
*A61P 17/00* (2006.01)
*A61K 8/46* (2006.01)
*A61K 47/20* (2006.01)
*A61K 8/97* (2006.01)
*A61Q 11/00* (2006.01)
*A61K 9/00* (2006.01)

(52) U.S. Cl.
CPC ... *A61K 8/46* (2013.01); *A61K 8/97* (2013.01); *A61K 47/20* (2013.01); *A61Q 11/00* (2013.01); *A61Q 17/04* (2013.01); *A61K 9/0014* (2013.01); *A61K 2800/522* (2013.01)

(58) Field of Classification Search
CPC . A61K 9/0014; A61K 2300/00; A61K 47/20; A61K 8/46; A61K 2800/522; A61Q 17/04
USPC ........................................ 424/59, 401, 705
See application file for complete search history.

(56) References Cited

U.S. PATENT DOCUMENTS

| 2,432,797 | A | 12/1947 | Peters et al. |
| 4,486,403 | A | 12/1984 | Mechanic et al. |
| 5,296,500 | A | 3/1994 | Hillebrand |
| 5,451,412 | A | 9/1995 | Bounous et al. |
| 5,906,811 | A | 5/1999 | Hersh |
| 6,200,570 | B1 * | 3/2001 | Diwan et al. ............ 424/195.18 |
| 6,613,230 | B2 * | 9/2003 | Krulik et al. ................... 210/638 |
| 2002/0082279 | A1 * | 6/2002 | Schultz ........................ 514/330 |
| 2003/0077264 | A1 * | 4/2003 | Goodrich ................... 424/93.72 |
| 2004/0091506 | A1 * | 5/2004 | Bommarito ................... 424/400 |
| 2005/0147572 | A1 * | 7/2005 | Giacomoni et al. ............ 424/59 |

FOREIGN PATENT DOCUMENTS

| CA | 213170 | * | 3/1996 |
| KR | 2005036076 | * | 10/2003 |
| WO | WO 02/089826 | * | 11/2002 |

OTHER PUBLICATIONS

Rubaiul et al., BMJ "Clinicians' role in management of arsenicosis in Bangladesh: interview study", 328, pp. 493-494, Feb. 2004.*
Dwivedi et al., Anticancer Drugs, vol. 9, Iss. 3, Mar. 1998, Abstract).*
Yannai, S, ed., Dictionary of Food Coumpounds with CD-ROM: Actives, Flavors, and Ingredients, Chapman & Hall/CRC, p. 3, 2004.*
Amagase et al., Jounal of Nutrition, Intake of Garlic and Its Bioactive Components, pp. 955S to 962S, 2001.*
Kim et al. Antimicrobial Activity of Alk(en)yl Sulfides Found in Essential Oils of Garlic and Onion. Mar. 26, 2004. Food Sci. Biotechnology vol. 13. pp. 235-239.*
Bergner, Paul. The Healing Power of Garlic. 1996. Prima Publishing.*
Thompson, David. Insect Bite. 2003.*
Tisserand et al. Essential Oil Safety: A Guide for Health Care Professionals. (2014). Churchill Livingstone Elsevier. p. 369.*
Thomas et al., "Oxidation of chloride and thiocyanate by isolated leukocytes", J Biol Chem. Jul. 25, 1986;261(21):9694-702.
Kala et al., "The MRP2/cMOAT transporter and arsenic-glutathione complex formation are required for biliary excretion of arsenic", J Biol Chem. Oct. 27, 2000;275(43):33404-8.
Orringer et al., "An ascorbate-mediated transmembrane-reducing system of the human erythrocyte", J Clin Invest. Jan. 1979;63(1):53-8.
Mazumder, "Chronic Arsenic Toxicity: Clinical Features, Epidemiology, and Treatment: Experience in West Bengal", Journal of Environmental Science and Health 38:141.
Wierzbicka et al., "Glutathione in Food", Journal of Food Composition and Analysis 2:327.
Kyung et al., "Antimicrobial activity of sulfur compounds derived from cabbage", J Food Prot. Jan. 1997;60(1):67-71.
Barnhart et al., "Concentration-dependent antioxidant activity of probucol in low density lipoproteins in vitro . . . ", J Lipid Res. Nov. 1989;30(11):1703-10.
Friedman et al., "Nutritional improvement of soy flour", J Nutr. Dec. 1984;114(12):2241-6.
Lau, "Suppression of LDL oxidation by garlic", J Nutr. Mar. 2001;131(3s):985S-8S.
Borec, "Antioxidant health effects of aged garlic extract", J Nutr. Mar. 2001;131(3s):1010S-5S.
Lamm et al., "Enhanced immunocompetence by garlic: role in bladder cancer and other malignancies", J Nutr. Mar. 2001;131(3s):1067S-70S.
Hoshino et al., "Effects of garlic preparations on the gastrointestinal mucosa", J Nutr. Mar. 2001;131(3s):1109S.

(Continued)

*Primary Examiner* — Frederick Krass
*Assistant Examiner* — Tracy Liu

(57) ABSTRACT

Personal care products useful for the maintenance of personal appearance and good health and minor treatments that do not require professional health care, as well as products that provide a combination of anti-microbial, anti-oxidant, anti-inflammatory, and anti-aging properties and are suitable for use without a prescription. The products utilize a biomembrane permeable organosulfur compound that can redox cycle between thiol, disulfide, and thiosulfinate forms in response to oxidants and antioxidants inside and outside of cells. Example products include an anti-microbial toothpaste with anti-plaque properties, an anti-inflammatory skin lotion with antioxidant, antimicrobial, and deodorant properties, and an anti-toxin skin lotion with anti-arsenicosis properties.

11 Claims, 5 Drawing Sheets

(56) References Cited

OTHER PUBLICATIONS

Keiss et al., "Garlic modulates cytokine expression in lipopolysaccharide-activated human blood thereby inhibiting NF-kappaB activity", J Nutr. Jul. 2003;133(7):2171.
Blair et al., "Oral L-2-oxo-4-thiazolidine reduces bacterial translocation after radiation in the Fischer rat", J Surg Res. Oct. 1996;65(2):165.
Chowdhury et al., "Flurbiprofen, a unique non-steroidal anti-inflammatory drug with antimicrobial activity against Trichophyton . . . ", Lett Appl Microbiol. 2003;37(2):158.
Prasad et al., "Antioxidant activity of allicin, an active principle in garlic", Mol Cell Biochem. Jul. 19, 1995;148(2):183.
Miron et al., "Inhibition of tumor growth by a novel approach: in situ allicin generation using targeted alliinase delivery", Mol Cancer Ther. Dec. 2003;2(12):1295.
Ankri et al., "Antimicrobial properties of allicin from garlic", Microbes Infect. Feb. 1999;1(2):125.
Liu et al., "Overexpression of glutathione S-transferase II and multidrug resistance transport proteins is associated with acquired . . . ", Mol Pharmacol. Aug. 2001;60(2):302.
Hamm et al., "Changes in the Sulphydryl and Disulfide Groups in Beef Muscle Proteins During Heating", Nature 1965;207:1269.
Mathews et al., "Inhibition of NF-kappaB DNA binding by nitric oxide", Nucleic Acids Res. Jun. 15, 1996;24(12):2236.
Munday et al., "Low doses of diallyl disulfide, a compound derived from garlic, increase tissue activities of quinone reductase . . . ", Nutr Cancer. 1999;34(1):42.
Elnima et al., "The antimicrobial activity of garlic and onion extracts", Pharmazie. Nov. 1983;38(11):747.
Nakagawa et al., "Prevention of Liver Damage by Aged Garlic Extract and Its Components in Mice", Phytotherapy Research 1989;3:50.
Banerjee et al., "Garlic as an antioxidant: the good, the bad and the ugly", Phytother Res. Feb. 2003;17(2):97.
Mukherjee et al., "Prevention of bone loss by oil extract of garlic (*Allium sativum* Linn.) in an ovariectomized rat model of osteoporosis" Phytother Res. May 2004;18(5):389.
Jung et al., "Effect of Different Garlic Preparations on the Fluidity of Blood, Fibrinolytic Activity, and Peripheral Microcirculation . . . ", Planta Med. 1990;56:668.
Lawson et al., "Pre-Hepatic Fate of Organosulfur Compounds Derived from Garlic (*Allium sativum*)", Planta Med. 1993;59:A688.
Imai et al., "Antioxidant and Radical Scavenging Effects of Aged Garlic Extract and its Constituents", Planta Med. 1994;60:417.
Lawson et al., "Allicin Release under Simulated Gastrointestinal Conditions from Garlic Powder Tablets Employed in Clinical Trials . . . ", Planta Med. 2001;67:13.
Liu et al., "Induction of oxyradicals by arsenic: implication for mechanism of genotoxicity", Proc Natl Acad Sci U S A. Feb. 13, 2001;98(4):1643.
Delhalle et al., "A Beginner's Guide to NF-kB Signalling Pathways", Ann N Y Acad Sci. Dec. 2004;1030:1.
Singh et al., "Thiol-disulfide interchange", in "Supplement S—The Chemistry of Sulphur-containing Functional Groups", 1993; John Wiley $ Sons, New York, NY.
Wardman, "Thiyl Radicals in Biology: Their Role as a 'Molecular Switch' Central to Cellular Oxidative Stress", in "S-Centered Radicals", 1999; John Wiley & Sons, New York, NY.
National Research Council, "Chemistry of Arsenic", in "Arsenic", 1977; National Academy of Sciences, Washington D.C.
National Research Council, "Biologic Effects of Arsenic on Plants and Animals", in "Arsenic", 1977; National Academy of Sciences, Washington D.C.
Newstrom, "Cysteine" in "Nutrients Catalog", 1993; McFarland & Company, Jefferson NC.
Miranda et al., "The Chemical Biology of Nitric Oxide in Nitric Oxide—Biology and Pathology" 2000; Academic Press, New York NY.

Huie et al., "Chemistry of Reactive Oxygen Species" in "Reactive Oxygen Species in Biological Systems: An Interdisciplinary Approach", 1999; Kluwer Academic, New York NY.
Gordon, "alpha-Lactalbumin", in "Milk Proteins—Chemistry and Molecular Biology", 1971; Academic Press New York NY.
Petsko et al., "Control by pH and Redox Environment", in "Protein Structure and Function", 2004; New Scince Press Ltd., London UK.
Schrimshaw, "Nutritional Significance of Protein Quality: A Global View", in "Protein Quality in Humans: Assessment and in Vitro Estimation", AVI Publishing, Westport CT.
Brassini et al., "A Short-Term Proceedure to Evaluate Protein Quality . . . ", in "Protein Quality in Humans: Assessment and in Vitro Estimation", AVI Publishing, Westport CT.
Friedman, "The Formation of Disulfide Bonds in the Synthesis of Secretory Proteins . . . ", in "Glutathione Metabolism and Physiological Functions", 1990; CRC Press, Boca Raton FL.
Creighton, "Pathways and Energetics of Protein Disulfide Formation" in "Functions of Glutathione", 1983; Raven Press, New York NY.
Tateishi et al., "Regulation of Glutathione Level in Primary Cultured Hepatocytes", in "Glutathione Centennial" 1989; Academic Press, New York NY.
Gilbert, "Thermodynamic and Kinetic Constraints on Thiol/Disulfide Exchange . . . ", in "Glutathione Centennial" 1989; Academic Press, New York NY.
Bannai et al., "Regulation of Glutathione Level by Amino Acid Transport", in "Glutathione Centennial" 1989; Academic Press, New York NY.
Kim, "Intestinal Mucosal Hydrolysis of Proteins and Peptides" in "Peptide Transport and Hydrolysis—Ciba Foundation Symposium 50", 1977;Elsiver, New York NY.
Weisger et al., "S-Methylation: Thiol S-Methyltransferase", in "Enzymatic Basis of Detoxification, vol. II", 1980; Academic Press, New York NY.
Webb, "Arsenicals" in "Enzyme and Metabolic Inhibitors, vol. 3", 1966; Academic Press, New York NY.
Ishikawa et al., "Transport of Glutathione S-Conjugates from Cancer Cells", in "Glutathione S-Transferases", 1996; Taylor & Frences Ltd., London UK.
Packer et al., "Vitamin E: An Introduction", in "The Antioxidant Vitamins C and E", 2002; AOCS Press, Champaign IL.
Calvin, "Mercaptans and Disulfides: Some Physics, Chemistry, and Speculation" in "Glutatione" 1954; Academic Press, New York NY.
Sarwar et al., "Influence of Feeding Alkaline/Heat Processed Proteins . . . , in Nutraceuticals: Designer Foods III" 1997; Food & Nutritions Press, Trumbull CT.
Ghur et al., "Role of Phytochemicals in Chronic Disease Prevention, in Nutraceuticals: Designer Foods III" 1997; Food & Nutritions Press, Trumbull CT.
Meharg, "JOI Bangla!" in "Venomous Earth—How Arsenic Caused the World's Worst Mass Poisoning" 2005; Macmillan, New York NY.
National Research Council, "Disposition of Inorganic Arsenic", in "Arsenic in Drinking Water", National Academy Press, Washington DC.
National Research Council, "Biomarkers of Arsenic Exposure", in "Arsenic in Drinking Water", National Academy Press, Washington DC.
Inoue et al., "Biochemical and Clinical Aspects of Extracellular Glutathione and Related Thiols", in "Biothions in Health and Disease", 1995; Marcel Dekker, Inc. New York NY.
Siems et al., "Oxidative Breakdown of Carotenoids and Biological Effects of their Metabolites" in "Handbook of Antioxidants", 2002; Marcel Dekker, Inc, New York NY.
Meister, "The Antioxidant Effects of Glutathone and Ascorbic Acid", in "Oxidative Stress, Cell Activation and Viral Infection", 1994; Birkhauser Verlag, Basel Switzerland.
Droge et al., "Abnormal Redox Regulation in HIV Infection . . . ", in "Oxidative Stress, Cell Activation and Viral Infection", 1994; Birkhauser Verlag, Basel Switzerland.
Lawson et al. "Antioxidant Effects" in "GARLIC the Science and Threapeutic Application of Allium sativum . . . ", 1996; Williams & Wilkins Baltimore MD.

(56) References Cited

OTHER PUBLICATIONS

Alexander et al., "Mode of Action of Some Substances Which Protect against the Lethal Effects of X-Rays", Radiation Research 2:392.
Barron, Enzyme Systems Containing Active Sulphydryl Groups. The Role of Glutathione, Science 97:356.
Zakharyan et al., "Arsenite methylation by methylvitamin B12 and glutathione does not require an enzyme", Toxicol Appl Pharmacol. Feb. 1, 1999;154(3):287.
Brambila et al., "Chronic arsenic-exposed human prostate epithelial cells exhibit stable arsenic tolerance", Toxicol Appl Pharmacol. Sep. 1, 2002;183(2):99.
Chen et al., "Biomarkers of exposure, effect, and susceptibility of arsenic-induced health hazards in Taiwan", Toxicol Appl Pharmacol. Aug. 7, 2005;206(2):198.
Vahter et al., "Effects of low dietary intake of methionine, choline or proteins on the biotransformation of arsenite in the rabbit", Toxicol Lett. Jun. 1987;37(1):41.
White etal., "Toxicity evaluations of L-cysteine and Procysteine, a cysteine prodrug, given once intravenously to neonatal rats", Toxicol Lett. Jul. 1993;69(1):15.
Huang et al., "Glutathione as a cellular defence against arsenite toxicity in cultured Chinese hamster ovary cells", Toxicology. May 24, 1993;79(3):195.
Schuliga et al., "Upregulation of glutathione-related genes and enzyme activities in cultured human cells by sublethal concentrations of . . .", Toxicol Sci. Dec. 2002;70(2):183.
Kojima et al., "Chronic exposure to methylated arsenicals stimulates arsenic excretion pathways and induces arsenic tolerance in rat liver cells", Toxicol Sci. 2006;91(1):70.
Molins, Irradiation of Meats and Poultry, in "Food Irradiation: Principles and Applications", 2001; Wiley Interscience, New York NY.
Deihl, Radiolytic Effects in Foods in "Preservation of Food by Ionizing Radiation, vol. 1", 1982; CRC Press Inc. Boca Raton FL.
Ludescher, "Physical and Chemical Properties of Amino Acids and Proteins", in "Food Proteins: Properties and Characterization", 1996; VHC Publishers, New York NY.
Freidman, "Nutrition" in "Food Proteins: Properties and Characterization", 1996; VHC Publishers, New York NY.
Feldberg et al., "In vitro mechanism of inhibition of bacterial cell growth by allicin", Antimicrob Agents Chemother. Dec. 1988;32(12):1763-8.
Tada et al., "Nematicidal and Antimicrobial Constituents from *Allium grayi* Regal and *Allium fistulosum* L. var. caespitosum", Agric Biol Chem. 1988;52(9):2383-5.
Droge, "Oxidative stress and aging", Adv Exp Med Biol. 2003;543:191-200.
Johnson et al., "Treatment of seborrheic dermatitis", Am Fam Physician. May 1, 2000;61(9):2703-10, 2713-4.
Josling, "Preventing the common cold with a garlic supplement: a double-blind, placebo-controlled survey", Adv Ther. Jul.-Aug. 2001;18(4):189-93.
Di Buono et al., "Total sulfur amino acid requirement in young men as determined by indicator amino acid oxidation with L-[1-13C]phenylalanine", Am J Clin Nutr. 2001;74(6):756.
Elkayam et al., "The effects of allicin and enalapril in fructose-induced hyperinsulinemic hyperlipidemic hypertensive rats", Am J Hypertens. Apr. 2001;14(4 Pt 1):377-81.
Elkayam et al., "The effects of allicin on weight in fructose-induced hyperinsulinemic, hyperlipidemic, hypertensive rats", Am J Hypertens. Dec. 2003;16(12):1053-6.
Johnson et al., "Death of *Salmonella typhimurium* and *Escherichia coli* in the presence of freshly reconstituted dehydrated garlic and onion", Appl Microbiol. Jun. 1969;17(6):903.
"Taurine—Monograph", Altern Med Rev. 2001;6(1):78-82.
Bakri et al., "Inhibitory effect of garlic extract on oral bacteria", Arch Oral Biol. Jul. 2005;50(7):645-51.
Khan et al., "Magnitude of arsenic toxicity in tube-well drinking water in Bangladesh and its adverse effects on human health . . . ", Asian Pac J Cancer Prev. 2003;4(1):7-14.

Meister et al., "Glutathione", Annu Rev Biochem. 1983;52:711-60.
Greipp, "Hyperpigmentation syndromes (diffuse hypermelanosis)", Arch Intern Med. Mar. 1978;138(3):356-7.
Droge et al., "The plasma redox state and ageing", Ageing Res Rev. Apr. 2002;1(2):257-78.
Chen et al., "Atherogenicity and carcinogenicity of high-arsenic artesian well water", Arteriosclerosis. Sep.-Oct. 1988;8(5):452-60.
Ochi, "Arsenic compound-induced increases in glutathione levels in cultured Chinese hamster V79 cells . . . ", Arch Toxicol. 1997;71(12):730-40.
Hayakawa et al., "A new metabolic pathway of arsenite: arsenic-glutathione complexes are substrates for human arsenic methyltransferase Cyt19", Arch Toxicol. 2005;79(4):183-91.
Bremer et al., "Enzymic methylation of forign sulfhydryl compounds", Biochem Biophys Acta 1961;46:217-224.
Pisciotto et al., "Induction of mucosal glutathione synthesis by arsenic", Biochim Biophys Acta. Mar. 3, 1980;628(2):241-3.
Napolitano et al., "2-Aryl-1,3-thiazolidines as masked sulfhydryl agents for inhibition of melanogenesis", Biochim Biophys Acta. Mar. 4, 1991;1073(2):416-22.
Rabinkov et al., "The mode of action of allicin: trapping of radicals and interaction with thiol containing proteins", Biochim Biophys Acta. Feb. 2, 1998;1379(2):233-44.
Miron et al., "The mode of action of allicin: its ready permeability through phospholipid membranes may contribute to its biological activity", Biochim Biophys Acta. Jan. 2000.
Seo et al., "Antibacterial activity of S-methyl methanethiosulfinate and S-methyl 2-propene-1-thiosulfinate from Chinese chive . . . ", Biosci Biotechnol Biochem. 2001;65(4):966-8.
Cotgreave et al., "Recent trends in glutathione biochemistry—glutathione-protein interactions", Biochem Biophys Res Commun. Jan. 6, 1998;242(1):1-9.
Lammon et al., "Effects of protein deficient diets on the developmental toxicity of inorganic arsenic in mice", Birth Defects Res B Dev Reprod Toxicol. Jun. 2004;71(3):124-34.
Saxena et al., "Formation of three-dimensional structure in proteins. I. Rapid nonenzymic reactivation of reduced lysozyme", Biochemistry. Dec. 8, 1970;9(25):5015-23.
Marshall et al., "Inhibition of NF-kappa B by S-nitrosylation", Biochemistry. Feb. 13, 2001;40(6):1688-93.
Wills, "Enzyme inhibition by allicin, the active principle of garlic", Biochemical Journal 1956;63:514-20.
Tosti et al., "Calcipotriol ointment in nail psoriasis: a controlled double-blind comparison with betamethasone dipropionate and salicylic acid", Br J Dermatol. Oct. 1998;139(4.
Dai et al., "Malignant cells can be sensitized to undergo growth inhibition and apoptosis by arsenic trioxide through modulation of the glutathione . . . ", Blood. 1999;93:268-77.
Sordet et al., "Mitochondria-targeting drugs arsenic trioxide and lonidamine bypass the resistance of TPA-differentiated leukemic cells to apoptosis", Blood. 2001;97:3931-40.
Grad et al., "Ascorbic acid enhances arsenic trioxide-induced cytotoxicity in multiple myeloma cells", Blood. Aug. 1, 2001;98(3):805-13.
Gyamlani et al., "Acetaminophen toxicity: suicidal vs. accidental", Crit Care. Apr. 2002;6(2):155-9.
Das et al., "Nitric oxide synthase is a unique mechanism of garlic action" Biochemical Society Transactions 1995;23:S136.
Smith et al., "Contamination of drinking-water by arsenic in Bangladesh: a public health emergency", Bull World Health Organ. 2000;78(9):1093-103.
Herrmann et al., "Disturbed homocysteine and methionine cycle intermediates S-adenosylhomocysteine and S-adenosylmethionine . . . ", Clin Chem. May 2005;51(5):891-7.
Hu et al., "Arsenic trioxide induces apoptosis in cells of MOLT-4 and its daunorubicin-resistant cell line via depletion of . . . ", Cancer Chemother Pharmacol. 2003;52(1):47-58.
Bahlis et al., "Feasibility and correlates of arsenic trioxide combined with ascorbic acid-mediated depletion of intracellular . . . ", Clin Cancer Res. Dec. 2002;8(12):3658-68.
Neuhouser et al., "Fruits and vegetables are associated with lower lung cancer risk only in the placebo arm of the . . . ", Cancer Epidemiol Biomarkers Prev. Apr. 2003;12(4):350-8.

(56) References Cited

OTHER PUBLICATIONS

Sparins et al., "Effects of organosulfur compounds from garlic and onions on benzo[a]pyrene-induced neoplasia and . . . ", Carcinogenesis. Jan. 1988;9(1):131-4.
Shirin et al., "Antiproliferative effects of S-allylmercaptocysteine on colon cancer cells when tested alone or in combination with . . . ", Cancer Res. 2001;61:725-31.
Scott et al., "Reactions of arsenic(III) and arsenic(V) species with glutathione", Chem Res Toxicol. Jan.-Feb. 1993;6(1):102-6.
Styblo et al., "Comparative inhibition of yeast glutathione reductase by arsenicals and arsenothiols", Chem Res Toxicol. Jan. 1997;10(1):27-33.
Teyssier et al. "Metabolism of diallyl disulfide by human liver microsomal cytochromes P-450 and flavin-containing monooxygenases", Drug Metab Dispos. 1999;27(7):835-41.
Delany et al., "The Order of the Day" in the Delany Sisters' Book of Everyday Wisdom, 1994; Kodansha International, New York, NY.
Smith et al., "Arsenic-induced skin lesions among Atacameño people in Northern Chile despite good nutrition and centuries of exposure", Environ Health Perspect. 2000;108:617.
Mitra et al., "Nutritional factors and susceptibility to arsenic-caused skin lesions in West Bengal, India", Environ Health Perspect. Jul. 2004;112(10):1104-9.
Jocelyn, "The standard redox potential of cysteine-cystine from the thiol-disulphide exchange reaction with glutathione and lipoic acid", Eur J Biochem. Oct. 1967;2(3):327-31.
Das et al., "Modification of clastogenicity of three known clastogens by garlic extract in mice in vivo", Environ Mol Mutagen. 1993;21(4):383-8.
Nemes et al., "Bricks and mortar of the epidermal barrier", Exp Mol Med. Mar. 31, 1999;31(1):5-19.
Maiti et al., "Differential response of cellular antioxidant mechanism of liver and kidney to arsenic exposure and its . . . ", Environ Toxicol Pharmacol. 2000;8(4):227-235.
Stoewsand et al., "Bioactive organosulfur phytochemicals in Brassica oleracea vegetables—a review", Food Chem Toxicol. Jun. 1995;33(6):537-43.
Focke et al., "Allicin, a naturally occurring antibiotic from garlic, specifically inhibits acetyl-CoA synthetase", FEBS Lett. Feb. 12, 1990;261(1):106-8.
Shashikanth et al., "A comparative study of raw garlic extract and tetracycline on caecal microflora and serum proteins of albino rats", Folia Microbiol (Praha). 1984;29(4):34.
Mendiratta et al., "Erythrocyte ascorbate recycling: antioxidant effects in blood", Free Radic Biol Med. Mar. 15, 1998;24(5):789-97.
Nakahara et al., "Biochemical properties of human oral polymorphonuclear leukocytes", Free Radic Res. May 1998;28(5):485-95.
Shannon et al., "Arsenic-induced skin toxicity", Hum Toxicol. Mar. 1989;8(2):99-104.
Thomas et al., Antibacterial activity of hydrogen peroxide and the lactoperoxidase-hydrogen peroxide-thiocyanate system against oral *streptococci*, Infect Immun. 1994;62:259.
Dehghani et al., "Healing effect of garlic extract on warts and corns", Int J Dermatol. Jul. 2005;44(7):612-5.
Sharma et-al., "Antibacterial property of *Allium sativum* Linn.: in vivo & in vitro studies", Indian J Exp Biol. Jun. 1977;15(6):466-8.
Augusti, "Therapeutic values of onion (*Allium cepa* L.) and garlic (*Allium sativum* L.)", Indian J Exp Biol. Jul. 1996;34(7):634-40.
Mazumder et al., "Arsenic levels in drinking water and the prevalence of skin lesions in West Bengal, India", Int J Epidemiol 1998:27;871-877.
Fuchin et al., "Medical Diseases" in Garlic & Green Onion as Medicine, 1998; Pelanduk Publications, Malaysia.
Cavallito et al., "Allicin the Antibacterial Principle of Allium sativum. I. Isolation, Physical Properties and Antibacterial Action", JACS 1944;66:1950-1.
Cavallito et al., "Allicin the Antibacterial Principle of Allium sativum. II. Determination of the Chemical Structure", JACS 1944;66:1952-4.
Small et al., "Alkyl Thiosulfinates", JACS 1947;69:1710-3.
Cao et al., "Antioxidant capacity of tea and common vegetables", J Agric Food Chem 1996;44:3426-31.
Lawson et al., "Low allicin release from garlic supplements: a major problem due to the sensitivities of alliinase activity", J Agric Food Chem. May 2001;49(5):2592-9.
Xiao et al., "Antioxidant functions of selected allium thiosulfinates and S-alk(en) yl-L-cysteine sulfoxides", J Agric Food Chem. Apr. 24, 2002;50(9):2488-93.
Negishi et al., "Effects of food materials on removal of Allium-specific volatile sulfur compounds", J Agric Food Chem. Jun. 19, 2002;50(13):3856-61.
Lawson et al., "Allicin and allicin-derived garlic compounds increase breath acetone through allyl methyl sulfide . . . ", J Agric Food Chem Mar. 23;53(6):1974-83.

\* cited by examiner

PERSONAL CARE AND MEDICINAL PRODUCTS INCORPORATING BOUND ORGANOSULFUR GROUPS

1. BACKGROUND OF THE INVENTION

1.1 Field of the Invention

The present invention relates generally to products that are useful for personal care: the maintenance of personal appearance and good health, and the minor treatments that do not require professional health care. The present invention also relates to those products that provide a combination of anti-microbial, anti-oxidant, anti-inflammatory, and anti-aging properties and are suitable for use without a prescription. The products utilize a biomembrane permeable organosulfur compound that can redox cycle between thiol, disulfide, and thiosulfinate forms in response to oxidants and antioxidants inside and outside of cells. Example products include an anti-microbial toothpaste with anti-plaque properties, an anti-inflammatory skin lotion with antioxidant, antimicrobial, and deodorant properties, and an anti-toxin skin lotion with anti-arsenicosis properties.

1.2 Brief Introduction to the Invention

The Applicant has previously discovered that there is a class of membrane permeable thiol compounds that can be oxidized in vivo to form membrane permeable disulfides, which can in turn be further oxidized in vivo to form membrane permeable thiosulfinates. The localized oxidation from disulfide to thiosulfinate by activated immune system cells creates a potent anti-microbial agent local to the infectious microbe or cancer cell that is being attacked (US2004/0235946A1). The applicant has further discovered that the cycling between the thiol and disulfide states gives these compounds unique antioxidant and anti-inflammatory properties, including the ability to serve as an extracellular antioxidant that is coupled to the intracellular glutathione reductase system (US2005/0260250A1).

The present invention involves the application of these compounds in products for personal care. It has been discovered that skin care products incorporating these compounds exhibit antimicrobial, anti-inflammatory, UV protective, anti-arsenicosis, and (especially surprisingly) deodorant features while being generally protective of the skin. It has further been discovered that dentifrice products such as toothpaste incorporating these compounds have antimicrobial and anti-plaque properties.

2. DEFINITIONS, ORGANOSULFUR GLOSSARY, AND ABBREVIATIONS

Allicin: Chemical name DiAllylThioSulfinate; chemical formula:

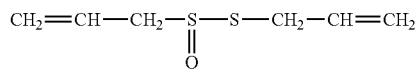

A compound formed by crushing garlic (which allows the enzymatic conversion by alliinase of alliin to allicin) that produces many of the medicinal benefits that are attributed to garlic. For the exposition of the present invention, allicin is used as a model compound representative of a larger class of thiosulfinate compounds set out below. (The other thiosulfinates share the general formula RS(O)SR', with the R and R' groups of the particular compound substituting for the allyl groups of allicin). In general, a compound is referred to herein as a "model" compound when it is representative of a more general class of compounds defined herein.

*Allium*-related compounds: In a historical context, those organosulfur compounds that are either derived from an *allium* (e.g. garlic or onion) through chemical or metabolic means, or are related to such compounds in specific ways such that they can reasonably be expected to exhibit similar medicinal properties.

In the context of the present invention, this term is used to refer to the more general class of compounds containing one or more organosulfur groups that can form, via metabolism or otherwise, membrane permeable small molecular thiols containing 5 or fewer carbon atoms, said thiols being capable of being oxidized in vivo to form membrane permeable disulfides or mixed disulfides, and said disulfides or mixed disulfides being capable of being further oxidized in vivo to form membrane permeable thiosulfinates or mixed thiosulfinates.

In the context of this invention, this term does not include organosulfur amino acids (e.g. cysteine, methionine, homocysteine, cysteamine, or N-acetyl cysteine) or organosulfur peptides (e.g. glutathione) because these are not membrane permeable.

Allyl mercaptan: AllylSH, chemical name AllylThiol; chemical formula:

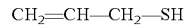

The primary pre-hepatic metabolite of allicin, diallyl disulfide, SAMC, and various other *allium* related compounds containing thioallyl groups. Within a red blood cell (RBC), an allicin molecule will metabolize quickly into two allyl mercaptan molecules. In the present exposition allyl mercaptan is the model thiol compound.

AllylMercapto radical: AllylS*, allyl mercaptan without the terminal hydrogen atom of the SH group, resulting in an unpaired electron on the sulfur atom which is available for covalent bonding to the remainder of a larger molecule. Also called a thioallyl group.

Augment: To make greater, as in size, extent, effect, or quantity.

Biothiol: Any thiol that is commonly found in biological systems. The most common biothiols are cysteine, glutathione, several types of antioxidants (such as lipoic acid), and several types of vitamins (such as thiamine).

Bound: Not volatile. Confined by bonds. In the context of the present invention, a bound organosulfur group can either consist of a radical that is covalently bound to the remainder of a larger molecule, or it can be a small molecule that is non-covalently bound to a larger molecule by forces such as electrostatic forces.

Cysteine: CySH, a sulfur containing amino acid with the formula:

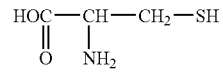

The term cysteine is sometimes used to refer to the sum of cysteine +2 cystine, for example when reporting the total cysteine content of proteins. The term cyst(e)ine is used to refer to any combination of cysteine+cystine. The particular meaning is generally clear from the context.

Cystine: CySSCy, cysteine disulfide. The most common form of oxidized cysteine.

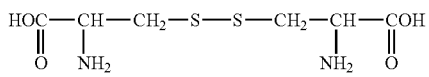

Diallyl Disulfide: DADS, (also abbreviated as AllylSSAllyl or ASSA), the disulfide formed from two AllylMercapto radicals bonded together. Equivalent to deoxygenated allicin. In the present exposition diallyl disulfide is the model disulfide compound.

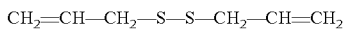

Endogenous: Produced or originating from within a cell or organism.

Free radical: R*, a group of atoms with an unpaired electron. Free radicals are typically very reactive, with a tendency to either steal an electron, to donate an electron, or to covalently bond with another molecule.

Glutathione: A tripeptide composed of the amino acids glutamic acid, cysteine, and glycine. Glutathione is present in biological systems in a variety of forms, the most important of which are reduced glutathione (GSH), the anion of reduced glutathione (GS−), the glutathiyl free radical (GS*), glutathione disulfide (GSSG), mixed glutathione disulfides (GSSR), and protein-glutathione mixed disulfides (PSSG).

The term "glutathione" used by itself usually refers to the sum of GSH and GS−. The term "oxidized glutathione" usually refers to GSSG (the typical end product of oxidation, even though GS* is usually the initial oxidation product). The term "total glutathione" refers to the sum of all of these.

Mercaptan: A small molecule that contains an exposed "SH" group. Mercaptans are thiols that are typically volatile and very smelly.

Mitigate: To make or become less severe or intense.

Oxidation: The removal of an electron (or a hydrogen atom) from an atom or a molecule. Oxidation can also refer to any transformation that tends to occur when something is exposed to reactive oxygen (e.g. the formation of rust), without necessarily specifying the reaction mechanism.

Oxidized: The reaction product that tends to be produced when the reactants are exposed to reactive oxygen, such as the conversion of thiols to disulfides, typically due to the removal of electrons (or hydrogen atoms). For example, if two cysteine molecules together in solution are exposed to oxygen, they tend to eventually form a cysteine disulfide molecule (cystine).

Oxygenated: Another form of oxidation product, where an oxygen atom has been added to a molecule.

Reactive Oxygen Species: ROS, oxygen containing molecules that are capable of producing oxidative damage to other molecules. Many, but not all, ROS are free radicals. Examples include (QP535.O1R43:33):

$H_2O_2$ (hydrogen peroxide), $*O_2^-$ (superoxide radical), *OH (hydroxyl radical), HOCl (hypoclorus acid), $ONOO^-$ (peroxynitrite), $O_2^1$ (singlet oxygen), $O_3$ (ozone), *NO (nitric oxide), and $*NO_2$ (nitrogen dioxide).

Reduced: The converse of oxidized. When a thiyl radical is covalently bonded to a hydrogen atom, it is said to be in its "reduced state". For example, when the terminal sulfur of a cystienal radical is bonded to a hydrogen atom to form a cysteine molecule, it is in its reduced state.

SAA: Sulfur Amino Acids, the sum of cysteine, cystine, and methionine.

SAMC: S-AllylMercaptoCysteine (also shown as AllylSSCy), the molecule formed by a Cysteinyl radical disulfide bonded to an AllylMercapto radical. In the present exposition SAMC is the model mixed disulfide molecule.

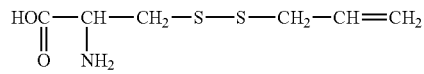

Thiol: RSH, Any molecule that includes one or more terminal sulfhydrate (SH) group.

Volatile: Evaporating readily at normal temperatures and pressures.

3. REFERENCES

For articles contained in books, the first listing (typically by Dewey decimal number or ISBN number) contains identification information for the book and the actual reference(s) are the listings for the article(s) or pages that follow.

AAC32:1763; R. Feldberg et al; In Vitro Mechanism of Inhibition of Bacterial Cell Growth by Allicin; Antimicrobial Agents and Chemotherapy 32:1763.

ABC52:2383; M. Tada et al; Nematicidal and Antimicrobial Constituents from *Allium grayi* Regel and *Allium fistulosum* L. var. *caespiitosum*; Agricultural and Biological Chemistry 52:2383.

AEMB543:191; W. Droge; Oxidative Stress and Aging; Advances in Experimental and Medical Biology 543:191.

AFP61:2703; B. A. Johnson and J. R. Nunley; Treatment of Seborrheic Dermatitis; American Family Physician 61:2703.

AIT18:189; P. Josling; Preventing the Common Cold With a Garlic Supplement: A Double-Blind, Placebo-Controlled Survey; Advances In Therapy 18:189.

AJCN74:756; M. Buono et at; Total Sulfur Amino Acid Requirement in Young Men as Determined by Indicator Amino Acid Oxidation; American Journal of Clinical Nutrition 74:756.

AJH14:377; A. Elkayam et al; The Effects of Allicin and Enapril in Fructose-Induced Hyperinsulinemic Hyperlippidemic Hypertensive Rats; The American Journal of Hypertension 14:377.

AJH16:1053; A. Elkayam et al; The Effects of Allicin on Weight in Fructose-Induced Hyperinsulinemic, Hyperlippidemic, Hypertensive Rats; The American Journal of Hypertension 16:1053.

AM17:903; M. G. Johnson and R. H. Vaughn; Death of *Salmonella typhimurium* and *Escherichia coli* in the Presence of Freshly Reconstituted Dehydrated Garlic and Onion; Applied Microbiology 17:903.

AMR6:78; Taurine; Alternative Medicine Review 6:78.

AOB50:645; I. M. Bakri and C. W. Douglas; Inhibitory effect of garlic extract on oral bacteria; Archives of Oral Biology 50:645.

APJCP4:7; M. Khan et al; Magnitude of Arsenic Toxicity in Tube-well Drinking Water in Bangladesh and Its Adverse Effects on Human Health Including Cancer: Evidence from a Review of the Literature; Asian Pacific Journal of Cancer Prevention 4:7.

ARB52:711; A. Meister and M. Anderson; Glutathione; Annual Review of Biochemistry 52:711.

ARCHIM138:356; P. R. Greipp; Hyperpigmentation Syndromes (Diffuse Hypermelanosis); Archives of Internal Medicine 138:356.

ARR1:257; W. Droge; The Plasma Redox State and Ageing; Ageing Research Reviews 1:257.

ARTSC8:452; C. Chen et al; Atherogenicity and Carcinogenicity of High-Arsenic Artesian Well Water; Arterisclerosis 8:452).

ATOX71:730; T. Ochi; Arsenic compound-induced increases in glutathione levels in cultured Chinese hamster V79 cells and mechanisms associated with changes in gamma-glutamylcysteine synthase activy, cystine uptake and utilization of cysteine; Archives of Toxicology 71:730.

ATOX79:183; T. Hayakawa, et al; A new metabolic pathway of arsenite: arsenic-glutathione complexes are substrates for human arsenic methyltransferase Cyt19; Archives of Toxicology 79:183.

BBA46:217; J. Bremer and D. Greenberg; Enzymic Methylation of Foreign Sulfhydryl Compounds; Biochimica et Biophysica Acta 46:217.

BBA628:241; P. T. Pisciotto and J. H. Graziano; Induction of Mucosal Glutathione Synthesis by Arsenic; Biochemica et Biophysica Acta 628:241.

BBA1073.416; A. Napolitano et al; 2-Aryl-1,3-thiazolidines as masked sulfhydryl agents for inhibition of melanogenesis; Biochimica et Biophysica Acta 1073:416.

BBA1379:233; A. Rabinkov, et al; The mode of action of allicin: trapping of radicals and interaction with thiol containing proteins; Biochimica et Biophysica Acta 1379:233.

BBA1463:20; T. Miron, et al; The mode of action of allicin: its ready permeability through phospholipid membranes may contribute to its biological activity. Biochimica et Biophysica Acta 1463:20.

BBBIO65:966; K. Seo, et al; Antibacterial activity of S-Methyl Methanethiosulfinate and S-Methyl 2-Propene-1-thiosulfinate from Chinese Chive towards *Escherichia coli* O157:H7; Bioscience, Biotechnology and Biochemistry 65:966.

BBRC242:1; I. Cotgreave and R. Gerdes; Recent Trends in Glutathione Biochemistry—Glutathione-Protein Interactions: A Molecular Link between Oxidative Stress and Cell Proliferation?; Biochemical and Biophysical Research Communications 242:1.

BDR71:124; C. A. Lammon and R. D. Hood; Effect of Protein Deficient Diets on the Developmental Toxicity of Inorganic Arsenic in Mice; Birth Defects Research 71:124.

BICH9:5105; V. Saxena and D. Wetlaufer; Formation of Three-Dimensional Structure in Proteins. I. Rapid Nonenzymic Reactivation of Reduced Lysozome; Biochemistry 9:5015.

BICH40:1688; H. E. Marshall and J. S. Stamler; Inhibition of NF-kB by S-Nitrosylation; Biochemistry 40:1688.

BIJ63:514; E. D. Wills; Enzyme Inhibition by Allicin, the Active Principle of Garlic; Biochemical Journal 63:514.

BJD139:655; A. Tosti et al; Calcipotriol ointment in nail psoriasis: a controlled double-blind comparison with betamethasone dipropionate and salicylic acid; British Journal of Dermatology 139:655.

BLOOD93:268; J. Dai, et al; Malignant Cells Can Be Sensitized to Undergo Growth Inhibition and Apoptosis by Arsenic Trioxide Through Modulation of the Glutathione Redox System; Blood 93:268.

BLOOD97:3931; O. Sondet; Mitochondria-targeting drugs arsenic trioxide and lonidamine bypass the resistance of TPA-differentiated leukemic cells to apoptosis; Blood 97:3931.

BLOOD98:805; J. M. Grad et al; Ascorbic acid enhances arsenic trioxide-induced cytotoxicity in multiple myeloma cells; Blood 98:805.

BMCCC6:155; G. G. Gyamlani et al; Acetaminophen toxicity: suicidal vs accidental; BioMed Central Critical Care 6:155.

BST23:S136; I. Das et al; Nitric Oxide Synthase is a Unique Mechanism of Garlic Action; Biochemical Society Transactions 23:S136.

BWHO78:1093; A. H. Smith, et al; Contamination of drinking-water by arsenic in Bangladesh: a public health emergency; Bulletin of the World Health Organization 78:1093.

CBEP12:350; M. L. Neuhouser et al; Fruits and Vegetables Are Associated with Lower Lung Cancer Risk Only in the Placebo Arm of the beta-Carotene and Retinol Efficacy Trial (CARET); Cancer Epidemiology, Biomarkers & Prevention 12:350.

CCHEM51:5; W. Herrmann et al; Disturbed Homocysteine and Methionine Cycle Intermediates S-Adenosylhomocysteine and S-Adenosylmethionine Are Related to Degree of Renal Insufficiency in Type 2 Diabetes; Clinical Chemistry 51:5.

CCP52:47; X. Hu et al; Arsenic trioxide induces apoptosis in cells of MOLT4 and its daunorubicin-resistant cell line via depletion of intracellular glutathione, disruption of mitochondrial membrane potential and activation of caspase-3; Cancer Chemotherapy and Pharmacology 52:47.

CCR8:3658; N. Bahlis et al; Feasibility and Correltaes of Arsenic Trioxide Combined with Ascorbic Acid-mediated Depletion of Intrecellular Glutathone for the Treatment of Relapsed/Refractory Multiple Myeloma; Clinical Cancer Research 8:3658.

CG9:131; V. L. Sparnins et al; Effects of organosulfur compounds from garlic and onions on benzo[a]pyrene-induced neoplasia and glutathione S-transferase activity in the mouse; Carcinogenesis 9:131.

CR61:725; H. Shirin et al; Antiproliferative Effects of S-Allylmercaptocysteine on Colon Cancer Cells When Tested Alone or in Combination with Sulindac Sulfide; Cancer Research 61:725.

CRT6:102; N. Scott, et al; Reactions of Arsenid (III) and Arsenic (V) Species with Glutathione; Chemical Research in Toxicology 6:102.

CRT10:27; M. Styblo et al; Comparative Inhibition of Yeast Glutathione Reductase by Arsenicals and Arsenothiols; Chemical Research in Toxicology 10:27.

DMD27:835; Metabolism of Diallyl Disulfide by Human Liver Microsomal Cytochromes P-450 and Flavin-containing Monooxygenases; Drug Metabolism and Disposition 27:835.

E185.96.D368; S. and E. Delany with A. Hearth, 1994; The Delany Sisters' Book of Everyday Wisdom; Kodansha International, New York, N.Y.

E185.96.D368:107; The Order of the Day (in E185.96.D368).

EHP108:617; A. H. Smith et al; Arseinc-Induced Skin Leaions among Atacameno People in Northern Chile Despite Good Nutrition and Centuries of Exposure; Environmental Health Perspectives 108:617.

EHP112:1104; S. Mitra, et al; Nutritional Factors and Susceptibility to Arsenic Caused Skin Lesions in West Bengal, India; Environmental Health Perspectives 112:1104.

EJB2:327; P. Jocelyn; The Standard Redox Potential of Cysteine-Cystine from the Thiol-Disulfide Exchange Reaction with Glutathione and Lipolic Acid; European Journal of Biochemistry 2:327.

EMM21:383; T. Das, et al; Modification of Clastogenicity of Three Known Clastogens by Garlic Extract in Mice In Vivo; Environmental and Molecular Mutagenesis 21:383.

EMM31:5; Z. Nemes and P. M. Steinert; Bricks and mortar of the epidermal barrier; Experimantal and Molecular Medicine 31:5.

ENVTP8:227; S. Maiti and A. J. Chatterjee; Differential response of cellular antioxidant mechanism of liver and kidney to arsenic exposure and its relation to dietary protein deficiency; Environmental Toxicology and Pharmacology 8:227.

FCT33:537; G. Stoewsand; Bioactive Organosulfur Phytochemicals in *Brassica oleracea* Vegitables—A Review; Food and Chemical Toxicology 33:537.

FEBS261:106; M. Focke, et al; Allicin, a naturally occurring antibiotic from garlic, specifically inhibits acetyl-CoA synthase; FEBS Letters 261:106.

FM29:348; K. N. Silashikanth, et al; A Comparative Study of Raw Garlic Extract and Tetracycline on Caecal Microflora and Serum Proteins of Albino Rats; Folia Microbiologica 29:348.

FRBM24:789; S. Mendiratta et al; Erythrocyte Ascorbate Recycling: Antioxidant Effects in Blood; Free Radicals in Biology and Medicine 24:789.

FRR28:485; H. Nakahara et al; Biochemical Properties of Human Oral Polymorphonuclear Leukocytes; Free Radical Research 28:485.

HTOX8:99; R. L. Shannon and D. S. Strayer; Arsenic-induced Skin Toxicity; Human Toxicology 8:99.

II62:529; E. L. Thomas et al; Antibacterial Activity of Hydrogen Peroxide and the Lactoperoxidase-Hydrogen Peroxide-Thiocyanate System against Oral Steptococci; Infection and Immunity 62:529.

IJDERM44:612; F. Dehghami et al; Healing effect of garlic extract on warts and corns; International Journal of Dermatology 44:612.

IJEB15:466; V. Sharma et al; Antibacterial Property of *Allium* SativumLinn.: in vivo & in vitro Studies; Indian Journal of Experimental Biology 15:466.

IJEB34:634; K. T. Agusti; Therapeutic values of onion (*Allium cepa* L.) and garlic (*Allium sativum* L.); Indian Journal of Experimental Biology 34:634.

IJEP27:871; D. N. G. Mazumder et al; Arsenic levels in drinking water and the prevalence of skin lesions in West Bengal, India; International Journal of Epidemiology 27:871.

ISBN9679786846; W. Fuchin and D. Yuhua 1998; Ginger, Garlic & Green Onion as Medicine; Pelanduk Publications, Malaysia.

ISBN9679786846:15; Chapter 2: Medical Diseases (in ISBN9679786846).

JACS66:1950; C. Cavallito and J. Bailey; Allicin, the Antibacterial Principle of *Allium sativum*. I. Isolation, Physical Properties and Antibacterial Action; Journal of the American Chemical Society 66:1950.

JACS66:1952; C. Cavallito, et al; Allicin, the Antibacterial Principle of *Allium sativum*. II. Determination of the Chemical Structure; Journal of the American Chemical Society 66:1952.

JACS69:1710; L. Small et al; Alkyl Thiosulfinates; Journal of the American Chemical Society 69:1710.

JAFC44:3426; G. Cao, et al; Antioxidant Capacity of Tea and Common Vegetables; Journal of Agricultural Food Chemistry 44:3426.

JAFC49:2592; L. Lawson and Z. Wang; Low Allicin Release from Garlic Supplements: a Major Problem Due to the Sensitivities of Allinase Activity; Journal of Agricultural and Food Chemistry 49:2592.

JAFC50:2488; H. Xiao and K. Parkin; Antioxidant Functions of Selected *Allium* Thiosulfinates and S-Alk(en)yl-L-Cysteine Sulfoxides; Journal of Agricultural and Food Chemistry 50:2488.

JAFC50:3856; O. Negishi, et al; Effects of Food Materials on Removal of *Allium*-Specific Volatile Sulfur Compounds; Journal of Agricultural and Food Chemistry 50:3856.

JAFC53:1974; L. Lawson and Z. Wang; Allicin and Allicin-Derived Garlic Compounds Increase Breath Acetone through Allyl Methyl Sulfide: Use in Measuring Allicin Bioavailability; Journal of Agricultural and Food Chemistry 53:1974.

JBC261:9694; E. L. Thomas and M. Fishman; Oxidation of Chloride and Thiocyanate by Isolated Leukocytes; The Journal of Biological Chemistry 261:9694.

JBC275:33404; S. V. Kala et al; The MRP2/cMOAT Transporter and Arsenic-Glutathione Complex Formation Are Required for Biliary Excretion of Arsenic; The Journal of Biological Chemistry 275:33404.

JCI63:53; E. Orringer and M. Roer; An Ascorbate-Mediated Transmembrane-Reducing System of the Human Erythrocyte; Journal of Clinical Investigation 63:53.

JESH38A: 141; D. N. Guha Mazumder; Chronic Arsenic Toxicity: Clinical Features, Epidemiology, and Treatment: Experiences in West Bengal; Journal of Environmental Health and Science 38A: 141.

JFCA2:327; G. Wierzbicka et al; Glutathione in Food; Journal of Food Composition and Analysis 2:327.

JFP60:67; K. Kyung and H. Fleming; Antimicrobial Activity of Sulfur Compounds Derived from Cabbage; Journal of Food Protection 60:67.

JLRPAW30:1703; R. Barnhart et al; Concentration-dependent antioxidant activity of probucol in low density lipoproteins in vitro: probucol degradation preceeds lipoprotein oxidation; Journal of Lipid Research 30:1703.

JN114:2241; M. Friedman et al; Nutritional Improvement of Soy Flour; The Journal of Nutrition 114:2241.

JN131:985S; B. Lau; Suppression of LDL Oxidation by Garlic; The Journal of Nutrition 131, supplement 3S:985S.

JN131:1010S; C. Borek; Antioxidant Health Effects of Aged Garlic Extract; The Journal of Nutrition 131, supplement 3S:1010S.

JN131:1067S; D. Lamm and D. Riggs; Enhanced Immunocompetence by Garlic: Role in Bladder Cancer and Other Malignancies; The Journal of Nutrition 131, supplement 3S:1067S.

JN131:1109S; T. Hoshino et al; Effects of Garlic Preparations on the Gastrointestinal Mucosa; The Journal of Nutrition 131:1109S, supplement 3S.

JN133:2171; H. P. Keiss et al; Garlic (*Allium sativum* L.) Modulates Cytokine Expression in Lipopolysaccharide-Activated Human Blood Thereby Inhibiting NF-kB Activity; The Journal of Nutrition 133:2171.

JSR65:165; S. Blair et al; Oral L-2-Oxo-4-thiazolidine Reduces Bacterial Translocation after Radiation in the Fischer Rat; Journal of Surgical Research 65:165.

LAM37:158; B. Chowdhury et al; Flurbiprofen, a unique non-steroidal anti-inflammatory drug with antimicrobial activity against *Trichophyton, Microsporum* and *Epidermophyton* species; Letters in Microbiology 37:158.

MCB148:183; K. Prasad et al; Antioxidant Activity of Allicin, an active Principle in Garlic; Molecular and Cellular Biochemistry 148:183.

MCT2:1295; T. Miron, et al; Inhibition of tumor growth by a novel approach: In situ allicin generation using targeted alliinase delivery; Molecular Cancer Therapeutics 2:1295.

MI2:125; S. Ankri and D. Mirelman; Antimicrobial properties of allicin from garlic; Microbes and Infection 2:125.

MOPM60:302; J. Liu et al; Overexpression of Glutathione S-Transferase II and Multidrug Resistance Transport Proteins Is Associated with Acquired Tolerance to Inorganic Arsenic; Molecular Pharmacology 60:302.

N207:1269; R. Hamm and K Hoffman; Changes in the Sulphydryl and Disulfide Groups in Beef Muscle Proteins During Heating; Nature 207:1269.

NARE24:2236; J. B. Matthews et al; Inhibition of NF-kB DNA binding by nitric oxide; Nucleic Acids Research 24:2236.

NUCA34:42; R. Munday and C. Munday; Low Doses of Diallyl Disulfide, a Compound Derived From Garlic, Increase Tissue Activities of Quinone Reductase and Gluta-thone Transferase in the Gastrointestinal Tract of the Rat; Nutrition and Cancer 34:42.

P38:747; E. Elnima et al; The Antimicrobial Activity of Garlic and Onion Extracts; Pharmazie 38:747.

PHYRES3:50; S. Nakagawa et al; Prevention of Liver Damage by Aged Garlic Extract and Its Components in Mice; Phytotherapy Research 3:50.

PHYRES17:97; S. Banerjee, et al; Garlic as an Antioxidant: The Good, The Bad and The Ugly; Phytotherapy Research 17:97.

PHYRES18:389; M. Mukherjee et al; Prevention of Bone Loss by Oil Extract of Garlic (*Allium sativum* Linn.) in an Ovariectomized Rat Model of Osteoporosis; Phytotherapy Research 18:389.

PM56:668; F. Jung et al; Effect of Different Garlic Preparations on the Fluidity of Blood, Fibrolytic activity, and Peripheral Microcirculation in comparison with placebo; Planta Medica 56:668.

PM59:A688; L. Lawson and Z. Wang; Pre-Hepatic Fate of the Organosulfur Compounds Derived from Garlic (*Allium sativum*); Planta Medica 59:A688.

PM60:417; J. Imai, et al; Antioxidant and Radical Scavenging effects of Aged Garlic Extract and its Constituents; Planta Medica 60:417.

PM67:13; L. Lawson, et al; Allicin Release under Simulated Gastrointestinal Conditions from Garlic Powder Tablets Employed in Clinical Trials on Serum Cholesterol; Planta Medica 67:13.

PNAS98:1643; S. X. Liu et al; Induction of oxyradicals by arsenic: Implication for mechanism of genotoxicity; Proceedings of the National Academy of Seicnce 98:1643.

Q11.N45V1030; New York Academy of Sciences, 2004; Signal Transduction Pathways, Chromatin Structure, and Gene Expression Mechanisms as Therapeutic Targets; New York Academy of Sciences, New York, N.Y.

Q11.N45V1030:1; S. Delhalle et al; A Beginner's Guide to NF-kB Signalling Pathways (in Q11.N45V1030).

QD305.S3C48; Edited by S. Patai and Z. Rappoport 1993; Supplement S: The Chemistry of Sulphur-containing Functional Groups; John Wiley & Sons, New York, N.Y.

QD305.S3C48:633; R. Singh and G. Whitesides; Thiol-Disulfide Interchange (in QD305.S3C48).

QD305.S3S14; Edited by Z. Alfassi, 1999; S-Centered Radicals; John Wiley & Sons, New York, N.Y.

QD305.S3S14:289; P. Wardman; Thiyl Radicals in Biology: Their Role as a "Molecular Switch" Central to Cellular Oxidative Stress (in QD305.S3S14).

QH545.A77; Committee on Medical and Biologic Effects of Environmental Pollutants; Arsenic; National Academy of Sciences, Washington, D.C.

QH545:A77:4; Chemistry of Arsenic (in QH545.A77).

QH545.A77:117; Biologic Effects of Arsenic on Plants and Animals (in QH545.A77).

QP141.N48; H. Newstrom, 1993; Nutrients Catalog; McFarland & Company Inc. Jefferson, N.C.

QP141.N48:249; Cysteine (in QP141.N48).

QP535.N1N547; L. J. Ignarro, 2000; Nitric Oxide—Biology and Pathobiology; Academic Press, New York, N.Y.

QP535.N1N547:41; K. M. Miranda et al; The Chemical Biology of Nitric Oxide (in QP535.N 1N547).

QP535.O1R43; Edited by D. L. Gilbert and C. A. Colton; Reactive Oxygen in Biological Systems, 1999; Kluwer Academic, New York, N.Y.

QP535.O1R43:33; R. Huie and P. Neta; Chemistry of Reactive Oxygen Species (in QP535.O1R43).

QP551.M433; H. A. McKenzie, 1971; Milk Proteins—Chemistry and Molecular Biology; Academic Press, New York, N.Y.

QP551.M433:331; W. G. Gordon; alpha-Lactalbumin (in QP551.M433).

QP551.P6976; C. Bodwell et al; Protein Quality in Humans: Assessment and in vitro Estimation; AVI Publishing Company, Inc., Westport, Conn.

QP551.P6976:3; N. Serimshaw; Nutritional Significance of Protein Quality: A Global View (in QP551.P6976).

QP551.P6976:98; R. Bressani et al; A Short-Term Procedure to Evaluate Protein Quality in Young and Adult Human Subjects (in QP551.P6976).

QP552.P4S93; Chaired by D. Parsons, 1976; Peptide Transport and Hydrolysis; Van Gorcum, Assen, The Netherlands.

QP552.P4S93:151; Y. Kim; Intestinal mucosal hydrolysis of proteins and peptides (in QP552.P4S93).

QP55.P48; G. Petsko and D. Ringe, 2004; Protein Structure and Function; New Science Press Ltd, London, UK.

QP551.P48:92; Control by pH and Redox Environment (in QP551.P48).

QP552.G58F585; edited by J. Vina, 1990; Glutathione: Metabolism and Physiological Functions; CRC Press, Boca Raton, Fla.

QP552.G58F585:125; R. Freedman; The Formation of Disulfide Bonds in the Synthesis of Secretory Proteins: Properties and Role of Protein Disulfide-Isomerase (in QP552.G58G585).

QP552.G58F85; A. Larsson et al, 1983; Functions of Glutathione—Biochemical, Physiological, Toxicological, and Clinical Aspects; Raven Press, New York, N.Y.

QP552.G58F85:205; T. E. Creighton; Pathways and Energetics of Protein Disulfide Formation (in QP552.G58F85).

QP552.G58G54; Edited by N. Taniguchi et al, 1989; Glutathione Centennial: Molecular Perspectives and Clinical Implications; Academic Press, New York, N.Y.

QP552.G58G54:57; N. Tateishi and Y. Sakamoto; Regulation of Glutathione Level in Primary Cultured Hepatocytes (in QP552.G58G54).

QP552.G58G54:73; H. Gilbert; Thermodynamic and Kinetic Constraints on Thiol/Disulfide Exchange Involving Glutathione Redox Buffers (in QP552.G58G54).

QP552.G58G54:407; S. Bannai et al; Regulation of Glutathione Level by Amino Acid Transport (in QP552.G58G54).

QP601.E515; Edited by W. Jakoby, 1980; Enzymatic Basis of Detoxification Volume II; Academic Press, New York, N.Y.

QP601.E515:131; R. Weisiger and W. Jakoby; S-Methylation: Thiol S-Methyltransferase (in QP601.E515).

QP601.W38V3; J. L. Webb; Enzyme and Metabolic Inhibitors—Volume III, 1966; Academic Press, New York, N.Y.

QP601.W38V3:595; Arsenicals (in QP601.W38V3).

QP606.G59G59; N. Vermeulen et al, 1996; Glutathoine S-Transfetases: Structure, Function and Clinical Implications; Taylor & Francis Ltd., London, England.

QP606.G59G59:199; T. Ishikawa and K. Akimaru; Transport of Glutathone S-Conjugates from Cancer Cells: Function and Structure of the GS-X Pump (in QP606.G59G59).

QP722.A8A586; Edited by L. Packer, et al, 2002; The Antioxidant Vitamins C and E; AOCS Press, Champaign, Ill.

QP722.A8A586:133; L. Packer and U. Obermuller-Jevic; Vitamin E: An Introduction (in QP722.A8A586).

QP801.G6C6; Edited by S. Colowick et. al, 1954; Glutathione; Academic Press, New York, N.Y.

QP801.G6C6:3; M. Calvin; Mercaptans and Disulfides: Some Physics, Chemistry, and Speculation (in QP801.G6C6).

R850.A1A3V459; edited by Jackson et al, 1999; Impact of Food Processing on Food Safety; Kluwer Academic, New York, N.Y.

R850.A1A3V459:161; G. Sarwar et al; Influence of Feeding Alkaline/Heat Processed Proteins on. Growth and Protein and Mineral Status of Rats (in R850.A1A3V459:161).

RA784.N836; Edited by P. Lachance, 1997; Nutraceuticals: Designer Foods III Garlic, Soy and Licorice; Food & Nutrition Press, Inc. Trumbull, Conn.

RA784.N836:311; G. Guhr and P. Lachance; Role of Phytochemicals in Chronic Disease Prevention (in RA784.N836).

RA1231.A7M44; A. A. Meharg, 2005; Venomous Earth—How arsenic caused the world's worst mass poisoning; Macmillan, New York, N.Y.

RA1231.A7M44:170; JOI BANGLA! (in RA1231.A7M44).

RA1231.A7N38; Subcommittee on Arsenic in Drinking Water; Arsenic in Drinking Water, 1999; National Academy Press, Washington, D.C.

RA1231.A7N38:150; Disposition of Inorganic Arsenic (in RA1231.A7N38).

RA1231.A7N38:177; Biomarkers of Arsenic Exposure (in RA1231.A7N38).

RB170.B57; Edited by L. Packer and E. Cadenas, 1995; Biothiols in Health and Disease; Marcel Dekker Inc, New York, N.Y.

RB170.B57:287; M, Inoue, et al; Biochemical and Clinical Aspects of Extracellular Glutathione and Related Thiols (in RB170.B57).

RB170.H36; E. Cadenas and L. Packer, 2002; Handbook of Antioxidants; Marcel Dekker, Inc. New York, N.Y.

RB170.H36:235; W. G. Seims et al; Oxidative Breakdown of Carotenoids and Biological Effects of Their Metabolism (in RB170.H36).

RB170.O96; Edited by C. Pasquier, R. Oliver, C. Auclair and I. Packer, 1994; Oxidative Stress, Cell Activation and Viral Infection; Birkhauser Verlag, Basel Switzerland.

RB170.O96:101; A. Meister; The Antioxidant Effects of Glutathione and Ascorbic Acid (in RB170.O96).

RB170.O96:285; W. Droge et al; Abnormal Redox Regulation in HIV Infections and other Immunodeficiency Diseases (in RB170.O96).

RM666.G15K6313; H. P. Koch and L. D. Lawson, 1996; GARLIC The Science and Therapeutic Application of *Allium sativum* L. and Relates Species; Williams & Wilkins, Baltimore, Md.

RM666.G15K6313:190; H. P. Koch and L. D. Lawson; Antioxidant Effects: Active Compounds (in RM666.G15K6313).

RR2:392; P. Alexander et al; Mode of Action of Some Substances Which Protect against the Lethal Effects of X-Rays; Radiation Research 2:392.

S97:356; E. S. G. Barron, T. P. Singer; Enzyme Systems Containing Active Sulphydryl Groups. The Role of Glutathione; Science 97:356.

TAP154:287; R. A. Zakharyan and H. V. Aposhian; Arsenite Methylation by Methylvitamin B12 and Glutahtione Does Not Require an Enzyme; Toxicology and Applied Pharmacology 154:287.

TAP183:99; E. M. Brambila et al; Chronic Arsenic-Exposed Human Prostate Epithelial Cells Exhibit Stable Arsenic Tolerance: Mechanistic Implications of Altered Cellular Glutathione and Glutathione S-transferase; Toxicology and Applied Pharmacology 183:99.

TAP206:198; CJ Chen et al; Biomarkers of exposure, effect, and susceptibility of arsenic-induced health hazards in Taiwan; Toxicology and Applied Pharmacology 206:198.

TL37:41; M. Vahter and E. Marafante; Effects of Low Dietary Intake of Methionine, Choline or Proteins on the Biotransformation of Arsenite in the Rabbit; Toxicology Letters 37:41.

TL69:15; R. White et al; Toxicity Evaluations of L-cysteine and Procysteine, a Cysteine Prodrug, Given Once Intravenously to Neonatal Rats; Toxicology Letters 69:15.

TOXICOL79:195; H. Huang, et al; Glutathione as a cellular defence against arsenite toxicity in cultured Chinese hamster ovary cells; Toxicology 79:195.

TOXSCI70:183; M. Schuliga et al; Upregulation of Glutathione-Related Genes and Enzyme Activities in Cultured Human Cells by Sublethal Concentrations of Inorganic Arsenic; Toxicological Sciences 70:183.

TOXSCI91:70; C. Kojima et al; Chronic Exposure to Methylated Arsenicals Stimulates Arsenic Excretion Pathways and Induces Arsenic Tolerance in Rat Liver Cells; Toxicological Sciences 91:70.

TP371.8F66; R. Mollins; Food Irradiation: Principles and Applications; Wiley Interscience, New York.

TP371.8F66:131; R. A. Molins; Irradiation of Meats and Poultry (in TP371.8F66).

TP371.8P74; E. Josephson et al; Preservation of Food by Ionizing Radiation, Volume I; CRC Press Inc., Boca Raton, Fla.

TP371.8P74:279; J. Deihl; Radiolytic Effects in Foods (in TP371.8P74).

TP453.P7F68; Edited by S. Nakai and H. Modler 1996; Food Proteins: Properties and Characterization; VHC Publisners, New York, N.Y.

TP453.P7F68:23; R. Ludescher; Physical and Chemical Properties of Amino Acids and Proteins (in TP453.P7F68).

TP453.P7F68:281; M. Friedman, Nutrition (in TP453.P7F68)

US002432797; R. A. Peters et al; Organic Thiol Antitoxic Agents; U.S. Pat. No. 2,432,797.

US004486403; G. Mechanic and I. Binderman; Composition for and treatment of teeth; U.S. Pat. No. 4,486,403.

US005296500A; G. G. Hillebrand; Use of N-acetyl-L-cysteine and Derivatives for Regulating Skin Wrinkles and/or Skin Atrophy; U.S. Pat. No. 5,296,500.

US005451412A; G. Bounous et al; Biologically Active Undenatured Whey Protein Concentrate as Food Supplement; U.S. Pat. No. 5,451,412.

US005906811A; T. Hersh; Intra-Oral_antioxidant Preparation; U.S. Pat. No. 5,906,811.

US2004/0235946A1; D. M. Ott; Organosulfur Prodrugs for the Prevention and Treatment of Infectious Diseases and Pathologic Immune System Response; US Patent Application Publication US2004/0235946A 1.

US2005/0260250A1; D. M. Ott; Medicinal Products Incorporating Bound Organosulfur Groups; US Patent Application Publication US2005/0260250A1.

4. DESCRIPTION OF THE PRIOR ART

4.1 Personal Care Products

Personal care products are commonly used by individuals throughout their lifetime to promote and maintain health and personal appearance. For example, toothpaste has been proven to be beneficial for the maintenance of both oral heath and an attractive smile. A wide variety of personal care products are commonly applied to the skin as moisturizers, sun screens, anti-oxidants, anti-acne, anti-athlete's foot, insect repellants, deodorants, etc.

Some personal care products are used on an as-needed basis for the treatment of occasional conditions that are not serious enough to require medical care. For example, low-dosage cortisone cream is available over the counter and is commonly used for the treatment of mosquito stings, poison ivy, or the occasional mild rash. Unfortunately, the chronic use of cortisone leads to the thinning of the skin, so it should not be regularly used for chronic skin conditions such as eczema (or for diaper rash), even though it is readily available over the counter.

The general properties of all of these personal care products are presumably already well known by the reader (who has probably used all of them!), but the relationship of membrane permeable organosulfur compounds to these (which is the subject of the present invention) is a somewhat more esoteric subject. In this case, the applicable prior art is the medicinal use and biochemistry of thiols, disulfides, and thiosulfinates.

For life on earth, cysteine (including the cysteine in proteins and peptides such as glutathione) is the overwhelming biothiol, typically providing well over 90% of the total thiol content of the organism. The importance of cysteine (and of glutathione) to life in general is well known to biologists, yet the applicant believe that some important roles have been little known, and that there are others yet to be discovered. The Applicant believes that just as water has been determined to be essential for life, biothiols are essential to all forms of life that have evolved on this planet.

For animals, the primary biological source of thiols and disulfides has always been dietary protein. The only significant sources of dietary thiosulfinates are the *allium* and cruciferous vegetables (e.g. garlic, onions, cabbage, broccoli). An important distinction from protein is that the these vegetables produce organosulfur compounds that can metabolize to membrane permeable compounds (cysteine is not membrane permeable). In addition, these vegetables can be a significant source of thiols and disulfides.

Along with the endogenous biothiols, the medicinal, toxic, and anti-social properties of the dietary alliums (which have been studied more extensively than the cruciferous vegetables) will be reviewed in order to provide context for the present invention. As will be seen below, the majority of research related to the medicinal use of thiols has utilized compounds that are ingested orally. However, the Applicant has discovered that the *allium* related compounds, when applied topically, share many of these beneficial properties, including the antimicrobial and antioxidant ones which the Applicant has discovered when administering these compounds orally (US2004/0235946A1, US2005/0260250A1).

4.2 Cysteine—Amino Acid, Biothiol, and Glutathione Precursor

Cysteine is a sulfur containing amino acid which is an important constituent of proteins. In fact, the SH group of cysteine when ionized (i.e. to $CyS^-$) is the most reactive group in proteins (TP453.P7F68:23). The active site of many enzymes (e.g. proteases) involves cysteine, where the reactivity of the $CyS^-$ group contributes to the activity of the enzyme.

Cysteine is a thiol (it has a terminal "SH" group) and shares many properties with other biothiols. It is able to participate in thiol-disulfide exchange reactions with almost all types of disulfides, resulting in a wide variety of mixed disulfides (QD305.S3C48:633). Thiol-disulfide exchange reactions allow the formation of disulfide bonds (which are covalent bonds, so they are quite strong) and their later separation, without significant energy involvement other than the thermal energy that brings them together or apart.

The formation of the tertiary structure of proteins ("conformation", from protein folding) depends upon the proper formation of disulfide bonds between pairs of cysteines within the polypeptide chain of the protein. These disulfide bonds can stabilize or regulate the protein structure and activity. Disulfide bonds can also link adjacent proteins, providing structure to tissues. Disulfide bonds also affect the stiffness of the eye lens, and the excessive formation of disulfide bonds is implicated in the development of cataracts (BBRC242:1).

Many types of proteins are "redox regulated" (ARR1:257), with their function and/or activity depending both upon the current conformation and also upon whether critical cysteinyl SH groups (CySH) on the protein are currently blocked (CySSR), or are in thiol form (CySH) or are in thiolate form ($CyS^-$). However, the Applicant notes that the significance and degree of redox regulation within the cell remains somewhat controversial (or incompletely appreciated). For example, the chapter "Control by pH and Redox Environment" in the textbook "Protein Structure and Function" (published in 2004) states that "cysteine residues in proteins are usually fully reduced to SH groups inside the cell", and emphasizes that the formation of disulfide S—S bridges occurs primarily in proteins that have been secreted to the extracellular environment (QP551.P48:92). The authors attribute the intracellular control of proteins primarily to the effect of pH on the ionization of protein polar side chains. While perhaps literally correct, this neglects the importance of those conditions in which a significant proportion intracellular —SH groups are not fully reduced, which the Applicant believes are the most important phases of redox regulation controlling the birth (e.g. in mitosis) and death of the cell (e.g. in apoptosis).

Cysteine tends to auto-oxidize to cysteine disulfide (cystine, CySSCy) in the presence of oxygen. Inside cells, the "reductive" environment provided by the maintenance of reduced glutathione (by the enzyme glutathione reductase) tends to keep the majority of cysteine reduced (CySH), but in an extracellular environment, cysteine disulfide readily forms. Cysteine disulfide has low solubility and when it is in too high a concentration it can result in the formation of kidney stones.

Cysteine exhibits toxicity in large dosage, but non-toxic prodrugs exist (TL69:15), such as N-acetylcysteine (NAC) and L-2-Oxo-thiazolidine (OTZ) (JSR65:165). The reactivity of these prodrugs is lower than that of cysteine because instead of having an exposed "SH" they tend to form a thiazolidine ring in water at a neutral pH (QP801.G6C6, pages 21-30).

4.2.1 Dietary Sources Cysteine and Other Sulfur Amino Acids

Cysteine deficiency may be common even in people who eat "enough" protein. Many sources of dietary protein have low content of cysteine and methionine (another amino acid that can be metabolized to cysteine in vivo, by the liver). People who don't eat much animal protein are at risk because most other foods have low content of sulfur amino acids (SAA, e.g. the sum of cysteine, cystine, and methionine).

The Nutrients Catalog (QP141.N48:249) lists the amino acid contents of a wide variety of food sources (in milligrams per 100 g). The cysteine content of animal tissue protein sources, seeds and some types of legumes and some types of nuts tend to range from ~400 (roasted chicken, soybean flour) down to ~150 (beef frankfurter). Cereals, rice, and most types of beans have from ~200 down to ~100. Cheeses, evaporated milk, tofu, and some types of nuts tend to be in the range of 120 down to 40. Fruits and vegetables tend to be in the range of 30 down to 10. Beverages, foods with a high water content, some processed foods, and some fruits have less than 10 (e.g. orange juice, watermelon, cucumbers, pumpkin, canned carrots, and apples). As a rule of thumb, animal protein has 10× the cysteine content of fruits and vegetables, with cheeses, nuts, and beans in between.

In 2001, it was reported that the current recommendation for daily dietary sulfur amino acid consumption were low by almost a factor of two (13 mg/kg of body weight instead of 25 mg/kg) due to an arithmetic error when the requirements were determined experimentally in 1955 (AJCN74:756). Therefore, a 70 kg person should actually be consuming 1750 mg of sulfur amino acids per day. Another problem with the way that the dietary sulfur amino acid requirements were determined is that the experiments were based on "nitrogen balance" which only measures the amount of the amino acid that is needed for protein formation (weight maintenance) and does not take into account other biological requirements for cysteine (such as glutathione synthesis and taurine synthesis).

The 1960s were years of concern for protein quality, with predictions of an impending "protein crisis" in developing countries. But the global perception of world food and nutrition problems abruptly changed in 1971, when a joint FAO/WHO "Expert Committee on Energy and Protein Requirements" concluded that the focused effort should be on meeting the caloric requirements instead. "It became fashionable to emphasize the deficiency of energy in the diets of low-income populations and to point out that if this were corrected, protein needs, as indicated by the 1971 committee report would be met" (QP551.P6976:3).

The need for dietary sulfur amino acid consumption continues to receive little emphasis in dietary recommendations, and in the opinion of the Applicant, it is much too easy for people who think that they are eating well to actually not be consuming enough sulfur amino acids. Regarding dietary protein, the newly published "Dietary Guidelines for Americans 2005" only briefly mentions proteins (and not individual amino acid requirements at all) and states that "most Americans are already consuming enough . . . . As such, protein consumption, while important for nutritional adequacy, is not a focus of this document." In the opinion of the Applicant, by limiting their consideration to "most Americans", these guidelines are not providing guidance to those who need it most.

Their recommendations for fruits, vegetables, and other nutrients seem reasonable in most respects, but what percentage of the American population will actually consume 3 cups of milk a day? And what about those who dont? Those who avoid milk consumption are specifically recommended to find other sources rich in calcium, potassium, magnesium, zinc, iron, riboflavin, vitamin A, folate, and vitamin D, but protein is not mentioned in the list. In the section on "Vegetarian Choices", it is stated that "½ ounce of nuts or ¼ cup of legumes is considered equivalent to 1 ounce of meat, poultry or fish", which is probably correct in terms of total protein content, but does not take into account that the bioavailable content of SAA in nuts and legumes is lower. For example, their recommended 5.5 ounces of meat would contain ~500 mg of SAA, but their "equivalent" of 2.75 ounces of nuts would contain only ~250 mg per day (not very much compared to the 1750 mg that is needed).

Glutathione in food varies dramatically, such that well fed Americans can have a 40:1 range in its consumption (JFCA2:327). However, dietary glutathione probably has no special significance other than as a source of cysteine. The glutathione inside cells is created from its constituent amino acids (glutamic acid, cysteine, and glycine). Of these, cysteine is almost always the limiting amino acid, because glutamic acid and glycine are relatively common in foods.

Dietary taurine comes exclusively from animal sources (there is no taurine in plants), but the body can produce taurine if necessary from excess cysteine. In other words, without enough taurine consumption, or extra cysteine consumption (beyond the requirements for protein and glutathione synthesis), taurine deficiency can occur. One effect of taurine deficiency is impaired cholesterol metabolism, which can lead to cardiovascular disease (AMR6:78).

Dietary alliums are a good source of cysteine, but their unpleasant side effects when consumed in other than small quantities limit their ability to serve as a primary source of cysteine.

4.2.2 Anti-Nutritional Factors

4.2.2.1 Cysteine Loss from Food Processing and Cooking.

The sulfhydryl and disulfide groups of proteins (i.e. the cysteine and cystine) are the most vulnerable amino acids to food processing, and have been shown to be easily damaged by heat during cooking. Heating above 30 degrees C. causes the progressive denaturation of the protein, and heating above 70 degrees C. causes the progressive irreversible destruction of cysteine (N207:1269). Interestingly, although cooking increases the digestibility of protein in general (due to the thermal unfolding of the proteins), given that cysteine is the limiting amino acid in foodstuffs the damage to the cysteine can lower the net protein quality of cooked food.

Foods are treated with heat and alkali for many purposes such as to sterilize/pasteurize, to improve flavor or texture, to destroy toxic or anti-nutritional factors, to promote desirable physical properties, and to solubilize proteins (R850.A1A3V459:161). The formation of lysinoalanine (LAL) mainly via the reaction between the lysine and cysteine residues that occurs during heat treatment in the presence of alkaline not only results in cysteine loss, but the LAL itself is toxic and can cause kidney damage. Experimentally, the alkaline treatment with 0.1N NaOH at room temperature for 1 hour followed by heat treatment at 75 degrees C. for 3 hours and then neutralization with 10N HCl resulted in the loss of 20% of the lysine and 75% of the cysteine, along with the HPLC detectable formation of LAL (R850.A1A3V459:161). The anti-nutritional factors formed during alkaline/heat treatment also caused a reduction of weight gain of rats of 25% compared to those fed untreated diets (R850.A1A3V459:161). Other chemical treatments of foods that affect the cysteine content include browning (e.g. the Maillard reaction), acetylation, and glycosylation.

The thermal sterilization of beef has been shown to result in a retention of cysteine content of only 29% (by weight percentage). Sterilization by freezing yields a cysteine retention of 28%. Therefore, these both produce a loss comparable to that of gamma irradiation (26% retention) or electron irradiation (28% retention) (TP371.8F66:131). The main point of the author of this paper is that irradiation is not any more destructive than other methods of sterilization that are commonly used, but the figures cited substantiate the substantial loss of cysteine that occurs during the routine processing of foods. Foods that have been sterilized for storage are also likely to be cooked prior to eating, so the cumulative loss of cysteine is likely to be even greater.

The sulfhydryl and disulfide groups of proteins are the most easily damaged components of food from anti-microbial radiation treatment, as is shown by the 100-fold greater sensitivity of "SH" enzymes to inactivation by irradiation relative to the "non-SH" enzymes (TP371.8P74:279). This indicates that it is probably the loss of cysteine in essential enzymes that kills the microbes. Foods that have been sterilized for storage are also likely to be cooked prior to eating, so the cumulative loss of cysteine is likely to be somewhat greater than the figures given here.

4.2.2.2 Foods that Inhibit Digestive Enzymes

Legumes, especially soy beans, inhibit digestive enzymes so much that they not only have poor digestibility themselves but they also reduce the digestion of other proteins being consumed in the same meal, unless the enzyme inhibitors are completely deactivated (TP453.P7F68:281). The digestive enzymes that are secreted by the digestive system are rich in cysteine and are normally "recycled" (i.e. digested) along with the food, but the inhibitors in legumes prevent these enzymes from being successfully digested and reabsorbed, so there can be a net cysteine loss from the digestive process itself. Therefore, protease inhibitors and lectins in raw soybean meal are found to be anti-nutritional (they actually cause weight loss when consumed along with other food).

Experiments with rats show that when added to a casein (milk protein) diet, beans decrease growth, diet efficiency, protein digestibility and protein utilization. Although heat treatment (to deactivate the inhibitors) improved the nutritional value of the mixed bean-casein diet, the values were still lower that a diet of 10% casein alone (TP453.P7F68: 281). In other words, even after the heat treatment, the beans are anti-nutritional.

Most commercially available soy flours have been heat treated but still retain 5-20% of the original inhibitor activity because more heat treatment would cause excessive damage to the nutritive value of soy proteins (in addition to the cysteine loss). Supplementation with cysteine or NAC prior to heat treatment deactivates the enzyme inhibitors more effectively than the heat treatment alone, allowing a lower temperature to be used and providing some cysteine supplementation. For example, adding cysteine (2% by weight) and then heating the soy flour at 65 degrees C. for 1 hour deactivates the trypsin enzyme inhibitor by over 90%, improving the protein efficiency ratio (PER) by a factor of 2.43 (JN114: 2241). Much of this PER improvement is presumably due to the cysteine supplementation, given that cysteine is typically the limiting amino acid in soy flour.

4.2.2.3 Unbalanced or Excessive Amino Acid Consumption

Unbalanced amino acid concentrations can cause a variety of anti-nutritive conditions. As an interesting side note, although rice and black beans are each incompletely balanced protein sources individually, they complement each other and can form a well balanced source of protein when consumed together in the same meal (QP551.P6976:98).

Even at the cellular level, an unbalanced amino acid concentration can cause pathology. Because cystine and glutamate share the same membrane transport system (RB170.O96:285), glutamate competitively inhibits the cellular uptake of cystine (QP552.G58G54:407). An imbalance between extracellular glutamate and cystine is implicated in the lethality of lung cancer (RB170.O96:285), the pathology of AIDS (RB170.O96:285) and the progression of aging (ARR1:257).

4.2.2.4 The Regulation of the Digestive Uptake of Amino Acids (Simplified)

In mammals, the hydrolysis of proteins (digestion) is performed by protease and peptidase enzymes (in conjunction with the denaturation of the proteins by stomach acid). After the enzymes in the stomach and the interior of the intestine break the proteins into small fragments (peptides), the smallest of which (e.g. dipeptides, each consisting of a pair of amino acids) are then preferentially taken up by the "brush boarder" cells that line the small intestine (QP552.P4S93: 151). Within these brush boarder cells, multiple "dipeptidase" enzymes which are each specific to the second amino acid of the dipeptide (and are feedback regulated by the concentration of this amino acid in the cytosol) can further break down the dipeptide into its two amino acids. The individual amino acids then leave the brush boarder cells on the other side and enter the portal vein of the blood stream.

The transport of the amino acids on the blood system side of the cell is actually bidirectional, therefore the concentration of each amino acid within the cell is in rough equilibrium with its concentration in the blood stream. This automatically inhibits the specific dipeptidase that produces this amino acid from the dipeptides that contain it as the second peptide. (Because there are 20 types of amino acids commonly found in proteins, there could be ~400 types of dipeptides in food, yet this scheme allows the regulation of amino acid uptake with only ~20 dipeptidases being needed.)

The transport of the dipeptides on the intestinal side of the brush boarder cells is also bi-directional; therefore the concentration of dipeptides inside the cell approximates the concentration in the small intestine. This automatically returns to the small intestine (eventually) from the cell the excess of those dipeptides for which the dipeptidase is inhibited, because as the other dipeptides are digeseted to individual amino acids, only the dipeptides that are inhibited retain a high concentration in the cell. The dipeptides that are not taken up by the brush boarder cells (or are returned undigested) pass on to the large intestine.

4.2.3 Some Types of Cells can Uptake Cystine and Efflux Cysteine

Some types of cells (e.g. macrophages, fibroblasts, and hepatocytes) have been found to be able to uptake cystine (CySSCy) via a membrane transport protein and then to reduce it to cysteine (2 CySH) via thiol-disulfide exchange reactions with glutathione (GSH) inside the cell and to subsequently release the cysteine to the extracellular environment (RB170.O96:285).

The Applicant notes that for this limited number of cell types, active transport through the cell membrane couples the intracellular antioxidant network to the extracellular environment via the following mechanism. In the extracellular environment diffusion and exchange reactions can semi-randomly transform the nature of the product of an oxidation event until it shows up as cystine (CySSCy) at the outer surface of the cell membrane and is taken up for transport. Then inside the cell, diffusion and exchange reactions can semi-randomly transform the nature of the oxidized intermediate until it shows up as intracellular GSSG, which is then rapidly removed by the enzyme glutathione reductase, producing 2 GSH. Following further semi-random exchange reactions, reduced cysteine (CySH) is transported back through the cell membrane to the extracellular environment. This contributes to the creation and maintenance of a generally reductive environment, including the local environment outside the cell, at the expense of the energy provided to glutathione reductase to drive the system.

In addition to its antioxidant function, the efflux of cysteine from these cells supports the cell-to-cell transport of cysteine (QP552.G58G54:407), which is important because almost all other cell types only have the ability to uptake cysteine (CySH) and would "starve" if only provided with cystine (BCHS370:109). Proper function and immune response of lymphocytes appears to require a local supply of extracellular cysteine (e.g. from adjacent macrophage cells) because these cells need to be provided with a higher cysteine concentration than that in circulation (AJM91_3C:140S).

4.2.4 The Intensified Delivery of Cysteine

Because cysteine is typically the limiting amino acid for most diets, insufficient dietary cysteine is the most likely cause of protein deficiency. Therefore the augmentation of cysteine delivery can be beneficial in the prevention of its deficiency, perhaps even reducing the amount of total protein that needs to be consumed. (In other words, if a given mix of dietary proteins is low in cysteine by 20% relative to the ideal mix of amino acids, significantly more total protein will need to be consumed (25%), just to get enough cysteine.)

4.2.4.1 Cysteine Supplementation of Foodstuffs

It would seem that the supplementation of foodstuffs with cysteine would be an effective way to improve the quality of proteins, and this has been done experimentally with soy flour (JN114:2241). But the addition of amino acids to food is regulated by law (and administered by the FDA in the United States). The applicable US law is section 172.320 ("Amino Acids") of Title 21 ("Food Additives Permitted for Direct Addition to Food for Human Consumption"). There are several ways in which this law makes it impractical to use cysteine as a food additive, as can be seen from the consideration of its subsections (c), (d), and (e):

Subsection (c) prohibits the addition of amino acid(s) to any food that is not already a significant source of dietary protein (at least 6.5 grams, based upon 10% of the adult male Recommended Daily Allowance). The added amino acid(s) must result in a statistically significant increase on the Protein Efficiency Ratio (PER) over the naturally occurring protein in the food, and the resulting PER must equal or exceed that of casein (a standard mix of milk proteins). The total amount of cysteine (additive plus the amount naturally present) cannot exceed 2.3% by weight of the total protein. (This restricts the total cysteine to less than that of whey protein (2.5%), another type of standard mix of milk proteins.) The Applicant notes that this also makes illegal the degree of cysteine supplementation that was utilized experimentally for the improvement of soy flour (2% plus the native cysteine of soy flour is >2.3%, see section 4.2.2.2 above).

Subsection (d) requires that the PER be measured by AOAC method 43.21243.216, which involves feeding the protein to rats and measuring their weight gain. (In other words, animal testing is required.) The manufacturer or person needs to repeat these tests sufficiently to "keep and maintain throughout the period of his use of the additive(s) and for a minimum of 3 years thereafter, records of the tests required by this paragraph and other records required to assure compliance with this regulation and shall make such records available on request . . . ."

Subsection (e) requires that the label list the name, chemical form, and amount of each amino acid contained in any mixture, and adequate instructions for use (cooking instructions???) to provide a finished food meeting the limitations prescribed by paragraph (c).

It can be seen from these regulations that the addition of amino acids to foodstuffs is (correctly) regarded as potentially hazardous, but the destruction of amino acids (e.g. by anti-microbial radiation) is not. In other words, although many additives (and processing procedures) are designated Generally Recognized As Safe (GRAS), supplementation with amino acids is not. The record keeping and labeling requirements make it cumbersome to routinely supplement foods with cysteine, even though (in the opinion of the Applicant) supplementation to compensate the amount that is lost in processing would clearly be safe and healthful.

4.2.4.2 Cysteine Prodrugs

Normally, the primary source of cysteine is dietary protein, but in some cases it is desirable to supply more cysteine than can reasonably be supplied through the consumption of foodstuffs. Prodrugs for cysteine are compounds that are converted to cysteine via metabolism in the body, some of which can be safely administered in high quantities. For example, the standard treatment for acetaminophen (Tylenol) poisoning (which causes severe glutathione depletion) is the oral administration of N-acetylcysteine (NAC) (BMCCC6:155). Of necessity, the NAC dosage is high (an initial dose of 140 mg/kg of body weight (e.g. 9800 mg for a 70 kg person), followed by 17 doses of 70 mg/kg every 4 hours). The low toxicity of NAC, combined with its rapid conversion to cysteine (which in turn is rapidly converted to glutathione inside liver cells) is important for this application.

4.2.5 Cysteine and Cystine Participate in Thiol-Disulfide Exchange Reactions

Thiol-disulfide exchange reactions are a unique feature of organosulfur chemistry that provide a rapid, reversible, energy-neutral, highly specific covalent reaction for the bonding together (or the separating) of molecules that incorporate a thiol or a disulfide bond (QP551.T6913:54, QD305.S3C48:633).

The Applicant notes that more properly, this type of reaction should have been named the "thiolate-disulfide exchange reaction", because it always involves the ionized version of the thiol (RS$^-$). If the disulfide is represented as R'SSR" the exchange is as follows:

RS$^-$+R'SSR"<->R'S$^-$+RSSR" (or alternatively R"S$^-$+ R'SR)

In this reaction, the ion and the disulfide form a temporary complex with three inter-reacting sulfur atoms (and an electron), which soon separates with the resulting thiolate ion coming from any of the three thiyl radicals and the remaining disulfide molecule consisting of the other two thiyl radicals.

Thiol-disulfide exchange reactions are a form "redox" reactions, because the R'S moiety of the disulfide becomes reduced (to a thiolate ion) at the same time that the original thiolate ion (RS$^-$) becomes an oxidized moiety within the new disulfide RSSR". In other words, the original thiolate ion served as an antioxidant, becoming oxidized in the process.

Like other thiol anions, the ionized form of cysteine (CyS$^-$), will readily participate in thiol-dislufide exchange reactions with disulfides (oxidized thiols), reducing half of the disulfide in the process (QP552.G58G54:73). The resulting oxidized cysteine (either CySSCy or CySSR depending on whether the other reactant contained cysteine) can it turn react with other thiol anions (R'S$^-$) in further exchange reactions, becoming either CySSR' or CyS$^-$ depending on the nature of the other reactant and how they separate.

Of course, this brief description is somewhat of an oversimplification. Exchange reactions can be subject to steric constraints. And the products of the reaction depend on the relative redox potentials of the three thiyl radicals involved. But typically, the reaction is rapid and the product mix is random, resulting in the formation of every possible mixed disulfide (and every possible thiolate ion).

Thiol-disulfide reactions are important in the formation of the Cysteine to Cysteine bridges within proteins that help determine and stabilize the tertiary structure of the protein. They also are involved in the formation of Cysteine to Cysteine cross-links between proteins.

Many enzymes have an "SH" group at their active site (BIJ63:514), and their activity depends on whether this remains an exposed thiol (or an exposed thiolate ion), with the enzyme typically less active if the thiol is "blocked" by an attached thiyl radical. This leads to the "redox regulation" of enzymes, which is an important mechanism for regulation, signaling, and control. Note that the inactivation of the enzyme is non-destructive, because a new thiol-disulfide exchange reaction between the blocked site and any thiolate ion that happens to float by can result in a disulfide floating away (leaving the SH group on the enzyme as a thiolate ion), thereby activating the enzyme again.

The majority of the organosulfur compounds that are discussed within the present patent application are thiols or disulfides, so exchange reactions are very relevant to their associated chemistry.

4.3 Glutathione, the Mother of all Antioxidants

Glutathione is a tripeptide composed of the amino acids glutamic acid, cysteine, and glycine. An advantage of glutathione for the storage and transport of cysteine is that it is far less toxic than cysteine at high concentrations (QP552.G58G54:57). Due to the available SH group of the cysteine, glutathione is a biothiol and shares the antioxidant properties that are common to thiols. But there are also various enzymes that specifically utilize glutathione, giving it some unique antioxidant (and oxidant) properties as well.

Glutathione has a high concentration (1-5 mM) in the aqueous environments of most cells and organelles (e.g. in the cytoplasm and inside mitochondria). Glutathione does not pass freely through lipid membranes, but transport systems allow its constituent amino acids to enter cells (and organelles) and also allow GSSG, other glutathione conjugates (GS-X), and in some cases reduced glutathione (GSH) to be excreted from cells.

Glutathione has a broad diversity of functions in biological systems (too many to do justice to here, see the many examples throughout this application). An extensive treatise on glutathione is available (ARB52:711).

4.3.1 The Antioxidant and Oxidant Properties of Glutathione

Like other thiols, reduced glutathione (GS$^-$, or GSH) will readily donate the electron (or the hydrogen atom) of its SH group, even to relatively weak oxidants. For example, reduced glutathione can react non-enzymatically to reduce $H_2O_2$ and other hydroperoxides, scavenge $*O_2$ (superoxide) radicals, and detoxify other reactive oxygen species (ROS). The conventional view is that this is via electron or hydrogen atom donation, resulting in the formation of the glutathiyl free radical (GS*). Examples of the formation of GS* from the non-enzymatic reduction of a wide variety of ROS are common in the literature (e.g. QD305:S3S14:289). The formation of GS* radicals from a large variety of antioxidant activities of GSH and the fate of these GS* radicals is explored in depth in QP552.G58G566:43. The newly formed free radical is usually a weaker oxidant than the original oxidant and tends to be short lived because it rapidly dimerizes to form oxidized glutathione (GSSG).

Further analysis has shown that the dimerization of GS* to GSSG can not be by simple conjugation because in normal biological systems the concentration of GS* is always low compared to the concentration of other possible reactants. In other words, before a newly formed GS* can encounter another GS* it will encounter a variety of other molecules that it can readily react with. Given the observed preferential formation of GSSG, the probable reaction paths have been investigated (QP552.G58G566:43, QD305.S3S14:289). In the absence of oxygen, GS* will react readily with the GS$^-$ molecules that are readily available. This conjugation of GS* with GS$^-$ produces GSSG*$^-$ which is a powerful reductant. The formation of a powerful reductant from even a mild oxidant has been described as a "molecular switch" that is central to the biological response to oxidative stress. In the presence of oxygen, GSSG*$^-$ rapidly reacts with $O_2$ to form superoxide (*$O_2$) and GSSG. Alternatively, the GS* free radical can react directly with $O_2$ to form GSOO* (another free radical). Further reactions of the GSOO* with (for example) GSH produce products such as GSO* and GSOH (a sulfenic acid) along with the formation of GSSG (QD305.S3S14:289).

In any case, despite some controversy about the path from GSH to GSSG, GSH has been clearly shown to be an effective (and essential) antioxidant in almost all life forms, so the potentially damaging reaction products just discussed must either not form in vivo, or they are effectively managed and have a negligible effect.

Unlike most other thiols, there are a variety of enzymes that are specific to glutathione that augment the antioxidant (and oxidant) activity of glutathione and, indirectly, the other intracellular antioxidants.

Glutathione's antioxidant properties are augmented by various GSH-peroxidase enzymes that use GSH to reduce peroxides (e.g. hydrogen peroxide), producing GSSG in the process, which in turn is reduced back to 2 GSH by GSH-reductase (ARB52:711). Glutathione transferases (see below) also have peroxidase activity.

Glutathione (GSH) serves as a critical antioxidant and is perhaps the only molecular antioxidant whose total depletion can directly cause death (RB170.O96:101). The central antioxidant role of glutathione is due to its ability, via the "antioxidant network" (QP772.A8:139, FIG. 9.2), to recycle almost all other antioxidants to their reduced state. Therefore, insufficient GSH can also result in the accumulated oxidation of the various other antioxidants.

Glutathione has two major roles in the antioxidant network (See FIG. 1, derived from FIG. 9.2 of QP722.A8A586:133), the first of which is the participation in a sequence of oxidation/reduction reactions originating with a pre-existing oxidized molecule within the lipid membrane (R*). This molecule can oxidize vitamin E, becoming reduced in the process. The oxidized vitamin E (tocopheroxyl radical) may then oxidize an ascorbate molecule (vitamin C), becoming reduced in the process. The newly oxidized vitamin C (ascorbyl radical) is less reactive than the original oxidant. The oxidized vitamin C can in turn oxidize a GSH molecule, becoming a reduced (ascorbate) molecule again (FRBM20:543). The oxidized GSH molecule (GS*) is rapidly dimerized to GSSG. Hence the original oxidant has caused the formation of a relatively non-reactive GSSG molecule, with vitamins E and C being used (and recycled) in the process. This series of reactions can proceed non-enzymatically, although there are also enzymes available which can accelerate some of the steps (e.g. thiol transferases).

The second major role is more specific to glutathione. The GSSG that has been produced can in turn be recycled to 2 GSH by the enzyme glutathione reductase. This enzyme uses NADPH+H$^+$ as a reductant, producing NADP$^+$ which is typically recycled back to NADPH as part of the pentose pathway of energy metabolism. Various other antioxidants can serve as intermediates in an oxidation/reduction pathway, still leading to the formation of oxidized glutathione (GSSG) and its ultimate reduction by NADPH. The net effect is that the energy input (e.g. from glucose) drives the reduction of GSSG, which in turn drives the reduction of the other antioxidants that participate in the antioxidant network. Therefore, glutathione serves as a critical link between the "non-enzymatic" antioxidants and the cellular energetics which ultimately drives the system. (Vitamin C can serve a similar role, because there are specific enzymes that utilize NADPH for its reduction too.)

Interestingly, vitamin C has been shown to be able to pass through the cellular membrane of red blood cells and to thereby couple the intracellular antioxidant network to the external environment (JCI63:53). The uptake of oxidized vitamin C (DHA) is active via the glucose transporter in the cell membrane and can operate against a concentration gradient, while the reduced vitamin C (ascorbate) diffuses from the cell through the cell membrane back to the extracellular environment (FRBM24:789). The capacity for this "ascorbate cycling" by red blood cells is substantial (plasma vitamin C can be completely recycled in 3 minutes). The recycled ascorbate also protects the vitamin E in LDL from oxidizing (FRBM24:789).

Another example of the ability of the glutathione reductase driven antioxidant system to convert disulfides to thiols is illustrated in FIG. 2. In this illustration the compound SAMC (consisting of the mixed disulfide between allyl mercaptan and cysteine) is taken into the cell by a trans-membrane transport protein. Within the cell, the SAMC is exposed to a large concentration of glutathione, approximately 3% of which is in the form of the reduced anion (GS$^-$) which will readily participate in a thiol-disulfide exchange reaction. The resulting products depend on how the reaction complex splits up, producing either AS$^-$+CySSG or CyS$^-$+ASSG. Further exchange reactions with the GS$^-$ ions eventually produce an oxidized glutathione molecule (GSSG) which is then rapidly reduced to 2 GSH by glutathione reductase. This produces a net decrease in the total disulfide concentration and a net increase in the total thiol concentration (which up to now have remained constant). Over time, the combination of random exchange reactions and the action of glutathione reductase will drive the disulfide concentration down to almost zero and the net products from the original SAMC will be the thiols allyl mercaptan and cysteine.

The cell maintains a low concentration of glutathione disulfide (GSSG), the oxidant properties of which are augmented by the enzyme Protein Disulfide Isomerase (PDI), which accelerates the formation of intramolecular disulfide bonds, using GSSG as the proximate oxidant (QP552.G58F585:125). Other essential oxidant properties of glutathione include its redox regulatory roles, including the control of proteins and enzymes via glutathonylation (the S-thiolation of exposed thiols on proteins) (BBRC242:1).

4.3.2 The Detoxification Properties of Glutathione

Glutathione is also necessary for the detoxification of a wide variety of toxic substances (ARB52:711), including pesticides, herbicides, pollutants, and industrial solvents. As a biothiol, it shares the various detoxification properties of biothiols, including the formation of complexes with metals that would otherwise be more toxic (e.g. mercury, the ability of which to be captured by thiols was observed by alchemists, hence the name "mercaptan" for various thiols). But there are also various glutathione specific enzymes, especially the glutathione transferases, which greatly enhance the detoxification properties of glutathione.

4.3.2.1 Glutathone Transferases

The GSH-transferase enzymes (GST) bind electrophilic substances to glutathione molecules, which are then excreted from the cell (and ultimately from the body). In some instances an electrophilic center was previously introduced by another reaction, such as those catalyzed by the cytochrome P-450 "phase I detoxification" enzymes. The subsequent conjugation of the now electroplilic molecule to glutathione is "phase II" of the detoxification system.

The resulting conjugate may also be toxic, but it can be more readily excreted than the original molecule. This is especially the case for hydrophobic compounds (which could otherwise accumulate in cells) because the conjugates, being water soluble, are more easily transported to the liver and kidneys by the circulatory system.

There are various GST enzymes which vary in their preferred substrates, although each GST typically will have low substrate specificity. The GST enzymes are induced as necessary. In practice, this means that the prior exposure to a low level of a toxin will induce the production of the appropriate GST and the tolerance for a repeated exposure to that toxin will be increased. Because of the broad specificity of GSTs, this will also provide protection from other (sometimes seemingly unrelated) compounds. For example, various organosulfur compounds from garlic and onions have been shown to increase GST activity sufficiently to provide protection from the carcinogen benzo[a]pyrene, reducing the tumor incidence in mice to as low as 14% of the control (CG9:131).

Glutathione is also a required coenzyme for other detoxification processes, including the methylation of arsenic. Insufficient GSH (e.g. from depletion due to alcohol consumption) is responsible for acetaminophen (Tylenol) toxicity, which is the second largest class of toxic drug ingestions in the United States (BMCCC6:155).

Because exposure to toxins is normally rare, people with glutathione deficiency can seem well nourished and healthy (until exposed to a toxic substance). However, some populations are continuously exposed to toxins, resulting in chronic health problems if there is concurrent glutathione deficiency. For example, in regions where the drinking water is arsenic contaminated, toxicity has been shown to correlate positively with low consumption of animal protein (EHP112:1104). Animal protein is typically the most significant dietary source for cysteine (the limiting amino acid for glutathione synthesis) so these people are more likely to be glutathione deficient.

4.3.2.2 The GS-X Pump Excretes Glutathione Conjugates from Cells

Cell membranes use a special transport system (the "GS-X pump", also known as "MRP" proteins, of which there are several types in humans) that can excrete via exocytosis (QP606.G59G59:199) any glutathione conjugate with a molecular weight over ~350 (GSH itself has an MW of 307). This constitutes the "phase III" of the detoxification system. Glutathione chelate complexes of metals (e.g. arsenic) are also excreted by the GS-X pump. The GS-X pump has been extensively studied due to its role in the detoxification of various anti-tumor chemotheraputic drugs, such as Cisplatin, thereby reducing their effectiveness (QP606.G59G59:199). Tumor cells with increased expression of the GS-X pump are termed "multidrug resistant".

The GS-X pumps are members of the "ATP-Binding Cassette" (ABC) class of membrane transport proteins that include hundreds of members that selectively transport ions or other small molecules in or out of cells, organelles, vesicles, and microsomes. Typically, the ABC transport proteins have two bundles of six helices each, connected by a flexible domain that includes an ATP binding site and terminating in a second domain that includes a second ATP binding site. One (or both) of the bundles of helices has an interior channel that provides selective passage for the appropriate molecules. However, it is not clear how the glutathione conjugates are selectively passed through the GS-X pump, both because of their variability and because of their large size.

Experiments utilizing a fluorescent glutathione conjugate molecule (GSH-bimane) have shown via microphotography that the conjugates can accumulate within intracellular vesicles that then move to the plasma membrane and fuse to the plasma membrane (QP606.G59.G59:199). This results in the contents of the vesicle being released to the outside of the cell and the GS-X transporters that were in the vesicle membrane becoming part of the cell's plasma membrane.

4.3.3 Variability in Glutathione Levels

Various factors have been found to modify the localization and concentration of glutathione within organisms.

4.3.3.1 Dietary Sources of Glutathione

Glutathione in food varies dramatically, such that well fed Americans can have a 40:1 range in its consumption (JFCA2: 327). However, dietary glutathione probably has no special significance other than as a source of cysteine. The glutathione inside cells is created from its constituent amino acids (glutamate, cysteine, and glycine). Of these, cysteine is almost always the limiting amino acid, because glutamate and glycine are relatively common in foods.

Some dietary ingredients have been shown to augment glutathione. For example, dietary garlic or onion powder has been shown to increase the liver glutathione level in chickens by 40% (RM666.G15K6313, page 190). Consumption of garlic produces an increase in the reduced glutathione level, which was attributed to its increasing the activity of the GSH reductase enzyme by up to 87% (RM666.G15K6313, page 190), thereby increasing the proportion of GSH to GSSG. The administration of SAMC has been shown to significantly increase the total glutathione level of cells (CR61:725), which was attributed to the induction of the GSH synthesis enzymes.

4.3.3.2 Unbalanced or Excessive Vitamin Consumption

Although vitamin C and glutathione in many ways work together and at low doses vitamin C can partially substitute for glutathione, excessive vitamin C consumption has been shown to significantly decrease the glutathione content of cells. This effect has been utilized in a clicinal trial where the goal was to increase the cytotoxicity of the chemotherapeutic drug arsenic trioxide (which is normally detoxified by glutathione within cells) against the cancer multiple myeloma (CCR8:3658). A daily dosage of 1000 mg of vitamin C caused significant glutathione depletion, resulting in a mean percentage decrease of 60% among the patients.

Vitamin A and other carotenoids can also cause depletion of glutathione and other thiols. The main antioxidant property of the carotenoids is the quenching of singlet oxygen, with each carotenoid molecule able to do this approximately 1000 times before it breaks down and forms a very reactive aldehyde molecule. These break down products form adducts with SH groups that are not reversible. Carotenoid breakdown products are otherwise long lived and can travel far before they encounter (for example) an SH sensitive enzyme, producing a cumulative inhibition of SH enzymes in the body. Carotenoid levels, especially beta-carotene in blood and various tissues are dependent on the carotenoid content of food and may exceed the levels that were used in these enzyme inhibition studies (RB170.H36:235).

This apparently little-known toxicity may explain the poor results from the "beta-Carotene and Retinol Efficacy Trial", which showed that carotenoid supplementation significantly increases cancer risk and overall mortality (CBEP12:350). A detailed post-analysis revealed that the carotenoid consumption of the people in the "intervention arm" of the placebo controlled trial completely eliminated the beneficial effects of fruit and vegetable consumption.

Only the people in the "placebo arm" of showed a lowered cancer risk related to fruit and vegetable consumption. Interestingly, Table 2 of this report shows that high "Total fruits" consumption resulted in a lower relative risk factor (0.56) than that of any individual category of fruits (which had a range of 0.63-0.73). In the opinion of the Applicant, this indicate either that a broad mix of fruits is necessary, or that there is some "magic bullet" fruit that is included in the "total fruit" category but not in the more specific sub-categories.

It is also interesting that the high consumption of vegetables in the "Other vegetables" category (which includes onions and presumably garlic) resulted in a lower relative risk factor (0.56) than that of "Total vegetables" (0.82). Among the individual categories of vegetables, the Cruciferae produced the lowest relative risk factor (0.68) than that of any other individual category of vegetables (which had a range of 0.80 to 1.38) (CBEP12:350).

4.3.3.3 Glutathione Synthesis

Glutathione is synthesized in two stages. First the enzyme gamma-glutamyl-cysteine synthase combines glutamate with cysteine (producing a gamma-glutamyl linkage instead of the peptide linkage that is used for other dipeptides). The resulting molecule of gamma-glutamyl-cysteine is then combined with glycine by the enzyme glutathione synthase to produce the molecule of glutathione (QP514.M45:101).

Each of these steps utilizes a molecule of ATP for energy and therefore two molecules of ADP are produced. Interestingly, both steps are reversible, indicating that the breakdown of glutathione back to its constituent amino acids can convert 2 ADP to 2 ATP in the process (QP514.M45:101).

The rate of glutathione synthesis is generally considered to be limited by the first step, either due to low availability of cysteine or due to feedback inhibition based on the level of glutathione (GSH) (QP514.M45:101). This enzyme actually has its activity lowered by GSH and increased by GSSG (the opposite of mote SH sensitive enzymes), indicating that there is an exposed SH group that must be blocked for higher enzyme activity.

After loss of glutathione due to the trauma of surgery (AJPEM275:E359), the rate of the second step (glutathione synthase) can be limiting, and the low glutathione level can persist for a long time. In this case, the administration of glutamate can speed the recovery to normal glutathione levels.

4.3.4 Augmentation of Intracellular Glutathione 4.3.4.1 Cysteine Prodrugs

In the case where cysteine availability is limiting, augmentation of the cysteine level will allow the increased synthesis of glutathione. Several methods for this were presented in section 4.2.4.2.

SAMC is another compound that has been studied as a means to deliver cysteine and increase glutathione levels. In vitro experiments show that when cells are administered SAMC (which contains a cysteinyl radical that can easily be converted to cysteine in vivo, e.g. by a thiol-disulfide exchange reaction with a thiolate ion. The result is a significant increases the total glutathione level of cells (CR61:725).

4.3.4.2 Compounds that Bypass Gamma-Glutamyl-Cysteine Synthase

Because the first step in glutathione synthesis is usually the limiting one (either due to cysteine availability or due to feedback inhibition of the enzyme), bypassing this step through the administration of gamma-glutamyl-cysteine or a prodrug for this compound can raise the glutathione level beyond that which would be normally present in the cell. The administration of the compound gamma-glutamylcysteinyl-ethyl ester has been found to be an effective, non-toxic way to do this (BBA1313:47).

4.3.4.3 Whey Protein

A particularly good source of cysteine is whey protein, which is sold as a dietary supplement. Whey Protein consumption has been shown to increase glutathione levels, with a wide variety of associated health benefits. It has also been claimed that the undenatured cystine in whey protein is more bioavailable than other dietary sources of cysteine (US005451412A).

While whey protein is an excellent source of cysteine, its bioavailable cysteine is reported to be very sensitive to denaturation from heat or mechanical shock, requiring a microfiltration process to be used during its manufacture. If not prevented, this denaturation causes a significant decrease in the ability of whey protein to raise the glutathione level of the host. Even the transport by un-refrigerated truck can possibly cause this damage (US005451412A).

4.3.5 Glutathione Depletion
4.3.5.1 Glutathione Synthesis Inhibitors

The glutathione level within cells can be intentionally lowered through the use inhibitors of its synthesis, such as BSO (Blood93:268). This can be useful in experiments, for example to demonstrate that some cellular process is glutathione dependent. The depletion of glutathione also has clinical application as a means to increase the cellular toxicity of chemotherapeutic agents in the treatment of cancer.

4.3.5.1.1 Extreme Glutathione Depletion Kills Animals (and Cells)

Experimentally, by inhibiting glutathione synthesis, it has been shown that glutathione depleted animals die within a few days (RB170.O96:101). Some types of cancer cells are naturally low in glutathione and can be selectively killed by further lowering their glutathione level (CCR8:3658).

4.3.5.2 Lifestyle Choices

Activities such as smoking, drinking alcohol, and excessive exercise cause glutathione depletion. Improperly balanced vegetarian or other "healthy" diets can result in a low glutathione level if an inadequate amount sulfur amino acids are being consumed.

4.3.5.3 Glutathione Excretion

The formation (and elimination) of glutathione conjugates (GS-X) leads to their excretion from the cell (QP606.G59G59:199), which can deplete cellular glutathione in the process. The glutathione conjugates can either be produced by the glutathione transferase proteins (GSTs) or by normal oxidation of GSH to GSSG (its antioxidant function), especially in situations where glutathione reductase has been inhibited.

4.3.5.3.1 Depletion due to Acetaminophen can be Fatal

The second largest cause of drug-induced death in the US is the ingestion of acetaminophen (Tylenol). Even the recommended dosage can be fatal to people whose glutathione level is low, such as alcoholics (BMCCC6:155). The depletion is due to the metabolism of the drug, which produces a glutathione conjugate that is excreted from cells. This can cause fatal liver damage if the liver cell glutathione level becomes significantly depleted.

4.4 Medicinal Benefits of Dietary Thiols, Disulfides, and Thiosulfinates

The vegetables of the *allium* family (garlic, onions, etc.) and of the cruciferae family (cabbage, broccoli, brussels sprouts, etc.) are perhaps the only dietary source for thiosulfinates, and can also be a major source for thiols and disulfides. Of these, the medicinal properties of the alliums (garlic and onions) have been the most extensively researched. They are known to have various medicinal, toxic, and anti-social properties, which will now be reviewed in order to establish their strengths and weaknesses in relation to the present invention.

Traditional medicine has yielded a vast number of compositions containing garlic and/or onions for the treatment of a wide variety of conditions (EPMR6:56, EPMR6:115, IJEB34:634, ISBN9679786846:15). Medicinal uses include the prevention and treatment of diseases related to the heart and circulatory system, microbial infections, cancer, respiratory diseases, hypoglycemia, and as a detoxicant for heavy metal poisoning and other toxins (RM666.G15K6313, pages 135-211).

In the prevention of bacterial infections, alliums (e.g. garlic) are unique as an antibiotic because they simultaneously produce a pro-biotic response, encouraging the maintenance of a healthy intestinal flora. At the same time that garlic inhibits the "bad" bacteria (streptococci, coliforms, *e. coli*, salmonellae) by a large factor (100×) it inhibits the "good" lactobacteria by a much lower amount (10×) (FM29:348). The result is that enough good bacteria are maintained to aid in digestion and vitamin formation, while suppressing the bad bacteria. Another interesting aspect is the apparent inability of most bacteria to develop resistance to garlic (MI2:125), although apparently the "good" bacteria have evolved a tolerance.

In addition to disease prevention, garlic and other alliums have been used to provide general health benefits such as antioxidant protection, strengthened immune system, anti-hepitoxic protection, anti-inflammatory protection, improved digestion, and for repelling insects (RM666.G15K6313, pages 135-211).

Within the last two decades, there have been various significant discoveries relating to the importance of nitric oxide (NO) in biological systems. Nitric oxide and its metabolites have been shown to play a significant role in the circulatory and immune systems, to regulate enzyme activation/deactivation, and to act as oxidants and antioxidants. Several of the health benefits from garlic are related to its interactions with nitric oxide in vivo. For example, garlic has been shown to increase the activity of the eNOS enzyme that synthesizes the nitric oxide that dilates blood vessels, thereby promoting good blood flow (BST23:S136). Interestingly, garlic simultaneously decreases the activity of the iNOS enzyme that synthesizes the nitric oxide that damages tissue during an immune response, thereby reducing chronic inflammation (BST23:S136).

Daily garlic consumption has been associated with health maintenance and is recommended for successful aging (E185.96.D368:107). Literally, thousands of scientific articles have been published on garlic, allicin, and other garlic derived compounds, with 2240 references listed in RM666.G15K6313, pages 235-319.

Hundreds of animal studies have been performed with many clearly demonstrating beneficial effects from the consumption of garlic, allicin, or garlic derived compounds, as illustrated by the following examples.

When rats are fed a high fructose diet, they tend to gain weight significantly. In an experiment of 5 weeks duration that fed a high fructose diet to rats (AJH16:1053), for the first 3 weeks both the control and experimental groups had a weight gain of approximately 10%. For the remaining 2 weeks the control group continued to gain another 10% in weight, but the group that was also fed allicin (8 mg/kg) had a 3% loss in weight (despite continuing to eat all the food). While these results are impressive, their utility is limited because a comparable dosage for a typical 70 kg human adult would be 560 mg of allicin, or 56 cloves of raw garlic per day.

In addition to causing weight gain, a high fructose diet causes rats to become hyperinsulinemic, hyperlipidemic, and hypertensive. In an experiment (AJH14:377) that was nearly identical to the previous one, at the end of 5 weeks the rats that were also fed allicin (8 mg/kg) during the final 2 weeks had a significantly smaller percentage increases than the control group in insulin (+62% versus +252%), triglycerides (+6.8% versus +113%), and blood pressure (+5.2% versus +13.5%). Again, the dosage was equivalent to 56 cloves of garlic/day in humans.

Another experiment shows that an oil extract of garlic (primarily DADS) could exhibit an estrogenic property (i.e. mimic the hormone) in ovariectomized rats (PHYRES18:389). A dosage of 100 mg/kg eliminated the weight gain and substantially reduced the loss of bone density and the changes in urinary and serum parameters that were seen in the control group. Again, the dosage utilized (equivalent to hundreds of cloves of garlic per day for a person) limits the utility of these results.

4.4.1 Allicin—The Primary Thiosulfinate Derived Garlic

The first medicinal property of garlic to be studied with modern scientific methods was its antibacterial action (JACS66:1950). The active ingredient was isolated and given the name allicin.

The chemical structure of allicin was determined to be (JACS66:1952):

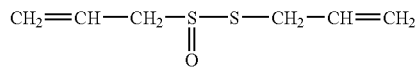

Numerous allicin derived organosulfur compounds have also been found to provide medicinal benefits; however, the benefits attributed to allicin tend to be the superset of these, in part because many of these compounds produce similar metabolites in vivo (PM59:A688).

Allicin is a thiosulfinate, with the R and R' radicals being allyl groups in the following formula:

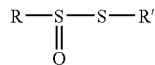

Other thiosulfinates have been found to also provide medicinal benefits, such as the anti-tumor properties of methyl methane thiosulfinate (R and R' being methyl groups), a compound formed by the crushing of onions or garlic, and a metabolite of the cruciferae vegitables (cabbage, broccoli, etc.) (FCT33:537). However, the sulfur content of other common fruits and vegetables is at most 25% that of garlic (onions and broccoli contain this amount (RM666.G15K6313, page 39)), so in the context of this invention garlic is the model dietary source of thiosulfinates and other *allium* derived compounds.

The extremely high permeability of biological membranes to allicin also contributes to its biological activity (BBA1463:20).

Not surprisingly, allicin has a garlic-like taste and odor and burns the mouth and gut if consumed directly (unless it is heavily diluted).

4.4.1.1 Allicin is a Broad Spectrum Anti-Microbial Agent that is Effective in Preventing Infections, Including the Common Cold Allicin has been shown to be a broad spectrum antimicrobial agent that significantly inhibits many strains of bacteria, fungi, viruses, and parasites (MI2:125). It has even been shown to be effective in the prevention and treatment of the common cold (AIT15:189), reducing the incidence of infection during the clinical trial (only 24 vs. 65 for the placebo group), and reducing the duration of symptoms to an average of 1.5 days (vs. 5 days for the placebo group).

In a comparison of the effectiveness of 13 types of antibiotics against 13 types of bacteria, Garlic and Chloramphenicol tied as the most effective antibiotics (inhibiting 12/13 of the species), and they also had the highest activity (average zone of inhibition of 20 mm) (IJEB15:466). Interestingly, the one type of bacteria that garlic was not effective against (*Ps. Aeruginosa*) was not inhibited by any of the other antibiotics either.

The mechanism of antimicrobial action was initially proposed to be due to allicin's reaction with cysteine (JACS66:1952), eliminating the free SH groups essential to bacterial roliferation. Allicin was subsequently shown to be a very potent inhibitor of "SH-enzymes" (BIJ63:514). This model for its mode of action is still commonly accepted (MI2:125) and is well supported by experimental evidence. For example, the activity of the well-known sulfhydryl-dependent enzyme papain was shown to be rapidly inhibited to 1% of its initial activity by allicin and to rapidly be completely restored by an SH-reducing agent (BBA1379:233).

But there is some question whether enzyme inhibition by allicin is universally due to sulfhydryl blocking. An investigation of the inhibition of acetyl-CoA synthase that compared the effect of allicin with that of another well known thiol-group blocker of acetyl-CoA synthase (p-hydroxymercuribenzoate) found that allicin was unexplainably effective (FEBS261:106). Their conclusion was that allicin must be a specific inhibitor of acetyl-CoA synthase.

In another example, allicin has been shown to reduce the rate of bacterial RNA synthesis to below 1% of that of control cells. The effect on RNA synthesis was so dramatic that the authors suggested that allicin was acting not as a general inhibitor of sulfhydryl-dependent enzymes but rather as a specific inhibitor of RNA synthesis (AAC32:1763).

Other thiosulfinates have been shown to have similar antimicrobial properties, such as methyl methane thiosulfinate (R and R' methyl) and methyl allyl thiosulfinate (R methyl and R' allyl), which have been shown to be effective against E-coli O157:H7 (BBBIO65:966). Tests comparing the activity of 8 types of thiosulfinates against 25 types of bacteria and fungi found that they were all active, with the lower molecular weight compounds (2, 4, and 6 carbons) being most effective against the gram-negative bacteria and the longer carbon chain compounds more active against gram-positive bacteria (JACS69:1710), which the authors attribute to the increased lipid solubility of molecules with longer carbon chains.

Branched compounds were active, but less so than the unbranched compounds, which was attributed to the better ability of smaller molecules to gain access to the critical —SH groups of enzymes.

4.4.2 Garlic and Allicin have Powerful Antioxidant and Oxidant Properties

Studies of garlic, allicin and other *allium* derived compounds have shown both antioxidant and oxidant activity.

The sulfur atom (and the sulfur atoms in molecules containing sulfur) can have oxidation states in the range of −2 to +6. Therefore, sulfur can participate in a wide variety of redox reactions. A table of the oxidation states of sulfur compounds (QP801.G6C6:4) shows the oxidation states of the various sulfur compounds that are relevant to the present invention, including RSH (−2), RSR' (−2), RSSR' (−1), RSOH (0), RSOSR' (0), and RS(O)SR' (0). From this list, it can be seen that the thiol (RSH) has the lowest oxidation state, the disulfide (RSSR') is more oxidized, and the thiosulfinate (RS(O)SR') is still more oxidized.

In a study of the suppression of LDL oxidation by garlic derived compounds (JN131:985S), S-allylcysteine, N-acetyl-S-allylcysteine, alliin, and especially S-AllylMercaptoCysteine (SAMC) were shown to significantly reduce $Cu^{2+}$ induced LDL oxidation, but allicin increased the LDL oxidation to almost 3× the level of the control.

In a study of the total antioxidant capacity of 22 vegetables measuring the reduction of peroxyl radicals (*OOH), hydroxyl radicals (*OH), and of $Cu^{2+}$ catalyzed free-radical chain reactions, garlic homogenate rated a "total antioxidant score" of 23.2 (second only to kale), approximately 3 times the average, showing that garlic is an excellent antioxidant (JAFC44:3426). Interestingly, the garlic homogenate showed significant antioxidant capacity against $Cu^{2+}$ induced oxidation (contrary to the effect of allicin alone, as reported in JN131:985S), which implies that additional compounds in the garlic homogenate were active.

In a chemiluminescense assay of the antioxidant properties of eight commercial garlic products, only "AGE" (Aged Garlic Extract, a garlic supplement product from Kyolic Research) had net antioxidant activity (JN131:1010S). The AGE product contains primarily the water-soluble compound S-allylcysteine (SAC), but it also contains S-AllylMercapto-Cysteine (SAMC) and the lipid-soluble compounds diallyl sulfide, diallyl disulfide (DADS) and diallyl trisulfide. The other products tested all contained garlic powder, produced allicin upon ingestion, and were not effective as antioxidants.

In another study comparing the constituents of AGE with garlic extract, a chemiluminescense assay showed raw or heated garlic extract to be pro-oxidant, but AGE to be a potent antioxidant (PM60:417). Of the 11 various organosulfur components derived from garlic that were analyzed, SAMC and glutathione were shown to be the most effective antioxidants (by approximately a factor of two, compared to the other compounds).

But AGE can also induce oxidant activity because it contains protein F4 from garlic which is an immunostimulant that can cause inflammation (JN131:1067S). In this case, the oxidants are produced in vivo by the immune system itself, which is why they don't show up in other in vitro experiments utilizing AGE.

Garlic extract (crushed fresh garlic in water) at a moderate dosage (25 mg/kg, corresponding to 0.05 mg/kg of allicin) has been shown to significantly protect against chromosomal aberrations induced by mutagenic agent cyclophosphamide (CL176:31) without introducing any significant chromosomal damage in the controls. But a more extended study (sampling at 6 hr, 12 hr, 18 hr, 24 hr, 7 days, 30 days and 60 days) has shown that the garlic extract itself can introduce chromosomal damage, especially at higher doses (50 or 100 mg/kg). Interestingly, although some chromosomal damage appeared for a few days at the lowest dosage tested (25 mg/kg), after 30 days there was no significant difference in chromosomal damage relative to the controls (FST34:43).

A skeptical study on the antioxidant properties of allicin and several other thiosulfinates (JAFC50:2488), after noting that many other investigators have attributed antioxidant effects to thiosulfinates (e.g. BBA1379:233), proceeded to test these thiosulfinates against $*O_2^-$ (superoxide radical), $H_2O_2$ (hydrogen peroxide), $O_2^1$ (singlet oxygen), *OH (hydroxyl radicals). The study found no significant antioxidant activity other than the ability to scavenge *OH (a somewhat meaningless result in itself because almost all organic molecules can scavenge *OH).

Another study (MCB148:183) on the ability of garlic powder to scavenge *OH also shows (although not noted by the authors) that high concentrations of garlic powder actually increase the level of *OH in their control group (which had garlic powder administered to them but no added *OH).

Pretreatment with SAMC has been shown to protect mice from acetaminophen (Tylenol) poisoning, by suppressing the reduction in hepatic glutathione level after acetaminophen administration (PHYRES3:50). Post treatment with a single dose of SAMC (200 mg/kg) shortly after exposure to acetaminophen is also protective in mice (EJP433:177). Similar results were obtained in PHYRES3:50, which shows that SAMC is much more effective than the other garlic derived compounds contained in the "AGE" (Aged Garlic Extract) dietary supplement.

An extensive review, titled "Garlic as an Antioxidant: The Good, The Bad and The Ugly" (PHYRES17:97), illustrates the diversity of reported antioxidant, oxidant, and paradoxical effects, including a reversal of antioxidant effect with an increasing dose of raw garlic homogenate.

Another summary of the antioxidant effects of allicin and related compounds (RM666.G15K6313:190) concludes that at most concentrations in vivo, allicin (generally a pro-oxidant compound) is metabolized to allyl mercaptan (a strong antioxidant), but at higher concentrations the conversion saturates and allicin displays its pro-oxidant effects.

The Applicant notes that these various studies show that the results depend on which antioxidant or pro-oxidant property is being tested, which *allium* derived compounds are being tested, the concentration, and the method of testing. From the published literature it appears that neither garlic, allicin, nor AGE is an antioxidant under all circumstances, but they have each been shown to be effective antioxidants in some circumstances.

The Applicant notes that the various short term experiments with allicin tend to show that it is an oxidant, but when the allicin is allowed to form other metabolites, antioxidant activity tends to be detected over time. These results are in agreement with the oxidation state of thiosulfinates being higher than that of disulfides, which in turn is higher than that of thiols (e.g. allyl mercaptan).

The research leading up to the co-pending application "Medicinal Products Incorporating Bound Organosulfur Groups" (US2005/0260250A1), produced new discoveries relating to the anti-oxidant mechanisms of allyl mercaptan. The cycle of extracellular antioxidant activity of allyl mercaptan, followed by the reduction DADS via exchange reactions within the cell is illustrated in FIG. 3. Allyl mercaptan can freely diffuse out of the cell and serve as an extracellular antioxidant. Then when it becomes oxidized to diallyl disulfide, the diallyl disulfide can freely diffuse into the cell and become reduced back to allyl mercaptan. In other words, the extracellular environment becomes "redox coupled" to the reductive intracellular environment via the diffusion of these molecules through the cell's plasma membrane.

Another illustration of this process and how it relates to the antioxidant network is shown on FIG. 4. It can be seen that the allyl mercaptan (AllylSH) and diallyl disulfide (DADS) form a thiol cycle that serves as an antioxidant on one side and is coupled to the glutathione based thiol cycle on the other side of the cell membrane, with the entire antioxidant environment being driven by the NADPH that is produced during energy metabolism by the pentose pathway (not shown).

4.4.2.1 More about the Antioxidant Properties of Thiols and Disulfides

In a co-pending patent application (US2005/0260250A1), the Applicant has investigated additional mechanisms by which thiols serve as antioxidants. These will be reviewed in this section (and its associated subsections) because they are pertinent to understanding the features of the present invention.

The conventional view of reactions involving oxidants and antioxidants emphasizes the role of electron transfer, with the driving force being the difference in the oxidation/reduction (redox) potentials of the reactants. In some cases, an attempt has been made to relate the redox potentials of other types of reactions to that of electron transfer reactions. However, it is important to note that there is no single "redox state of a person" or even a "redox state of a cell" but rather there coexist a number of different redox couples, the redox states of which are not necessarily linked to each other (RB170.O96:285). Even if an overall equilibrium state could be predicted from the relative oxidation/reduction potentials of the various reactants, biological subsystems are rarely in equilibrium. (True equilibrium is achieved only in death, and perhaps not even then.)

The Applicant notes that cells themselves go through a life cycle, and that after cellular division, the newly formed cells are actually young, even in an old individual. Every new cell is the descendent of its parent, therefore all young cells are derived from old ones, with the ultimate parent having been perhaps a billion cellular generations ago. Therefore, to the extent that a cell can be considered young, this is due to it being the product of a recent division. Apart from the shortening of telomeres of differentiated cells (which has no significant effect until the telomeres are substantially shortened) these "young" cells in an "old" body express their "old" characteristics in response to signaling from their environment (e.g. the total thioudisulfide concentration and the current REDST). Therefore, the parameters of the cellular environment of the typical young person can provide a target for the demonstrably safe and potentially therapeutically beneficial concentrations of thiols and disulfides to be achieved through the administration of *allium* related compounds to the host.

4.4.2.1.1 Thiol Transfer

The transfer of a thiolate group that occurs during a thiol-disulfide exchange reaction is directly analogous to the transfer of an electron that occurs during an oxidation-reduction reaction. Just as the oxidation/reduction potential determines the equilibrium state associated with electron transfer reactions, an analogous oxidation/reduction potential for a thiol-disulfide couple can determine the equilibrium state for their thiol transfer reactions (absent other effects, such as steric restrictions) (EJB2:327).

The Applicant notes that within an organism, the majority of thiolate groups are either a cysteine, a cysteinal residue on a peptide (e.g. glutathione), a cysteinal residue on a protein, or some other thiolate group (e.g. an allyl mercapto group) with behavior in exchange reactions that is similar to that of cysteine. Therefore, to a first order, the equilibrium result of exchange reactions is a nearly uniform distribution of thiols and mixed disulfides. (Note that although the rate of an exchange reaction depends on the pKa of the thiol and the local pH, this rate only affects the rate at which equilibrium is approached, not the final equilibrium point.)

Researchers have found it useful to define for the entire set of thiol <-> disulfide redox pairs within an environment a redox status (REDST) with its formula being the square of the total thiol concentration divided by the total disulfide concentration. (The squaring of the thiol concentration is due to each disulfide being formed from two thiol molecules, and how this effects the dynamics of the reaction rate.) In humans, the REDST declines with age by approximately a factor of 4 between the third and the ninth decade of life (AEMB543:191) and is a major indicator of the status of biological aging.

The utility of the REDST concept comes in part from the distribution of thiol and disulfide concentrations naturally becoming equilibrated within an environment through the action of thiol-disulfide exchange reactions. In other words, although the total concentration of thiols and the total concentration of disulfides is not changed by an exchange reaction, the probability of any thiolate group (e.g. a regulatory cysteine residue in an enzyme) being part of a mixed disulfide (i.e. being "blocked") is a shared property within an environment, and any change in REDST (e.g. from the addition of an oxidant) shifts this probability for every such thiolate group. Thus, the manipulation of the REDST is a potential mechanism to broadcast a control signal within an environment, analogous to the use of hormones within an organism.

4.4.2.1.2 Common Confusion Associated with Various Types of Redox Potentials

But, in the opinion of the Applicant, the use the term "redox" for the potential associated with the thiol-disulfide couple has led to the confusion of many researchers. This confusion manifests itself, for example, in the extension of the general observation that the cellular environment is very "reductive" (which is true, in and of itself) to the common statement that this inhibits the formation of disulfide bonds in proteins within the cellular environment (which couldn't be less true).

Even the most recent textbooks commonly make statements such as "The interiors of cells are for the most part reducing environments: they furnish electrons in the form of hydrogen atoms . . . . The chief effect of this (difference) is that cysteine residues in proteins are usually fully reduced to —SH groups inside the cell but are readily oxidized to disulfide S—S bridges when the protein is secreted" (QP551.P48:92, published in 2004).

Without further qualification, the term "reductive" is generally taken to refer to electron transfer reactions, and the cellular environment is certainly reductive in this sense. For example, the concentration of GSH, which will readily donate electrons, is typically in the range of 1-5 mM within cells (ARB52:711), while the concentration of intracellular oxidants will typically be less than 1% of this.

But thiol-disulfide reactions do not involve the reduced form of the thiol (e.g. GSH) but instead involve the ionized form (e.g: GS⁻). So the relevant concentrations for evaluating how "reductive" the environment is, in the thiol-disulfide sense, is the concentration of the ionized form. For cysteine (and hence GSH) this is approximately of $\frac{1}{30}$ the concentration of the reduced form (at a pH of 7, given that the pKa of cysteine is approximately 8.5). For the specific case of glutathione within a cell, if the concentration of GSH is 1 mM, the concentration of GS⁻ will be approximately 0.03 mM and the concentration of GSSG will be approximately 0.01 mM. (In other words, the concentrations of GS⁻ and GSSG are in the same order-of-magnitude range.) It has been shown that these concentrations are in fact nearly optimum for the formation and maintenance of the correct disulfide bonds within proteins (BICH9:5015) and that even after the denaturation of a protein, it will spontaneously adopt the proper conformation (including the formation of disulfide bonds) when exposed to these glutathione concentrations, and without requiring the involvement of any enzymes. So, instead of being "fully reduced", the cysteine residues in the proteins within cells actively participate in disulfide bonds.

The development of the proper disulfide bond formation within a protein molecule illustrates that both the formation and dissolution of disulfide bonds are part of the process of protein folding. Although an incorrect disulfide bond can easily form early in the process (e.g. between the wrong pair of cysteines), it will not be long lived, because it will tend to be under stress: If a thiolate ion drifts by, the thiol-disulfide exchange reaction will essentially always split this incorrect bridge (the separational pull will determine how the complex splits). However, once the proper conformation is achieved the disulfide bond will normally be under little stress and will not tend to be split by passing thiolate ions. This does not exclude there being multiple possible conformations for some properly functioning proteins, with each conformation possibly stabilized by dislufide bridges. In other words, "any protein disulfide bond that can be reduced by GSH . . . must be strained, or the protein conformation must change" (QP522.G58F85:205).

In summary, properly folded proteins will frequently have stable disulfide bonds formed, especially in the intracellular environment (which is the opposite of what is commonly being taught).

4.4.2.1.3 Antioxidant Effects of Thiol Transfer

In addition to forming bridges within a protein molecule (or a multi-polypeptide complex), disulfide bonds can provide structure and strength between proteins (and between other types of structural molecules within an organism). For example, hair and nails obtain their strength from richly interconnected disulfide bonds ("links") between proteins (e.g. keratins). Interestingly, the formation of a "permanent wave" involves the introduction of stress to hairs (by rolling them on curlers) then applying a reducing agent (so allow the stressed links split), then the formation of new links conforming to the new hair curl (e.g. by oxidation from the surrounding air). A more medically relevant example is the hardening (and cracking) of skin that is associated with arsenic poisoning (hyperkeratoses, EHP112:1104) where the increased level of links in the skin keratins may be due to the glutathione depletion that is associated with arsenic clearance from the body.

Disulfides are more oxidized than thiols and therefore the concentration of randomly formed disulfides relative to thiols is higher in the more oxidative environment outside of cells than it is within cells. Thus, although extracellular oxidation and reduction reactions serve important functions, in many cases the dominant mechanisms are different from those within cells. This is especially true because although the majority reactions within cells involve enzymes, a much larger proportion of extracellular reactions do not (observation of the Applicant).

The ability of thiols to serve as reducing agents is well known, but, interestingly, disulfides can also serve to break intermolecular disulfide bonds that are under stress (with a thiol serving in a catalytic role), especially in the extracellular environment, as the following example illustrates. If an intraprotein disulfide bond is under stress (PS-SP in the equations below), a passing thiolate ion (RS⁻) is likely to participate in a thiol-disulfide exchange reaction that will allow the stressed bond to separate. Although the thiolate has now become disulfide bonded to one side of the formerly stressed protein link (PSSR), the other side has become an exposed thiolate ion on its protein (PS⁻). This thiolate ion will now tend to react with any passing disulfide molecule (e.g. ASSA in the equations below, representing diallyl disulfide, which is usually abbreviated as DADS). This exchange reaction will have the net effect of leaving one half of the formerly passing disulfide attached to the former thiolate, and a new thiolate ion will be released to drift away. Hence, the net effect is that the original thiolate ion has been replace by a new thiolate ion, the former stressed link has become two blocked cysteines, and a formerly floating disulfide molecule has disappeared.

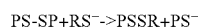

PS-SP+RS⁻->PSSR+PS⁻

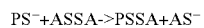

PS⁻+ASSA->PSSA+AS⁻

The ability to increase the concentration of extracellular thiol and disulfide molecules (e.g. by providing AllylSH, DADS, and SAMC) is an important feature of the present invention because it allows the stress to be removed from disulfides that otherwise would remain stressed, and it has now been illustrated how the extracellular disulfides contribute to the extracellular antioxidant activity, in addition to the extracellular thiols.

Note that although each individual thiol-disulfide exchange reaction has involved both an oxidation and a reduction, there is a net antioxidant effect (in terms of reversing the damage previously caused by oxygen exposure) because the stress that has been caused by the possibly inappropriate link between a pair of proteins has been replaced by a less stressful configuration. Given that there is some optimal level of inter-protein links in, for example, healthy skin, the maintenance of a level of thiols (and disulfides) comparable to that of a young person can maintain the extracellular environment closer to that of a young person.

Another example is provided in FIG. 5 and FIG. 6. A stylized depiction of the unfolded polypeptide chain for the milk protein alpha-Lactalbumin, including its known disulfide bonds, is shown in FIG. 5. Although this depiction (from QP551.M433:331, FIG. 3) does not accurately portray the conformation of the actual protein, it illustrates that the disulfide bonds constrain the potential motion of the amino acids close to these bonds.

FIG. 6 shows that the same polypeptide chain in the presence of an excess of allyl mercaptan (in the form of ASH and also some AS anions) and an excess of DADS (shown as AS-SA). The former disulfide bonds that were bridging the cysteines in the molecule are all now "blocked" by allyl mercapto radicals. It can be easily seen that the elimination of bridges has removed their constraint on the motion of the amino acids.

The Applicant has performed experiments with actual milk protein that show that mixtures with water are quite "sticky", indicating that there are a large number of disulfide bonds between the molecules. But when excess allyl mercaptan is included, the mixture becomes completely fluid when left overnight.

The question now arises, which version of the polypeptide chain should be considered "more oxidized"? The blocked verision (FIG. 6) has twice as many disulfide bonds, so by simple count it wins. But the bridged version (FIG. 5) is much "stiffer" (in other words, it is oxidized where it counts). From a macroscopic point of view, it would be considered more oxidized because, in general, oxidation is observed to make things stiffer (the hardening of rubber comes to mind). It is apparent that the opposite effect of "bridging" versus "blocking" is not adequately represented by the terms "oxidized" and "reduced" (or in this example, the terms "oxidized" and "oxidized", because neither case is actually reduced).

The Applicant notes that in contrast to thiols and thiosulfinates, disulfides are relatively unreactive. For example, the exposed SH of the amino acid cysteine is the most reactive residue among the 20 amino acids in proteins, especially when it is in the thiolate state (CyS$^-$). The active site of many enzymes involve a cysteine. Thiols auto-oxidize (in the presence of oxygen) forming disulfides, which could adversely affect shelf life when they are used in products. Thiosulfinates are very reactive oxidants and therefore have a short lifetime in biological systems (and a short shelf life, when used in products). However, disulfides do not have any "exposed" sulfur or oxygen atoms, so they tend to be very stable and to only react quickly with thiolate ions. Therefore, the Applicant regards the "reduced" thiolate ion as being much more reactive than the "oxidized" disulfide, and attributes the rapidity of thiol-disulfide exchange reactions to the high reactivity of the thiolate ion, not the disulfide.

4.4.3 Sources of Allicin 4.4.3.1 Raw Garlic

Upon crushing garlic and breaking its cell walls, the enzyme allinase converts the previously separately compartmentalized S-allylcysteine sulfoxide (alliin) instantly to allicin (RM666.G15K6313, page 48). Interestingly, for the garlic plant itself this produces the antimicrobial agent precisely when and where it is needed: in response to the destruction of its cell walls by bacteria or fungi. (For us, it burns the mouth when we chew it.) Other species of alliums also contain one or more S-alk(en)cysteine sulfoxides with the general formula RS(O)CHC$_2$H(NH$_2$)COOH which are also converted to the corresponding thiosulfinates by an alliinase when crushed. For Chinese chives (*A. tuberosum*) the primary substituted group (R) is methyl, for scallion (*A. fistulosum*) and chives (*A. schoenoprasum*) R=propyl, and for onions (*A. cepa*) R=1-propenyl (JAFC50:3856). All of these are representative of the range of compounds related to the present invention, however the discussion here concentrates on allicin derived from garlic (*A. sativum*, R=allyl) because this is the most researched compound of the class.

It is important that these vegetables be crushed while still raw because the enzyme alliinase is rapidly destroyed by cooking. The analysis of cooked garlic that was not crushed prior to cooking shows that it does not provide any allicin at all (RM666.G15K6313, page 68), although the other organosulfur compounds in cooked garlic probably provide some health benefits, to the extent that they survive being cooked and can metabolize to thiols.

Even if allicin is formed prior to cooking, there is significant loss of organosulfur compounds during cooking. For example, stir-frying smashed garlic cloves in hot soybean oil for 1 minute in a Chinese wok eliminated all of the allicin and only retained 16% of the other sulfides (RM666.G15K6313, page 68). The same set of tests showed that boiling for 20 minutes eliminated 93% of the thiosulfinates and 97% of the sulfides.

Average daily consumption of garlic by Americans is reported to be less than ⅓ of a clove per day (1.4 g/day, assuming an average clove of 5 g, NUCA34:42). Asian food (e.g. Indian food) commonly contains garlic and onions, especially in dished cooked with meat. A population in China has been reported to consume 4 cloves of garlic per day (RA784.N836:311, presumably this garlic has been cooked!). Some garlic is contained in processed foods. It is unlikely that any population consumes more than one clove a day of fresh garlic and 10 cloves a day of cooked garlic.

For dosage calculation purposes, assuming that cooking retains 10% activity, the maximum equivalent dietary consumption of *allium* foodstuffs within any human population is estimated to be the sum of 10 cloves of cooked garlic and one clove of raw garlic, which equals 2 cloves of raw garlic, or 20 mg of bioequivalent allicin per day (see below for the definition of allicin bioequivalence).

4.4.3.2 Garlic Supplements that Produce Allicin from Alliin

The poor stability of allicin has traditionally prevented it from being incorporated directly into dietary supplements. Instead, these products contain the allicin precursor alliin along with the enzyme alliinase, with an enteric coating utilized to prevent their mixing together until they reach the intestine. The allicin release from these products has been problematical, because if the coating dissolves too soon the stomach acids will instantly deactivate the alliinase enzyme, but if the coating lasts too long, the reaction never occurs. In a survey of dietary supplements published in 2001, only one supplement achieved its claimed bioavailable allicin (JAFC49:2592).

For example, in 1993 a change in the manufacturing process for "Kwai" garlic tablets caused their allicin yield to change from 73% of the theoretical yield to only 23%. This was discovered only after several clinical trials were conducted using these tablets (on the serum cholesterol lowering ability of garlic). In retrospect, the results of the various clinical trials can be seen to correlate with the actual allicin release from the various products tested (PM67:13).

4.4.3.3 Allicin Supplements Containing "Pure" Allicin

A proprietary process has been developed for stabilizing allicin, allowing the non-enzymatic delivery of allicin in a capsule. These capsules are available from Health Perception UK Limited, Sandhurst, UK. The actual allicin content is not printed on the label, nor is this information available from the manufacturer. Instead, the allicin content of each Allimax capsule is described as "the same amount of allicin that you get from 1 clove of top quality garlic" (Peter Josling, response to inquiry).

4.4.3.4 Toxicity of Allicin and Raw Garlic Powder

Because different garlic preparations contain different garlic constituents, a study of their toxicity was performed (JN131:1109S). Endoscopic examination of the stomach mucosa of dogs 24 hours after the direct administration of raw garlic powder detected erosion at 15 out of 18 sites. But if the garlic powder had been boiled (to inactivate the allinase, thereby eliminating any allicin), no erosion was observed, although there was some redness. When the "AGE" (Aged Garlic Extract) dietary supplement product was used (which contains no allicin), no erosion or redness was observed.

Enteric-coated garlic products release their contents (including enzymatically produced allicin) into the intestine (instead of the stomach). The examination of the intestine of a dog 3 hours after the administration of three enteric-coated tablets showed damaged and lost epithelial cells at the top of crypts (JN131:1109S). The authors concluded that the safety of enteric-coated garlic products was questionable and recommended the use of AGE instead.

4.4.3.5 Dietary Supplements Containing Garlic Oil

Garlic oil capsules contain various allyl sulfides, of which DADS has the highest concentration (RM666.G15K6313, Table 3.20). These products have been experimentally shown to produce more consistent "bioavailable allicin" (see below) than the typical garlic powder tablet, however the garlic oil capsules themselves are less standardized. The taste and odor of DADS and the other constituents of garlic oil significantly limit the concentration of active ingredients (the garlic oil is typically heavily diluted, e.g. the capsules contain over 99% vegetable oil). A comparison of garlic oil dietary supplements found a 50 to 1 range in their total content of allyl sulfides (RM666.G15K6313, Table 3.21).

4.4.3.6 The In-Vivo Anti-Microbial Allicin is Derived from the Oxidation Products of Allyl Mercaptan and Diallyl Disulfide.

In the research leading up to the co-pending application "Organosulphur Prodrugs for the Prevention and Treatment of Infectious Diseases and Pathologenic Immune System Response" (US2004/0235946A1) by the Applicant, a mechanism for the in vivo production of allicin was discovered. Although consumed allicin is rapidly metabolized to allyl mercaptan, it was discovered that in the presence of ROS from activated immune cells the allyl mercaptan can be oxidized to form dialyl disulfide, which in turn can be further oxidized to form allicin. Therefore, even though the consumed allicin rapidly disappears, newly formed allicin can still serve as a localized antimicrobial agent.

Subsequent research leading up to the co-pending application "Medicinal Products Incorporating Bound Organosulfur Groups" (US2005/0260250A1), produced further discoveries relating to the anti-microbial mechanism of allicin. Allicin can oxidize both the SH groups and the S$^-$ groups on proteins, thereby inhibiting the enzymes involved with microbial replication approximately 100× more effectively than other common "SH reagents" (which only oxidize the SH groups when these are in their S$^-$ ionization state).

In other words, after the *allium* related compound is administered, the normal metabolism of the host converts it to a thiol that serves as a systemic antioxidant, with benefits throughout the body of the host. But if the immune system is activated (e.g. when attacking a microbe or tumor cell), there is localized production of allicin which inhibits reproduction in the adjacent microbial or cancer cells. Later, when the immune response terminates, the inhibition reverses and the adjacent cells are free to resume replication. Because most types of host cells replicate infrequently (e.g. once a month) the temporary delay in replication of these few cells is not detrimental to the host.

4.4.4 Metabolites of Allicin

The primary direct metabolite of allicin has been determined to be allyl mercaptan (PM59:A688). The disappearance of allicin is so rapid and so complete that it is undetectable in blood, urine, or stool, even after consuming large amounts of fresh garlic (e.g. 25 g) or pure allicin (60 mg) (JAFC53:1974).

Because of the rapid formation of allyl mercaptan from allicin, other direct metabolites are not readily detected. However, the consumption of allicin and various allicin-derived compounds have been shown to lead to the rapid metabolic formation of allyl methyl sulfide (AMS) and the eventual formation of acetone, either of which can be measured in breath. Therefore, breath analysis for AMS or acetone provides a non-invasive method for verifying the allicin equivalent bioavailability of these compounds (JAFC53:1974). (The term "bioavailable allicin" is used for this, although no allicin is necessarily involved. A more accurate term would have been "allicin bioequivalance".)

Other garlic derived organosulfur compounds that metabolize directly in blood to allyl mercaptan (disappearing in the process) include diallyl disulfide, diallyl trisulfide, ajoene, and S-AllylMercaptoCysteine (SAMC) (PM59:A688). These have all also been shown to produce both breath AMS and acetone, but interestingly the compound DAS (similar to DADS, but with only one sulfur atom) only produces breath acetone and the compound SAC (similar to SAMC but with only one sulfur atom) produces no breath AMS or acetone (JAFC53:1974).

It has been proposed that in vitro or ex vivo studies of the mechanism of action of these compounds should not use these compounds themselves, but rather should use allyl mercaptan, or possibly a further metabolite of allyl mercaptan (RM666.G15K6313, page 214). In other words, compounds which disappear rapidly in the body can lead to misleading results if they are used by themselves in experiments outside of the body. However there are no dietary supplements based on allyl mercaptan itself, presumably due in part to its strong odor (which is much worse than the odor of garlic or the other garlic-derived compounds).

4.4.4.1 The Pre-Hepatic Fate of the Organosulfur Compounds Derived from Garlic

While there sometimes seems to be a confusing variety of garlic-derived organosulfur compounds, when they are consumed they all are exposed to the reactive cysteine of proteins (including the cysteine in foods being simultaneously consumed) and they are all exposed to blood (e.g. during transport from the intestine to the liver). An in vitro study was performed (PM59:A688) to determine their primary reaction products in these environments.

In the presence of glutathione and an active glutathione-reductase system (i.e. within almost all types of animal cells), allicin is rapidly metabolized to allyl mercaptan. This can be shown to occur in less than one minute by the analysis of red blood cells that have been exposed to allicin (PM59:A688). The results are given in Table I of PM59:A688 and are summarized here for the compounds most relevant to the present invention:

TABLE I

Reactions of organosulfur compounds in the presence of blood or cysteine

| | Reaction with Cysteine | | Reaction in Blood | |
|---|---|---|---|---|
| Compound | Half-life (min) | Product (moles) | Half-life (min) | Product (moles) |
| Allicin | <1 | SAMC (2) | <1 | AllylSH (1.6) |
| DADS | 45 | SAMC (1), AllylSH (1) | 60 | AllylSH (0.8) |
| SAMC | NR | | 3 | AllylSH (0.8) |
| AllylSH | 80 | SAMC (0.8) | NR | |

These results show that regardless of which compound is consumed, SAMC can be formed as an intermediate and allyl mercaptan (AllylSH) is the primary final product in blood.

4.4.4.2 Metabolites of Allyl Mercaptan

The primary direct metabolites of allyl mercaptan are the disulfide DADS and various mixed disulfides, especially those involving cysteine. The disulfide can form via oxidation, but the more likely path is through various thiol-disulfide exchange reactions (see below). The mixed disulfides are also formed primarily via exchange reactions. Exchange reactions involving thiols do not require "metabolism" per se, because the mere presence of disulfides (or mixed disulfides) is sufficient for these reactions to occur.

Although finding allicin or its metabolites in the blood or urine after garlic consumption has been elusive, it has been known for some time that allyl mercaptan and AMS are components of the breath soon after garlic consumption, with the allyl mercaptan disappearing by 1 hour and the AMS having substantially disappeared in 20 hours (JAFC53:1974).

Because AMS is S-methylated allyl mercaptan, the "thiol S-methyltransferase" enzymes are likely to be involved (QP601.E515:131, BBA46:217). These enzymes are distributed in a variety of tissues, but the concentrations are highest in the digestive and excretory tract (stomach mucosa, cecal mucosa, colonic mucosa, liver, and kidney) and lung, indicating that their primary purpose is probably the detoxification of ingested or inhaled substances (QP601.E515:131).

Concurrent with the disappearance of AMS, a significant increase in breath acetone appears, remaining substantially elevated for up to 20 hours, perhaps due to increased triglyceride metabolism (QP601.E515:131). However, no metabolites beyond AMS have been linked to this effect.

The S-conjugation between allyl mercaptan and nitric oxide (forming a nitrosothiol) may also be biologically significant. Nitrosothiol formation increases the effective lifetime of nitric oxide in circulation from a half life of about 5 seconds to many minutes, potentiating its systemic effects (RB170.B57:287 FIG. 3). Nitrosothiols can freely participate in exchange reactions with thiols (e.g. RSNO+R'SH=R'SNO+RSH). Many of the biological effects of nitric oxide have been found to involve nitrosothiols, rather than nitric oxide itself.

4.4.4.3 In Vivo Enzymatic Production of Allicin from Dads

Allicin has been shown to be produced in the liver from diallyl disulfide (DADS) via several cytochrome P-450 enzymes (e.g. CYP2E1) and flavin-containing monooxygenases (DMD27:835). Thus the in vivo production of allicin can be accomplished by any mechanism that delivers DADS molecules to the liver. (Note: the DADS molecule is identical to an allicin molecule with the oxygen atom removed. Conversely, the monooxygenation of a sulfur atom in a DADS molecule results in the formation of an allicin molecule.)

The activity of the enzymes is moderate (up to $8 \times 10^{-8}$ pmol/min/pmol CYP2D6), resulting in approximately 30% conversion of DADS to allicin in 30 minutes (DMD27:835). Although not mentioned in the reference, it is interesting to note that because any DADS in circulation is likely to pass through the liver multiple times, this results in a "sustained release" of allicin. In comparison, if 100% of the DADS was converted to allicin in the first pass, the release would be much more rapid (and of shorter duration). Also, because Cytochrome P-450 enzymes are present in a variety of cell types, the enzymatic production of allicin from DADS may also occur in cells throughout the body ("distributed release"). However, the allicin that is produced will be rapidly converted to allyl mercaptan (see section 4.2.5.1 above), so any direct effect of the in vivo enzymatic production of allicin from DADS is likely to be very local to the site of production.

4.4.4.4 Targeted Delivery of Allicin

By chemically conjugating the enzyme alliinase to an antibody to a specific tumor marker (ErbB2) that is present on the surface of tumor cells, and also administering alliin into circulation, allicin is produced at the specific location of the tumor (MCT2:1295), and only at this location. This was shown to inhibit tumor growth nearly completely, without significantly affecting the rest of the body. It should also be effective as a preventive of metastases because the general circulation of both the conjugated alliinase and the alliin can find the migrated tumor cells anywhere in the body, and before they are otherwise detectable.

4.5 Toothpaste with Organosulfur Ingredients 4.5.1 Prior Art Experiments with Garlic Extract Mouth washing with a 10% w/v garlic extract solution (from fresh garlic, blended, centrifuged, and then filtered) has been shown to reduce the concentration of mouth bacteria by a factor of ~100,000 (P38:747). The authors did not describe how the volunteers were recruited, or whether they experienced any pain and suffering during the experiment, but the 10% solution must have burned the mouth somewhat.

A more comprehensive set of experiments were performed in vitro evaluating the efficacy of garlic extract against 20 species of bacteria (both Gram-positive and Gram-negative) and fungi. They found that the garlic extract had a wide spectrum of anti-bacterial activity, inhibiting all of the species tested, typically with a MIC of 71.4 mg/ml for the Gram-positive bacteria, 17.8 for the Gram-negative, and 8.9 for the fungi (AOB50:645). Of particular interest was the effectiveness at killing *P. gingvalis* (MBC=8.9), which is considered to be a cause of progressive peridontitis.

Although these results are impressive, they do not constitute a mouth wash (or toothpaste) that people could be expected to willingly use.

4.5.2 Prior Art Oral Compositions Incorporating Amino Acids

The U.S. Pat. No. 4,486,403 teaches and claims the use of the amino acid cysteine as a method to prevent the formation of dental carries (cavities).

The U.S. Pat. No. 5,906,811 teaches and claims the use of glutathione as an intra-oral-antioxidant.

4.6 Skin Lotions with Organosulfur Ingredients 4.6.1 Prior Art Experiments with Garlic Extract Lipid soluble garlic extract (from fresh garlic, using a chloroform:methanol based extraction procedure) has been shown to be effective in the treatment of patients with warts and corns in a series of experiments involving 28 patients with warts and 9 patients with corns. They were matched with a control group consisting of 5 patients with warts who were treated with a chloroform:methanol solution (IJDERM44: 612). Of the patients with warts, 23 showed complete recovery and the remaining 5 showed partial recovery. Of the patients with corns, 7 showed complete recovery and the remaining 2 showed nearly complete recovery. The controls showed no improvement.

4.6.2 Allimax Cream

A skin cream containing 5% "allicin liquidium" is available from Health Perception UK Limited, Sandhurst, UK. It is a daily protection cream that purifies the skin, encourages new skin and kills bacteria. The allicin odor is disguised by using a honeysuckle extract.

5. SUMMARY OF THE INVENTION

The Applicant has discovered that certain organosulfur compounds augment the properties of the biothiols cysteine and glutathione, providing greater benefit to the host than that of endogenous cysteine and glutathione alone. These compounds also have unique anti-microbial and anti-inflammatory properties, beyond those of cysteine and glutathione. The Applicant has discovered in particular that these compounds and their properties are beneficial in personal care products such as toothpaste, skin lotions, and deodorants.

The formulations of the present invention are suitable for continuous preventative use, providing general health benefits while offering some protection from various potential diseases. A higher dosage can be utilized when increased protection is desired, for example, in the event of exposure to an infectious disease, or during travel that could involve such exposure, or during low-level exposure to an environmental toxin, or for the treatment of a chronic disease. A still higher dosage can be used as a drug for acute or catastrophic care during the treatment of a disease or other medical condition.

The present invention provides formulations for external use (and for internal use but not consumption, such as for toothpaste), and methods for producing and administering such formulations, the formulations having certain health or medicinal benefits. More particularly, the methods and formulations of the invention provide drugs and prodrugs comprising certain organosulfur compositions, such as allyl mercaptan or the allyl mercapto radical bound to larger molecules such as proteins, resulting in the formation in the body of various *allium* related compounds such as alyl mercaptan, diallyl disulfide, allicin. The use of bound organosulfur compositions avoids a variety of difficulties associated with alternative forms of administration of organosulfur compounds. In the present invention *allium* related compounds are provided in formulations where they are bound to an appropriate carrier for delivery to a host. For example, in particular embodiments they are bound to dermatologically acceptable carriers for use in skin lotions, creams and the like and to orally acceptable carrers for use in dentifrice products such as toothpaste.

Particular embodiments are disclosed that are "low tech" in that they utilize inexpensive ingredients and are subject to a simple manufacturing process, allowing their widespread manufacture and use by economically disadvantaged groups.

Other aspects, advantages, and novel features of the invention are described below or will be readily apparent to those skilled in the art from the following specifications and drawings of illustrative embodiments.

6. BRIEF DESCRIPTION OF THE DRAWINGS

Figure 1:
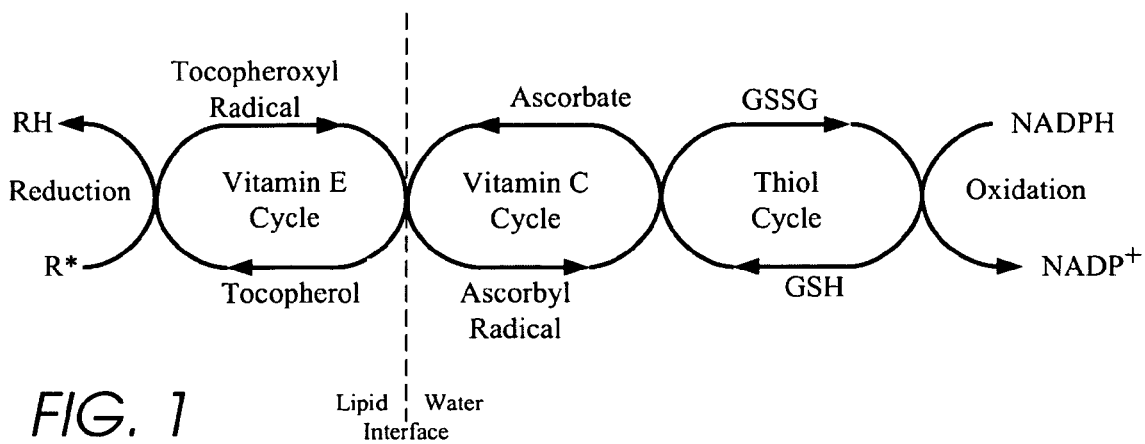
FIG. 1 illustrates the participation of glutathione in the thiol cycle of the antioxidant network.
Figure 4:
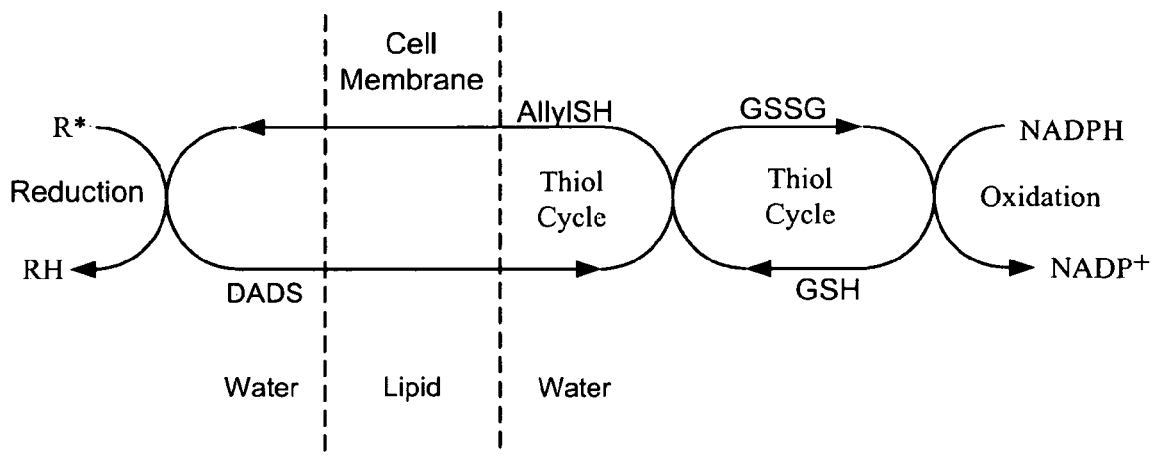
FIG. 4 illustrates the participation of allyl mercaptan in the antioxidant network.
Figure 2:
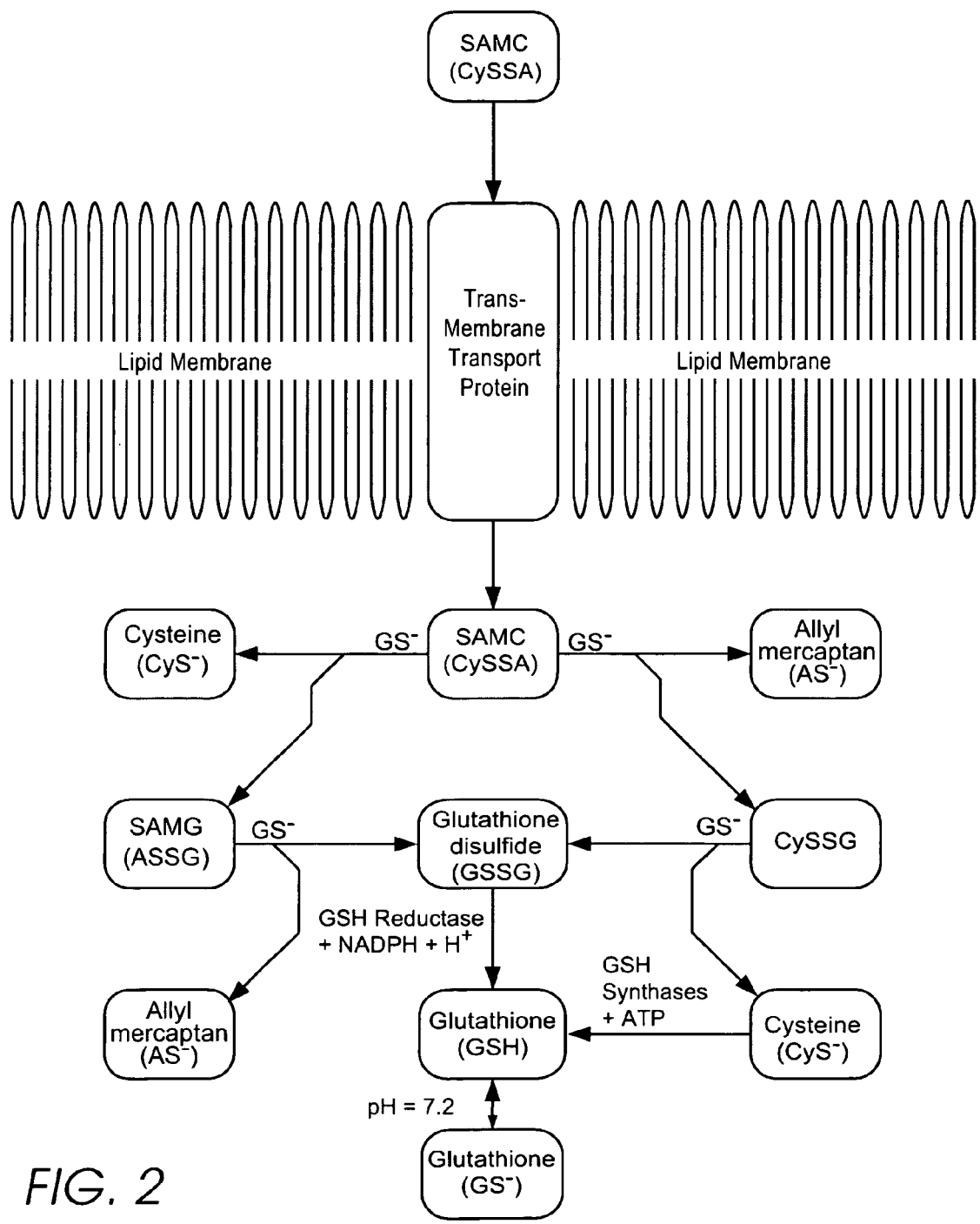
FIG. 2 illustrates the cellular metabolism of SAMC and some of the thiol-disulfide exchange reactions involved.
Figure 3:
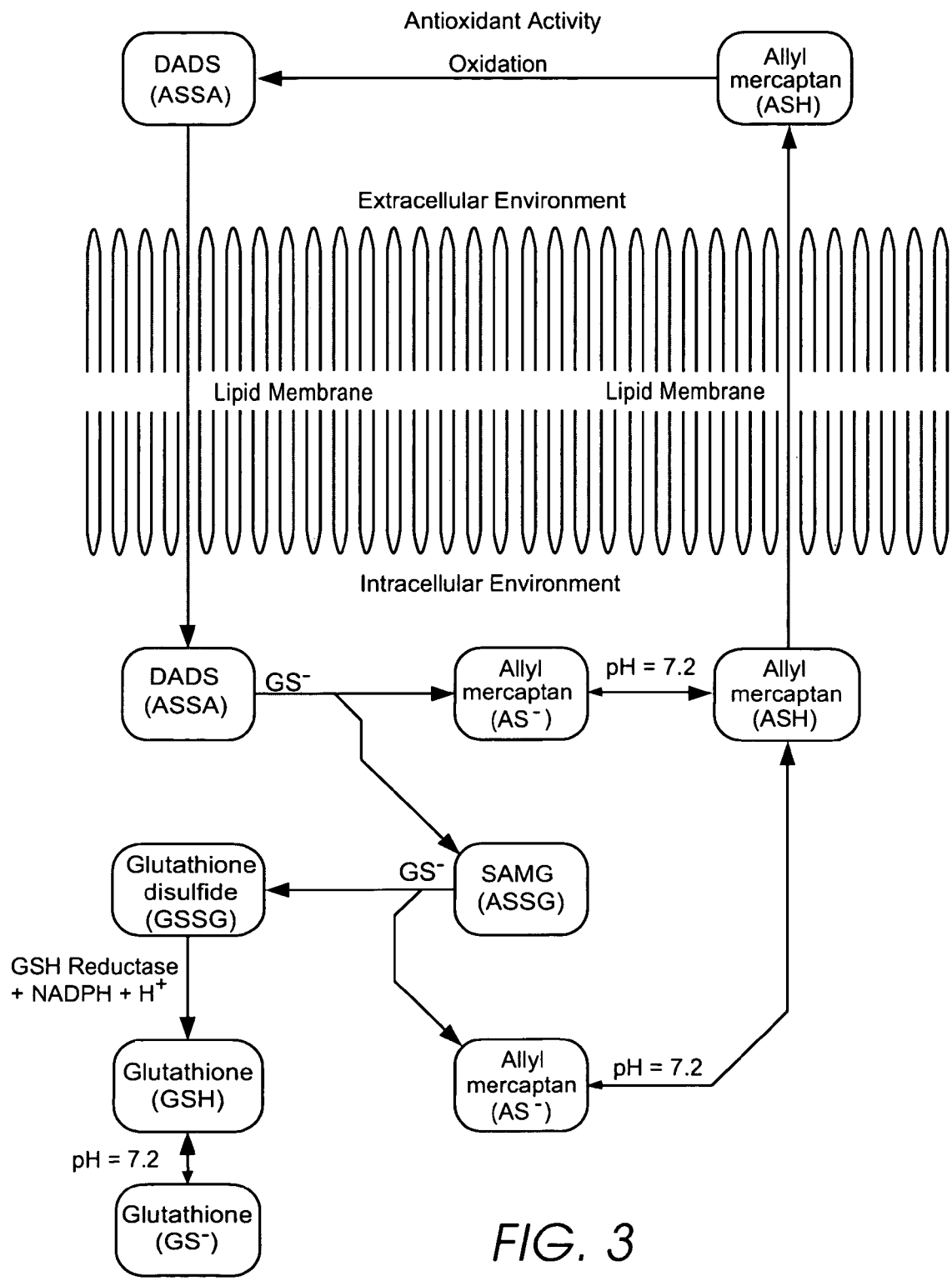
FIG. 3 illustrates the transmembrane coupling of an extracellular antioxidant with the intracellular antioxidant network.
Figure 5:
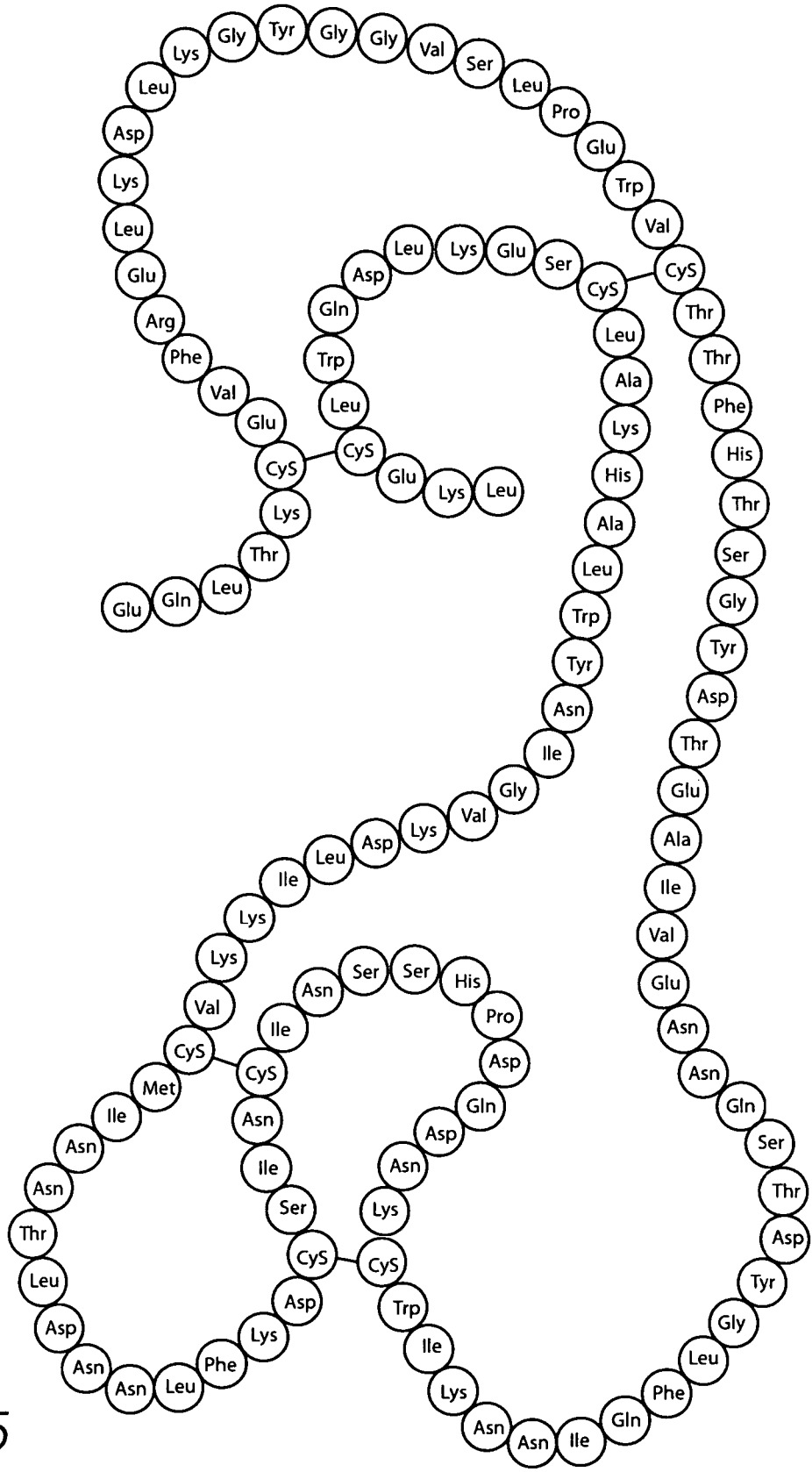
FIG. 5 illustrates a polypeptide chain with disulfide bridges between its cysteines.
Figure 6:
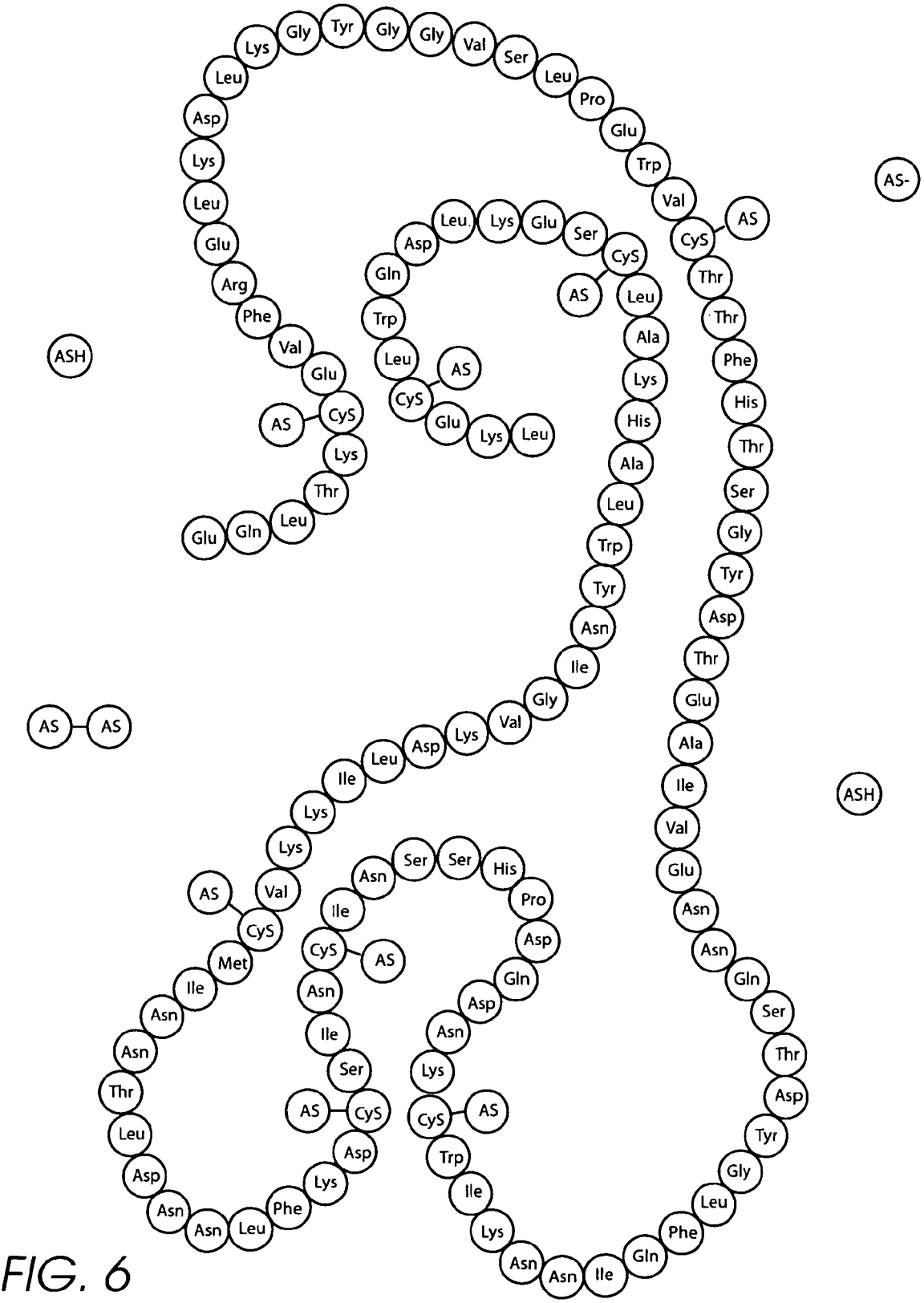
FIG. 6 illustrates a polypeptide chain with its cysteine amino acids blocked.

7. DETAILED DESCRIPTION OF ILLUSTRATIVE EMBODIMENTS 7.1 "Squeaky Clean" Toothpaste The Applicant has determined that the *allium* related compounds, although serving as antioxidants throughout the body, can become oxidized by the intense hydrogen peroxide (and other oxidants) emitted by neutrophils and other cells participating in an immune response (US2004/0235946A1). It is known that saliva contains neutrophils and that they can become activated and produce reactive species (FRR28:485, JBC261:9694). The salivary glands also produce hydrogen peroxide, apparently as an antimicrobial agent (II62:529). Interestingly, some types of oral bacteria (e.g. oral streptococci) produce hydrogen peroxide (perhaps to kill other oral bacteria) and are very tolerant to it (II62:529), but they are not tolerant to allicin (AOB50:645).

7.1.1 Mechanism of Antimicrobial Action

The mechanism of antimicrobial action of the *allium* related compounds is taught extensively in US patent application publication numbers US2004/0235946A1 and further in US2005/0260250A1, the disclosures of which are incorporated herein by reference.

Briefly, it is shown, both experimentally and theoretically, that allyl mercaptan can be oxidized to diallyl disulfide and further oxidized to allicin in the presence of hydrogen peroxide. It is further shown, both experimentally and theoretically, that allicin is an extremely efficient inhibitor of the "SH" sensitive enzymes that are required for various functions related to replication (e.g. RNA synthesis) and that this inhibition is reversible when the exposure to allicin terminates.

The high permeability of allicin through cellular membranes allows the allicin that is produced adjacent to the activated neutrophil to penetrate any adjacent microbe and inhibit its replication. In effect, the *allium* related compound (e.g. allyl mercaptan or diallyl disulfide) has detoxified the hydrogen peroxide (a relatively non-specific oxidant that can permanently damage the host's cells) and produced a more specific toxin (allicin) that is more toxic to the microbe, but relatively non-toxic to the host.

7.1.2 The Development and Testing of an Antimicrobial Toothpaste

The desired toothpaste has the conflicting requirements of being sufficiently active to eliminate the microbes during the time of brushing (or to leave substances in the mouth that would continue to have antimicrobial activity after brushing) and not having an offensive taste or smell. However, the Applicant choose to initially experiment with organosulfur ingredients that were already classified as "Generally Recognized as Safe" (GRAS) food additives by the FDA. If one or more of these could be made to work, their existing GRAS status would be very beneficial.

Although allicin has the highest short-term antimicrobial activity, it would burn the mouth if a high concentration was used. Also, the production of the allicin (e.g. from garlic powder and water) would need to be done at the time of use, due to its short shelf life. As the Applicant has discovered, either allyl mercaptan or diallyl disulfide, if they remained in the mouth, could produce allicin in response to an adjacent activated immune cell. This would provide very local antimicrobial activity, hopefully without burning the mouth.

Both allyl mercaptan and diallyl disulfide are membrane permeable, so if released in the mouth either compound could enter the cellular membranes of the cells lining the oral cavity and remain there after the brushing completed.

Because allyl mercaptan is water soluble, it is easier to experiment with than diallyl disulfide (which is an oil). For example, an experiment with diluted allyl mercaptan (1/200, using distilled water) poured over the toothbrush bristles showed a reduction in plaque after a week of use, but the smell and taste of the allyl mercaptan were offensive.

I decided to next try mixing it with the toothpaste that I normally use by squeezing out the contents of a tube of Arm and Hammer Dental Care Toothpaste into a bowl, mixing in 10 ml (2 teaspoons) of 1/200 diluted allyl mercaptan, and then returning the toothpaste to the tube. (People have asked "But how do you get the toothpaste back into the tube?". The toothpaste was first transferred into a ketchup bottle by spoon, then the spout of the ketchup bottle was placed into the mouth of the toothpaste tube and the toothpaste was squeezed from the bottle into the tube.) One advantage of using toothpaste (instead of water) as the base ingredient is that significantly more of it can be applied to the brush. Mixing with a conventional toothpaste provides an adequate carrier for the *allium* related compound. More generally, of course, any orally acceptable carrier suitable for application to the teeth may be used. By orally acceptable carrier is meant a carrier that is itself inactive, is suitable for topical application in the oral cavity, does not bring about any adverse effect to the oral cavity, and allows the active ingredient to be released when applied in the oral cavity. This includes the carriers used in commercially available toothpastes, tooth powders, or other dentifrice products.

The resulting toothpaste has no significant "garlic" smell or taste. It left the mouth feeling very clean, so clean that unwaxed dental floss "squeaks" when slid up and down the side of each tooth. It was observed that with use the plaque went away, and saliva became more watery.

Apparently, the allyl mercaptan was binding sufficiently to some ingredient in the toothpaste to keep it from being volatile, and was being released well enough inside the mouth to be effective. The first three ingredient listed on the toothpaste box are baking soda, water, and glycerin, so I tried making a toothpaste with just these ingredients, with good results. I suspected that the allyl mercaptan was binding non-covalently with the glycerin, so I tried an allyl mercaptan, water glycerin mix, which also worked well (and had a slightly sweet taste). For completeness I also tried a mix of baking soda, water and allyl mercaptan, which, surprisingly, also worked well (and had a baking soda taste, which I don't like).

Although these all worked acceptably, the best taste and texture were obtained with the commercial toothpaste as the base. Although in the end it appears that adequate binding of allyl mercaptan is readily accomplished for this application, the Applicant notes that said binding is essential for the acceptance of the product. Experiments with various skin lotions (see below) and with foods and beverages (see US2005/0260250A1) show that although many simple mixtures are acceptable, many others are unacceptable. For example, mixtures with water or products that are essentially water based can produce a horrible smell (or taste, as the case may be).

Several friends and acquaintances were willing to try the toothpaste and provide feedback. Under a "Nondisclosure and Produce Evaluation Agreement" I supplied them with free samples to evaluate. The agreement specified that the samples are not for sale, that the inventive aspects of the samples are confidential, and that the samples have no warranty.

The toothpaste is very popular with the evaluators, several of which have said that it is the best toothpaste that they have ever used. One evaluator (SP) wrote:

"We were hoping for the next supply of toothpaste soon. MP and I use less paste at each brushing than we did before. MP is still twice a day and me once a day. My dentist still remarks that my gums look healthy. Curious still that neither of us has had a canker sore or mouth sore since we began using it."

The applicant notes that mouth sores are reported to have a variety of causes, including viral infection. The observation of their elimination could be due to either the antimicrobial properties of the toothpaste, its antioxidant properties, or even its anti-inflammatory properties.

Another evaluator, KW wrote:

"We have used the toothpaste everyday, and use no other kind of toothpaste. Our teeth are remarkably clean, with no sign of plaque. Our dentists (we have two separate dentists) remark at how our teeth are so plaque free. It has also improved our fight against cavities. Our teeth are always shiny clean and very smooth. We plan to keep using this toothpaste indefinately."

In response to a request from the Applicant for the evaluators to switch to a "control" toothpaste for six weeks, KW wriote:

"Send it. We can live with a little plaque for a short time." But to the same request, SP replied:

"I hear that KW and CW have accepted the suffering. I will also accept the suffering . . . Now, for MP, no matter how I explain the importance of your request, absolutely refuses to do this and has asked me when I will get more of it; she does not want to run out again, like the last time. To give you some background, MP was once married to a dentist for quite a few years and has seen a lot of teeth. She also has used and tried a lot of different brands and versions of toothpaste—Colgate (various versions), Crest (various versions), aquafresh, and many of the others, including the Arm & Hammer one. From her experience, there is absolutely none like this one and she uses it exclusively twice a day. It keeps away minor tooth pain (she has some crowns that will need to be replaced soon). It cleans her teeth, it keeps her mouth clear of any mouth (canker) sores, it will not allow the rough coating of layer on the inside of the teeth, and it leaves the very smooth feeling on her teeth—unlike any other. She is a total convert. So, if you would, send me the good stuff for MP and send me the control stuff for my 6 yucky weeks."

After using the control KW wrote:

"I used the toothpaste for about 7 weeks and went to the dentist last week. The technician who regularly cleans my teeth said she saw only minimal plaque buildup at the gum line on the inside of my front bottom teeth. I had my teeth cleaned late in January and she said she didn't expect there to be too much plaque anyway since I brush good and regularly. However, while I was on the regular toothpaste I did notice two significant things, my teeth did not feel as slick and I had a bad taste in my mouth. I'm glad to be back on the good stuff, which I started Friday, May 5. CW is still on the regular stuff and I'm not sure she can get to the dentist because she just underwent major abdominal surgery last week and will be recovering for several weeks. She has the same comments, teeth not as slick and bad taste. She wants to get back to the good stuff."

Similarly, SP wrote:

"I used the control toothpaste in the evening for 6 weeks from March 23-May 4 and went to the dentist on March 23 & May 4. The dentist checked out my teeth measuring for gum recession or anything else both times. The dentist didn't notice any difference after 6 weeks. He said "Your gums look very healthy." I previously made a note to you that this unsolicited comment first came from my dentist after I had been using the good toothpaste. As for my feedback during the six weeks using the control stuff: The silky smoothness on the back of my teeth was mostly gone after about a week—yuck! My mouth also didn't feel so clean or fresh anymore. By the second week and about every week or two after, my 7 year old daughter would mention that I had bad breath (my wife said it more nicely)."

7.2 Skin Care Products 7.2.1 Mechanisms of Antioxidant and Anti-inflammatory Action The mechanism of antioxidant and anti-inflammatory action of the *allium* related compounds is taught extensively in US2004/0235946A1 and further in US2005/0260250A1, which are included here by reference.

Briefly, it is shown, both experimentally and theoretically, that allyl mercaptan serves as a "thiol" antioxidant, becoming oxidized to diallyl disulfide in the process. The diallyl disulfide is converted back to allyl mercaptan by the glutathione reductase mediated (and NADPH driven) "antioxidant cycle". The allyl mercaptan and diallyl disulfide are both membrane permeable, therefore this antioxidant activity is available both inside and outside of the cell.

This antioxidant activity provides anti-inflammatory properties through a variety of mechanisms. One it that it reduces the host's potentially excessive immune response (this is discussed extensively in US2004/0235946A1). Another is that it enhances the activity of the nitric oxide synthase enzymes (e.g. eNOS). Nitric oxide promotes blood flow and is known to decrease the adhesion of immune response cells (e.g. macrophages) to blood vessel walls.

The eNOS enzyme is feedback regulated by nitric oxide itself via the S-nitrosylation of a critical SH group. (S-nitrosylation is analogous to the S-thiolation of an SH group (i.e. the blocking of the group by a thiol) (QP535.N1N547:41). The Applicant notes that just as S-thiolation can be reversed by a thiol-disulfide exchange reaction that leaves the enzyme with an active SH group as the disulfide floats away, S-nitrosylation is reversible by a thiol-nitrosothiol exchange reaction that leaves the enzyme active as the nitrosothiol floats away. In other words, in the presence of excess thiols (relative to the nitric oxide concentration), each eNOS molecule tends to remain activated, resulting in a higher nitric oxide concentration at equilibrium.

The activation of the DNA transcription factor NFkB is known to be a significant factor in the development of inflammation. The NFkB signaling pathway is complex, with multiple paths for activation and multiple points that can be used for inhibition of activation (Q11.N45V1030:1). *Allium* related compounds (e.g. DADS) have been shown to inhibit the expression of various pro-inflammatory cytokines (e.g. IL-1, TNF-alpha and IL-10) that activate NFkB (JN133: 2171).

The Applicant notes that nitric oxide is known to be a potent inhibitor of NFkB activation. It has been shown experimentally that a concentration of less than 1 micro-mole of nitric oxide (e.g. as released experimentally from a 1 micro mole concentration of S-Nitrosocysteine) nearly completely inhibits the activation of NFkB in macrophages (BICH40: 1688). Another study, which used a nitric oxide probe to measure the nitric oxide concentration, showed that a 20-100 nano mole concentration inhibited the DNA binding activity of the NFkB signal transduction proteins p50 and P65 (NARE24:2236). Therefore the increase in nitric oxide concentration that results from the administration of *allium* related compounds can be expected to result in decreased NFkB activation. Although the control of NFkB activation is complex, the paths converge in the cell nucleus at the point of DNA transcription. Because the interaction with nitric oxide occurs at this stage (BICH40:1688), its "anti" NFkB effect will tend to override any other "pro" NFkB signaling. The Applicant does not intend to imply that the only mechanism by which the *allium* related compounds affect NFkB activation is via nitric oxide production, but presents this as a possible explanation for the potent, broad spectrum, anti-inflammatory properties that have been observed when testing skin lotions that incorporate *allium* related compounds (see below).

7.2.2 "Universal Antioxidant" Skin Lotion 7.2.2.1 Development and Testing of a Skin Lotion The development and testing of the skin lotion has a relatively long history, and parallels the Applicant's gradual discovery of the mechanisms behind the medicinal properties of the *allium* related compounds. Initially, the Applicant believed (like many other researchers in this field) that the "active ingredient" in garlic was allicin, and that in order to be effective a product needed to contain (or immediately produce) allicin.

The skin cream "Allimax", which contains 5% allicin, is available from Health Perception UK Limited. The Applicant purchased some for testing.

The Applicant has a mild condition of facial seborrheic dermatitis (flakey skin), which has been successfully treated for many years with a combination of Ketoconazole cream (anti-fungal) and mometasone florate cream (steriod). The condition readily occurs when treatment is discontinued, so this provides a readily available method for quickly testing the anti-fungal and/or anti-inflammatory properties of skin creams and lotions (most skin lotions have been found to make the condition worse). The Allimax cream was very effective, easily passing the test.

When the Applicant discovered that allicin can be produced in vivo in response to ROS generated by an activated immune cell, and that allyl mercaptan can be used both as an antioxidant and as a precursor for allicin production, he realized that this could lead to a beneficial formulation for a skin cream.

The desired skin cream has the conflicting requirements of being sufficiently active to treat the skin condition and not having an offensive taste or smell. In practice, this means that it needs to be bound sufficiently to a carrier so that it becomes non-volatile, but the bond needs to be readily broken (e.g. by a thiol-disulfide exchange reaction) upon use in order to yield the active ingredient (in this case, allyl mercaptan). The Applicant tried several skin creams for use as a base, selecting "Jason E Creme" because it worked well and was a premium product. Unfortunately, after a few months the manufacturer changed the product packaging and also apparently changed the product formulation, because it stopped working (as indicated by a return of facial seborrheic determatitis). In general, of course, any dermatologically acceptable carrier may be used. By dermatologically acceptable carrier is meant a carrier that is itself inactive, is suitable for topical application to the skin, does not bring about any adverse effect to the skin to which it is applied, and allows the active ingredient to be released when applied to the skin. Such carriers, or compositions including such carriers, come in such forms as, for example, lotions, creams, gels, and ointments and may include oil-in-water, water-in-oil or any other carrier formulation. Such carriers are conventionally used in cosmetic and dermatologic formulations to facilitate topical application to the skin and need not be described in any detail here.

The first evaluator for the skin cream (other than the Applicant) was the Applicant's mother in law, who has suffered from eczema from birth. Sometimes she would have bright red patches on her arms (and other parts of her body, I am told) which would torment her horribly. She (and her dermatologist) were continuously trying various medications, with limited success. The skin cream was as effective at providing relief as any other medication that she had found. When I discontinued providing the Jason E Creme based product for evaluation, she insisted that I come up with another one, and bought some skin lotions for me to experiment with. Some base lotions worked and some didn't. I ended up selecting a premium product from Neutrogena for use as the new base ingredient for the skin lotion.

An anti-inflammatory, antimicrobial, and antioxidant skin lotion was produced by adding 0.3 ml of allyl mercaptan to the contents of one full 310 ml bottle of Neutrogena Norwegian Body Emulsion, mixing it in a bowl then returning the mixture to the original bottle.

The lotion has been used by the product evaluators as a multi-purpose skin lotion for the treatment of insect bites and poison oak, to treat the redness, pain and itchiness of eczema, rosacea, and sunburn, and to treat foot fungus (onychomycosis) and flaky facial skin (seborrheic dermatitis). It is also very effective as an underarm deodorant.

Perhaps the most important application for the skin cream is as an anti-fungal agent, because there are very few existing products that are effective and don't have side effects. Several of the evaluators had a persistent foot fungus (onychomycosis) that had resisted treatment for years. They had been told that the only available treatment for this is a systemic antifungal that also has potentially serious side effects. The skin lotion has proved to be effective in controlling this fungus (eliminating or nearly eliminating it) even when the fungus is located underneath the toe nail, although the toe nail discoloration returns if the use of the lotion is discontinued.

Note that for whichever purpose the skin lotion is being used, the side effects are also beneficial (unlike many other skin treatments). In the absence of specific conditions, it still can be applied everyday as a general purpose skin antioxidant with healthful, anti-aging properties.

The skin lotion is surprisingly effective as an underarm deodorant, as was discovered by the Applicant as follows. After not using any deodorant for several weeks, an acrid underarm smell developed. Examination of the underarm hairs also showed a thickening, presumably due to bacterial debris. Subsequent treatment with the skin lotion completely eliminated both the smell and the deposits on the hairs. A large drop of lotion (approximately 1/10 of a cubic centimeter) rubbed into the underarm area is sufficient. Although the skin lotion does not prevent sweating, it does eliminate bacterial growth, and could be used in conjunction with traditional deodorant compounds (that prevent underarm sweating) to provide protection from both the odor of sweat and the odor from bacterial growth.

The skin lotion also provides some degree of protection (and relief) from sunburn. After applying the lotion to an area of skin on the arm (leaving the rest of the skin on the arm untreated), exposure to sunlight produced a greater degree of sunburn on the untreated skin. The Applicant estimates that the untreated skin became twice as red as the skin that was pre-treated with the skin lotion. Although the skin lotion does not block the UV, it provides an antioxidant (and anti-inflammatory) agent to the skin that reduces the response to UV exposure, which could be useful when used in conjunction with a UV blocking agent (sunscreen) or for those people who neglect to apply sunscreen prior to exposure to sunlight. A separate experiment showed that the skin lotion provides relief from the burning and itchiness of sunburn.

Further research and experiments revealed that it was not necessary to start with a thiol compound, because a membrane permeable disulfide compound will be readily converted to a thiol inside a cell. Also, it is not necessary to form a disulfide bond between the thiol and the carrier, because for some compounds (e.g. diallyl disulfide) mixed with some carriers, the lipophilic attraction can provide sufficient bonding. If the lotion readily penetrates the skin, the membrane permeable disulfide will also penetrate the skin. This led to an alternate formulation (that can be used as an alternative to the previous thiol-based formulation) which is produced by adding 1/3 ml (10 drops from the eyedropper that I use) of diallyl disulfide to one full 310 ml bottle of Neutrogena Norwegian Body Emulsion, mixing it in a bowl then returning the mixture to the original bottle.

One evaluator (EB) wrote:

"It's Great! The skin lotion that you have developed has helped make my skin much more comfortable. As you know, I have an extreme case of eczema. There were times when the itching got bad, I had used the prescription ointments as often as allowed and needed something more. Your lotion came to the rescue. I can't say it cured the condition, nothing does, but it did allow me the required comfort so I would not scratch the affected area and my skin could heal. I have also been using the lotion as a deodorant and it seems to keep smells under control. With my sensitive skin I found the usual commercial products irritating but your lotion soothed my skin and did duty keeping me odor free.

In addition, I have developed rosacea on my face. The prescription medicine for this is the one that I had been previously recommended for the eczema. The side effects were such that I could not tolerate it. Your lotion, again does not cure, but keeps the condition enough under control that my face does not break out with the characteristic small pimples and bright red flushing. Thank you for your research and good luck."

Another evaluator (CO) wrote:

"For the last 18 years, I have lived near an undeveloped area where a lot of poison oak grows. My cat visits this area, with the result that I pick up several cases of poison oak each spring. I used Cortisone cream to relieve the itchiness, but now I use your cream almost exclusively. Applying it 2-3 times a day is normally all that I need to do to make the itchiness disappear completely. I have only resorted to the Cortisone cream once in the last year, only for the two days when my reaction was at its peak (a reaction normally lasts 1-2 weeks). I have also used your cream to successfully relieve the pain and itchiness of spider bites and tick bites. I am very pleased with it."

Another evaluator (WB) wrote:

"A long-standing fungal nail infection had turned the nail of my big toe completely black. I decided to try the Universal Antioxidant cream that (Applicant) had developed; although I realized that any attempt to cure the condition would require some systemic therapy, I hoped for some possible cosmetic relief. After a month of twice-daily application, the base of the nail started losing the black coloration and returning to normal condition; in an additional couple of months, the whole toe had returned to normal."

7.2.3 Anti-Arsenicosis Skin Lotions

Arsenicosis is the disease that is caused by arsenic poisoning and is currently a major health problem in West Bengal, India and in Bangladesh due to the consumption of arsenic contaminated well water. The problem will get much worse with time, because many of the symptoms are slow to appear, and there is no easy solution to the underlying environmental problem that has been created. The book "Venomous Earth—How arsenic caused the world's worst mass poisoning" (RA1231.A7M44) does a good job of presenting the scope of the disaster.

An estimated 35 million or more people in Bangladesh have been drinking arsenic contaminated water from "tubewells" (BWHO78:1093) that were drilled mostly in the 1970s, before it was realized that there were underground natural geographic formations in the area containing inorganic arsenic. Because of the delay in the development of symptoms, many thousands of wells were drilled before (and after) the problem was discovered, and these wells remain a primary source of "clean" drinking water for many villages. Shallow tube wells are the main source of drinking water for 97 percent of the rural people in Bangladesh (APJCP4:7).

Drilling deeper wells would avoid the layer of underground arsenic, but drilling a deep well can cost up to 45 times as much to drill as the shallower tube wells (RA1231.A7M44: 170). By now, the water has been used extensively for the irrigation of rice, which has permanently contaminated the soil and is producing arsenic contaminated rice (RA1231.A7M44), so even new wells would not completely solve the problem. The scale of this environmental disaster is greater than any seen before, even exceeding that of the nuclear accident in Chermobyl (RA1195.E48:118).

The scope of the problem (and the expense of the proposed solutions) has led to inactivity. The developing medical problems will potentially overwhelm the health care system, making a "personal care" alternative for those who are suffering a potentially important short-term component of any long-term solution to the problem.

Clinical features of arsenic toxicity include hyperpigmentation, hyperkeratosis, nodular keratoses (usually on the palms and soles), skin lesions, weakness, anemia, burning sensations, solid swelling of legs, chronic lung disease, liver fibrosis, gangrene of the toes, neuropathy, skin cancer, and various internal cancers (especially of the lung, bladder, liver, or kidney) (JESH38A:141, EHP108:671).

Hyperpigmentation has been described as raindrop shaped discoloration spots, diffuse dark brown spots, or diffuse darkening of the skin on the limbs and trunk (EHP108:617). It is typically the first symptom of arsenicosis to appear, and is also the most prevalent symptom. There is commonly a progression from hyperpigmentation to nodular keratoses and/or hyperkeratosis, to skin cancer (typically appearing first at the location of a nodule (HTOX8:99)), and then the development of cancer at other locations in the body. This progression takes from years to decades to occur and explains the relative occurrence of symptoms typically observed (hyperpigmentation>nodular keratosis>skin cancer>systemic cancer).

In general, inorganic arsenic consumption is much more toxic than the consumption of organic forms of arsenic (e.g. from seafood such as shrimp) (QH545.A77:117). The inorganic arsenicals from groundwater are typically either based on arsenite ($AsO_3^{2-}$), with the arsenic in oxidation state As(III) or on arsenate ($AsO_4^{3-}$), with the arsenic in oxidation state As(V). The detoxification process that occurs in the body converts the inorganic arsenic compounds to the organic arsenic compounds MonoMethyl Arsenic acid (MMA) and DiMethyl Arsenic acid (DMA), which are then excreted in feces and urine.

A relationship between glutathione and arsenic toxicity is indicated by a study of genetic factors in patients with arsenic-induced skin cancer. This study found that the glutathione S-transferase enzymes were more frequently mutated in these patients (relative to a control group) and that those who had at least one null or variant of GST M1, T1, or P1 had a 5-fold greater risk of developing skin cancer (TAP206:198).

As will be seen from the discussion below, much of the toxicity of arsenic is due to its interactions with biothiols, especially the SH groups of proteins. Because As(III) reacts more readily with thiols than AS(V) does, it is more toxic (QH545:A77:4). Additional toxicity can result from thiol depletion. To a lesser extent, arsenic can also damage molecules that do not contain SH groups (such as DNA). Although these other reactions are fewer in number, they can have serious long term consequences (such as the development of cancer).

Arsenic compounds (arsenicals) are also beneficially used as chemotherapeutic drugs, although some types of cancer cells can acquire resistance to these drugs. Typically, the acquisition of resistance to one of these drugs will also result in these cancer cells being resistant to other, seemingly unrelated, chemotherapeutic drugs. This phenomenon of "Multidrug Resistance" has been extensively researched.

Because thiols (especially glutathione) are important in the detoxification of arsenicals in the body, and also because the Applicant has observed that many of the reported symptoms of arsenicosis are similar to the reported symptoms of glutathione depletion, and also because the metabolism of arsenicals is known to deplete glutathione, the Applicant has investigated the possibility that the observed increase in arsenic toxicity among some populations is due to glutathione deficiency.

Although the Applicant believes that that the toxicity of arsenic exposure is related to the thiol (e.g. glutathione) content of the host, this is not a widely known (or accepted) position among the arsenicosis research community. For example, although the dietary protein of affected groups has been surveyed, the SAA content of the protein has been ignored (e.g. all proteins are considered equal). Similarly, although the dietary content of some types of vitamins and antioxidants have been surveyed, the thiol based vitamins (e.g. thiamin) and antioxidants (e.g. the SAA content of protein) have been ignored.

As another example, the most authoritative book arsenicosis from drinking water ("Arsenic In Drinking Water" (RA1231.A7N38)) makes little mention of glutathione's role in the detoxification of arsenic. Although it does describe several times the toxic reactions of arsenicals with the SH groups of proteins, it does not consider the detoxification properties of simple, non-protein thiols such as glutathione. The most prominent mention of glutathione in the book is its role in the conversion of As(V) to As(III) (RA1231.A7N38: 150), which to the reader would imply an increase in toxicity.

Although the following description relies heavily on the published research results of others, it is largely the extensive research on the use of arsenicals for cancer chemotherapy (where the protective effect of glutathione and other thiols is well known) that provides relevant results for the issue at hand. Although the chemotherapeutic use of arsenicals intentionally induces toxicity, the things that can interfere with this are of great interest to the Applicant in devising ways to reduce the toxicity of environmental arsenic exposure. Therefore, because the Applicant relies upon the alternative use (and in some cases reinterpretation) of much of the research, it is being presented here rather than in the "prior art" section of the application.

7.2.3.1 Roles of Thiols in Arsenic Detoxification

Thiols (especially glutathione) play many roles in the detoxification of arseincals. These can be divided into interactions with inorganic arsenic, the formation of glutathione conjugates for the excretion of arsenicals from cells, and the methylation of arsenicals to monomethylarsonic acid (MMA) and dimethylarsonic acid (DMA), the major arsenic products that are excreted from the body.

7.2.3.1.1 Inorganic Arsenic Forms Complexes with Thiols

The ability of arsenicals to inhibit (or occasionally stimulate) various enzymes is well known to biochemists. For example, the classic, 3-volume text "Enzyme and Metabolic Inhibitors" devotes 195 pages to various arsenicals, including detailed descriptions of many of their effects on animals, but also includes recommendations against their general use in experiments due to their non-specificity (QP601.W38V3: 595). Because perhaps 50% of enzymes contain thiols (or disulfides) that are sensitive to "SH reagents", the arsenicals can affect such a large number of types of enzymes (and other proteins) that it can be hard to attribute any observed results to any specific effect. Modern biochemists have a wide variety of other, more specific, enzyme inhibitors available, so they rarely choose to use arsenicals in experiments.

Arsenic is well known to accumulate in hair and nails. This accumulation is due to their high concentration of "SH" groups and disulfides (RA1231.A7N38:177). This could be viewed as an example of the detoxification of arsenicals by thiols, in this case by the non-essential "SH" groups in these proteins.

Perhaps more relevant to the subject at hand is the protection that non-protein thiols can provide. To the extent that these other thiols successfully "compete" with the enzymes (and proteins), the formation of complexes between the arsenicals and these thiols will "protect" the enzymes. These thiols would normally derive from dietary cysteine (and dietary alliums), which would naturally provide a level of protection (conversely, their deficiency would lead to unnecessary toxicity from the arsenicals that would otherwise be detoxified).

In some circumstances, the application of a more powerful chelating agent has been shown to be beneficial. The invention of arsenical war gases in World War I (e.g. Lewisite) led to the development of "British Anti-Lewisite", a dithiol compound that has two "SH" groups in close proximity, which results in preferential chelation of arsenicals relative to isolated thiols (US002432797), thereby providing protection via competition.

Even when an enzyme becomes inactivated by an arsenical, in many cases it can be fully reactivated by glutathione (S97:356). For example, if an SH group on a protein (e.g. PSH) becomes "blocked" by the arsenical (e.g. becomes PSAsR, where R is the remainder of the arsenical), a glutathione molecule (GSH) floating by can participate in an exchange reaction, restoring the activity of the enzyme (PSH) and producing a less toxic conjugate (GSAsR). (These reactions probably actually involve thiolate ions (e.g. PS$^-$ and GS$^-$), as thiol-disulfide exchange reactions do.)

The Applicant notes that the formation of a complex between a thiol and an arsenical results in the depletion of a thiol that would otherwise be biologically active. If thiols are plentiful, this is clearly beneficial, but if thiols are deficient, this becomes a secondary source of toxicity. People exposed to arsenic therefore have a higher dietary requirement for thiols (and thiol precursors) than the general population does.

Arsenic increases the formation of oxygen radicals, which is the mechanism by which it induces the apoptotic killing of cells. The production of these radicals has been implicated as arsenic's mechanism of producing genetic damage (PNAS98:1643, TOXICOL79:195). These oxygen radicals can be quenched by glutathione, which in turn produces an increase in oxidized glutathione (GSSG) as it protects the cell. Consumption of garlic has also been shown to reduce arsenic toxicity and chromosomal damage, presumably due to its antioxidant activity (EMM21:383).

Although glutathione (and other thiols) rapidly reduce As(V) to As(III), the As(III) can then form a less toxic conjugate with glutathione (RA1231.A7N38:150). A major conjugate that is formed has been shown to be Arsenic TriGlutathione (ATG), which consists of three glutathione molecules conjgated to a single arsenic atom, and forms spontaneously in solution (CRT6:102). The rate of ATG formation is proportional to the cube of the GSH concentration, and therefore declines precipitously during GSH depletion (JBC275:33404).

Arsenicals (especially ATG (CRT10:27)) inhibit the activity of glutathione reductase, which exaggerates the increase in GSSG (and loss of GSH) during initial exposure, but after chronic exposure this is compensated for by a dramatic up-regulation of the mRNA for glutathione reductase enzyme synthesis, resulting in a net increase in glutathione reductase enzyme activity (TOXSCI70:183) and producing an acquired tolerance to future arsenic exposure. The Applicant notes that for this naturally induced tolerance to be effective, there must be enough cysteine available for the cell to synthesize the requisite glutathione.

It has been determined that cells that are resistant to arsenic toxicity typically have an up-regulation of the genes involved in the production of the glutathione detoxification proteins (glutathone synthesis (TOXSCI70:183), glutathione reductase (TOXSCI70:183), glutithione transferases (TAP183:99, MOPM60:302), and the multidrug resistance transport proteins (MOPM60:302)).

Conversely, reducing the level of glutathione (e.g. via the administration of buthionine sulfoximine (BSO) or ascorbic acid) has been shown to increase the cytotoxicity of chemotherapeutic arsenicals (BLOOD93:268, BLOOD98:805, CCP52:47). FIG. 10 of CCP52:47 shows photographs of leukemia cell cultures that have received these treatments, dramatically showing the increase in the "kill rate" of arsenic trioxide when either BSO or ascorbic acid is co-administered.

Interestingly, it has been shown that when leukemic cells evolve to become resistant to the chemotherapeutic drug "TPA", their natural glutathione level decreases, making these cells especially sensitive to the arsenic trioxide. Thus, it can be beneficial to initially administer TPA to leukemia patients, with the plan of later administering arsenic trioxide to those patients whose leukemia becomes resistant to TPA (BLOOD97:3931).

7.2.3.1.2 Only Glutathione Conjugates of Arsenic are Excreted from Cells

The mechanisms involved in the excretion of the glutathione-arsenical conjugates from the cell has also been extensively studied within the context of multidrug resistant cancer cells. Regardless of whether the conjugate is formed non-enzymatically or it is formed by an enzyme (e.g. a glutathione transferase), the actual transport of the conjugate through the cellular membrane is performed by a trans-membrane multidrug-resistance protein (MRP) such as the MRP-1 or MRP2 pump (MOPM60:302, JBC275:33404). Chronic arsenic exposure up-regulates the expression of the genes for these proteins (MOPM60:302).

This excretion of arsenic from cells by an MRP been shown to require the arsenic to be complexed to glutathione, either in the form of ATG, or as MethylArsenic DiGlutathione (MADG), or as DiMethylArsenic Glutathione (DMAG) (JBC275:33404), because the depletion of glutathione in the cells reduces the excretion to less than 2% of the control rate (JBC275:33404). The MADG and DMAG excreted from liver cells into the bile has also been shown to rapidly break down to the MMA and DMA that are excreted from the body. Therefore, the formation of MADG inside the cell is critical for the excretion of arsenicals both from the cell and from the body. Because the rate for this depends on the 4th power of the GSH concentration (JBC275:33404), it can again be seen that glutathione depletion in cells drastically restricts their ability to excrete arsenic.

7.2.3.1.3 Detoxification of Arsenicals via Methylation Requires Glutathione

The methylation of arsenic to either MMA or DMA is the only significant path for the excretion of arsenic from the body. Newly ingested arsenic can be methylated and excreted very quickly, with typically 40% of it excreted directly from the liver to the bile during the first hour after consumption (JBC275:33404). But the remaining 60% enters the rest of the body and will take a significantly longer time to return to the liver (which is the only path to excretion).

The only significant dietary source for the methyl groups that are used for methylation reactions in humans is the amino acid methionine (Met). Typically, the methyl group from Met is first used to form SAM-e (S-adenosyl methionine), and then the methyl group is transferred by an appropriate enzyme from the SAM-e molecule to the methyl group recipient.

Methionine is a essential sulfur amino acid (SAA) and can be used to form cysteine if dietary cysteine is inadequate. Another way to look at this is that if Met is consumed by some metabolic process, less cysteine can be formed, thereby contributing to the development of cysteine (and glutathione) deficiency.

Two metabolic pathways have been found for the methylation of arsenic, and they both require glutathione. For cells that express the enzyme "arsenic methyltransferase Cyt19" the methylation step requires glutathione as a cofactor (ATOX79:183). There is also a non-enzymatic reaction that transfers a methyl group from methylated vitamin B12 (methylcobalamin) to arsenite, with glutathione as a cofactor (possibly via the intermediate formation of glutathionylcobalamin)(TAP154:287).

Methylated arsenic (e.g. MMA, DMA) is ~1000× less mutagenic than some inorganic arsenic compounds RA1231.A7N38:150). Therefore methylation is important not only for the excretion of arsenic from the body, but also to decrease the toxicity of the arsenic while it is within the body.

7.2.3.2 Correlation of Arsenicosis symptoms with Glutathione Depletion

The Applicant has observed that the other reported symptoms of chronic arsenic toxicity are similar to those that can result from biothiol deficiency.

Typically, the first visible symptom of arsenicosis is the darkening of the skin (hyperpigmentation) (JESH38A:141). Glutathione deficiency due to poor nutrition is a known cause of hyperpigmentation (ARCHIM138:356). Normal levels of glutathione in skin cells are needed for the feedback inhibition of melanin production. Without the feedback inhibition, the excess production of melanin produces skin darkening, including the formation of brown patches and black spots.

Hyperkeratosis (the thickening, hardening, and cracking of the skin) can be caused by the lack of normal skin loss. The dead stratum corneum cells that form the tough outer surface of the skin are supposed to be continuously shed and replaced with newly cornified cells. The extreme insolubility of the outer surface in vivo is a result of the macromolecular polymerization of various keratinocyte proteins involving both disulfids and isopeptide bonds (EMM31:5). The cleavage of both types of these bonds is necessary for normal skin loss. This can be shown in vitro, where the combined use of a detergent, a reducing agent (to separate the disulfide bonds via thiol-disulfide exchange reactions), and concentrated chaotropic agents (urea, guanindine-HCl) is necessary to solubilize the skin (EMM31:5).

The Applicant notes that a deficiency (or the excess oxidation) of the biothiols that are normally utilized in vivo for breaking these disulfide bonds would cause the thickening and the hardening of the skin, which could also lead to the cracking of the thickened, hardened skin.

Biothiols also inhibit the formation of advanced glycation end-products, another form of undesirable cross-links.

Blackfoot disease is related to poor peripheral circulation, as is the eventual development of gangrene. Endogenous nitric oxide (produced in vivo by the eNOS enzyme) is necessary for good blood flow. The feedback regulation of eNOS involves the nitrosylation (by nitric oxide) of a cysteine residue (in other words, this is an "SH" sensitive enzyme). The Applicant notes that this can be reversed by an exchange reaction with a thiol, returning the cysteine residue to its active state. Therefore, the activity of eNOS is determined by the balance between the NO concentration and the concentration of thiols in solution.

Garlic supplement consumption has been shown to increase the fluididty of blood, increasing the red blood cell velocity in the cutaneous capillaries by about 27% (PM56: 668). Dietary alliums increase the activity of eNOS (nitric oxide synthase), increasing the nitric oxide (NO) concentration and improving blood flow (BST23:S136). These effects are probably due to thiol supplementation.

7.2.3.3 Correlation of Arsenicosis with the Dietary Factors of Populations

There are also well-fed populations drinking arsenic contaminated water that do not develop arsenicosis (e.g. in many parts of the USA). The development of arsenicosis in arsenic exposed populations has been shown to correlate with poor nutrition (i.e. low body weight) (JESH38A:141, IJEP27:871) and the symptoms were shown to significantly improve after 7 weeks of treatment with a high protein diet and arsenic-free water (JESH38A:141).

Experiments with animal models confirmed the lower weight gain and increase in toxicity of arsenic when fed a low protein diet. Rabbits fed a low protein diet have decreased excretion (80%) and higher retention of arsenic (220% greater, in the liver) than arsenic fed controls (TL37:41). In another set of experiments (BDR71:124), arsenic exposed pregnant mice fed a low protein diet (5%) had significantly lower weight gain than controls fed a 20% protein diet (2.73 vs. 6.01), and had a significantly higher prenatal mortality (14% vs. 2.35%). Their offspring also had lower weight (0.72 vs. 0.93) and a much higher percentage of grossly malformed fetuses per liter (24.65% vs. 0.81%).

A detailed study of the relationship between nutritional factors and susceptibility to arsenic caused skin lesions in West Bengal, India (EHP112:1104) presents survey results that support the observation of the Applicant that there is a correlation between low dietary sulfur amino acid (SAA) intake (presumably resulting in glutathione deficiency) and toxicity of arsenic exposure.

Table 3 in the article compares the nutrient intake between the cases and the controls, which is used by the authors to identify the nutritional risk factors. Four of these were highlighted in the description of the results. The strongest factor that increased risk was found to be low animal protein intake (animal protein is the best source of SAA content). The Applicant notes that almost all Indian Foods that include meat also include garlic or onions (another good source of SAA and thiols).

The next strongest factor was low fiber intake. The authors note that a large fraction of the fiber intake in this population comes from rice intake. Rice has relatively high SAA content compared to other non-animal foods.

The risk from low calcium intake was comparable to that of low fiber intake. If a primary dietary source of calcium is from milk products, then low calcium intake implies low milk intake. In the average US diet, approximately ¾ of calcium comes from milk products. Because whole milk is a good dietary source for cysteine, high milk intake correlates with high dietary cysteine. However, if the reported calcium is from cabbage or broccoli, these are also good sources of SAA and thiols.

The fourth major risk factor was low vitamin C intake. Because vitamin C can partially substitute for glutathione and can protect animals from otherwise fatal glutathione loss (RB170.O96:101), this also indicates the possibility of the arsenicosis symptoms being due to glutathione deficiency. Although high dosages of vitamin C can be used to increase the toxicity of arsenic, the amount of dietary vitamin C (especially for poorly nourished people) is nowhere near the level that is used clinically to cause a decrease in glutathione (e.g. 1000 mg/day).

After adjustment for socioeconomic variables, low folate consumption also emerged as a significant risk factor (EHP112:1104, Table 5). The Applicant notes that a major biological function of folate is as a cofactor in the conversion of homocysteine back to cysteine (in effect, enabling the cysteine that metabolizes to homocysteine to complete the cycle) and the most prevalent toxicity from folate deficiency is the accumulation of homocysteine (and consequent depletion of cysteine) (CCHEM51:5).

A study of the risk factors associated with the development of arsenicosis from arsenic contaminated well water was also conducted in Taiwan, which determined that a diet with an egg consumption frequency of <1 a week had an odds ratio (OR, an indicator of higher relative risk) of 2.3 relative to those who consume 4 or more eggs, having sweet potato vs. rice as the staple food had an OR of 1.9, meat consumption <1 a week vs. 4 or more had an OR of 1.57, and consuming vegetables <7 days/week vs. every day had an OR of 1.43 (ARTSC8:452. The Applicant notes that rice has a cysteine content of 107 mg/100 g (cooked, but dry), while sweet potato has only 14 mg/100 g (QP141.N48:249) and that these risk factors are consistent with there being a correlation between low sulfur amino acid consumption and arsenic toxicity.

Another study investigated whether a well fed population that had been exposed to arsenic in water for centuries had developed a tolerance (EHP108:617). The Atacameno people in Northern Chile are a group that have been drinking arsenic contaminated water for thousands of years. The residents of a small village called Chiu Chiu are a well nourished group whose main economic activity is growing fruits and vegetables, especially carrots. Surprisingly, their prevalence of arsenicosis was found to be at least as great as that of other comparably exposed groups (e.g. in India or Taiwan). The authors of this report note that each of the families that were affected with arsenicosis consumed carrots every day (presumably because they were carrot farmers), but interpreted this as being part of their good nutrition. The Applicant notes that carotenoids are known (but apparently not well known) to damage thiols and therefore could be contributing to cysteine deficiency in these otherwise well nourished people, which could explain their heightened sensitivity to arsenic exposure relative to the other families in the village.

The Applicant notes that the naturally acquired tolerance (e.g. up regulation of detoxification enzymes) requires dietary cysteine to be effective, and in the absence of sufficient cysteine (or in the presence of thiol depletion, such as that produced by carotenoids) the "tolerance" could actually increase the toxicity of arsenic exposure.

7.2.3.4 Arsenicosis in Peripheral Tissues May be Due to Protection of the Internal Organs The Applicant has discovered that the amount of cysteine that is available for the peripheral tissues can be significantly lowered due to competition with the organs and tissues that are served first by the blood stream. The up-regulation of enzymes associated with chronic arsenic exposure increases the cellular uptake of cysteine for glutathione synthesis in the gut, liver, kidney, and presumably other organs and tissues that are well supplied with blood (e.g. the heart) which, especially in the case of deficiency, lowers the availability of cysteine in the rest of the body. This provides an explanation of why the toxicity of arsenicosis develops sooner and is most prevalent in peripheral tissues such as the skin, hands, and feet.

The digestive tract uses a mucous layer to protect its tissue from proteolytic enzymes, acidity, and toxic substances. The mucous contains glutathione as a protective substance. This glutathione has been found to bind to the consumed arsenic, depleting the glutathione in the process. In response, the de novo synthesis of glutathione in the mucosal cell becomes up-regulated, resulting in twice the normal concentration of glutathione within 3 hours (BBA628:241). The Applicant notes that although this is clearly beneficial to the digestive tract, and nominally to the animal as a whole (because it speeds-up the elimination of the arsenic), the cysteine that is utilized for this depletes the cysteine that is available for the rest of the body. This cysteine loss is probably insignificant for a well nourished person, but it becomes significant if the body is already cysteine deficient.

Further research has indicated that the up-regulated synthesis of glutathione within DiMethyl Arsenic acid (DMA) in cultured Chinese hamster V79 cell has the side effect of decreasing the rate of protein synthesis in these cells (to 70-80% of controls) due to competition for the available cysteine (ATOX71:730). The Applicant notes that this is another indication of how the increased production of glutathione decreases the amount of cysteine available for other functions and, in effect, increases the dietary requirement of cysteine for arsenic exposed populations.

Chronic exposure to arsenicals increased GST activity and glutathione levels in rat liver cells (TOXSCI91:70). Interestingly, the liver glutathione level of protein deficient rats has been shown to increase even more than for the well nourished rats (ENVTP8:227). The lever glutathione level in the well fed rats (18% protein in the diet) increased from 88 micrograms per gram to 123, while for the protein deficient (6%) rats it increased from 74 to 134, compared to the controls (which were not exposed to sodium arsenate). The effect on the kidney was less dramatic, but exposure to arsenic did increase the glutathione levels, and the increase was greater for the rats given the low protein diet. The Applicant notes that the increase in glutathione in these organs could contribute to glutathione depletion elsewhere in the body for poorly nourished people.

7.2.3.5 Clinical Trials in Bangladesh

The Applicant had the good fortune to meet Abdul Kader, a PhD student from Bangladesh, when attending the 2005 annual meeting of the International Union of Microbiological Societies. While in Bangladesh, and also later as a PhD student, Abdul had conducted research into the prevention and treatment of arsenicosis and had authored a report on the lack of commercially available technology that is suitable for the removal of arsenic from drinking water. Over the next few months, a plan was developed to conduct a limited-scale clinical trial of the effectiveness of the skin lotion for the treatment of arsenicosis. The goal was to demonstrate proof of feasibility sufficiently to convince a Non-Governmental Organization (NGO) to conduct (and fund) a more comprehensive clinical trial.

Because the costs of the trial would be paid for by the Applicant, a budget of $1000 a month was established and multiple phases with associated progress milestones were planned. The project was staffed accordingly with a full time coordinator (Mir Zakir Hassan) located at one of the villages (and traveling to the other villages frequently) and the part-time services of a medical doctor (Dr. Abdus Salam, located in Dhaka) who visits the villages periodically to monitor the patients and is available on-call as necessary. Additional part-time assistance is provided by Pulin Bahari Das (who operates a micro-credit NGO nearby and is well respected by the community). He set up an awareness program and conducted meetings with the local people.

To provide enough patients, three villages in the Hazigonj district under the Chandpur division in Bangladesh were selected. A questionnaire and informed consent document was used to survey each potential patient, with questions about their socioeconomic conditions, disease symptoms, the tenure of their disease, other associated problems, and which types of medications they use. The patients were taken randomly with the main criteria being that they have visible symptoms of arsenic induced problems on their body. The sex distribution of the selected patients is 19 male (32%) and 33 female (68%). The age distribution of the selected patients is as follows:

0-10 years: 1
11-20 years: 4
21-30 years: 18
31-40 years: 14
41-50 years: 6
51-60 years: 7
61-70 years: 1
71-80 years: 1

The patients varied widely based on their age and the level of disease progression. The duration of their visible symptoms ranged from three months to nine years. The most common symptoms reported are discoloration of the skin (hyperpigmentaion), roughness of skin, keratosis, skin cracks on the hands and legs, and in some cases ulceration or lesions with an associated discharge of fluid.

Initially, a skin lotion and a skin oil were tested for a duration of two months. The skin oil was manufactured using inexpensive raw ingredients, which would be more desirable than the relatively expensive base lotion from Neutrogena that was previously used for testing. This will become important if the project is successful and the manufacturing is eventually transferred to Bangladesh.

The skin lotion is similar to the Universal Antioxidant lotion, but stronger. It is based on Neutrogena Norwegian Body Emulsion with the added active ingredient of 1.25 ml of DADS per 310 ml of lotion (instead of the 0.3 ml of allyl mercaptan). The DADS does not smell as strongly as the allyl mercaptan, allowing a larger concentration to be used. DADS is classified as Generally Recognized As Safe (GRAS) for human consumption by the FDA (as is allyl mercaptan).

The skin oil uses 473 ml of mineral oil with 25 ml of glycerin (for thickening), 1.5 ml of geranium oil (for a pleasant scent), and 2.5 ml of DADS (the active ingredient). Note that the mineral oil has twice the concentration of the active ingredient relative to the lotion, which was possible because the mineral oil was found to do a better job of binding the DADS than the lotion does.

Fifteen patients were provided with the skin lotion (six male and nine female), ranging in age from 5 to 75 years old. The reported duration of symptoms ranged from 1 year to 8 years, primarily skin roughness, hyperpigmentation, and keratoses, but there are also patients with skin ulcers and fungal infection. The patients were trained how to use the lotion and their progress was frequently monitored in the field and occasionally monitored by the visiting doctor.

Two patients were not regular in using the lotion. There were also 2 patients who did not benefit from the use of the lotion. Of the remaining patients, the most significant effect was a reduction of skin roughness (reported by the doctor as ranging from 60-85%), followed by a decrease in black spot intensity ranging from 30-85%. The most dramatic recovery was that of the 5 year old child who had been suffering for 1 year, but now is completely cured. The skin ulcers are reported as being substantially improved.

Sixteen patients were provided with the skin oil (six male and ten female), one of which discontinued treatment. The most dramatic improvement was that of the five patients who had skin ulcers and got a recovery of 50-80%. Of the eight patients that were suffering from skin roughness, one improved 20% and the remaining seven improved from 40-70%. Of the seven patients with visible black spots, two showed an improvement of 10-15% and the remainder showed an improvement from 40-55%. Two of the patients had previously reported a general feeling of pain which they attributed to arsenicosis and after only 4 weeks of treatment they reported a 30% reduction in the pain.

At the end of this phase, the impression of the field staff and the doctor was that the skin oil performed better than the skin lotion. This was attributed to its improved ability to penetrate deep cracks (for those patients with deep cracks in their skin) while performing as well as the lotion for the other patients. However, the improved performance could also be due to the increased concentration of the active ingredient.

For the next phase, a mineral oil was prepared that was similar to the previous skin oil and included the inactive ingredients (glycerin and geranium oil) but no active ingredient. The intent was to have this serve as a "control" experiment. An additional formulation was developed using "Triple Lanolin Aloe Vera" from Vienna Beauty Products, Daton, Ohio, as the base lotion (to which we assigned the shorthand term "ointment", to distinguish it from the previous lotion). The price of this lotion is less than half the price of the Neutrogena one, and it is available by the gallon. Initial testing by the Applicant showed that 2.5 ml of DADS can be used with each 473 ml of the ointment, resulting in the same concentration of the active ingredient as the skin oil that was tested in the first phase.

Seven patients used the mineral oil for two months with no significant changes in their condition. This indicates that the active ingredient (DADS) is producing the benefits that are seen with the formulations that include it.

Twenty-one patients were provided with the ointment (seven male and fourteen female). One patient discontinued its use. Unfortunately, the second shipment of the ointment was lost in the mail and therefore there was only enough ointment available in the field for one month of testing. The general impression of the field staff and the doctor was that the rate of improvement with the ointment was at least as fast as that which was observed with the skin lotion and the skin oil. Most of the patients with skin roughness had an improvement of 40-65% and most of the patients with black spots had an improvement of 30-40%. All of the patients with skin ulcers had substantial improvement.

In summary, so far the trial has shown that the active ingredient produces a significant reduction in the symptoms of arsenicosis. The doctor notes that for each class of symptom, the patients who have been suffering for the shorter period exhibited the most improvement. Although the best solution to the problem is the replacement of the source of drinking water (e.g. by drilling deep wells), the skin lotion, oil, and ointment formulation can be used to provide immediate relief to the affected population. The results are considered sufficiently positive that additional clinical trials should be conducted (preferably by a Non-Governmental Organization) using these (or similar) formulations.

9. USE OF OTHER *ALLIUM* RELATED ORGANOSULFUR COMPOUNDS

The present invention has been illustrated according to the use of the model compounds allyl mercaptan, diallyl disulfide and SAMC to produce allyl mercaptan in vivo with subsequent conversion to other organosulfur compounds when oxidized, including the thiosulfinate allicin. But other membrane permeable organosulfur compounds incorporating other types of mercapto radicals have also been shown to have similar beneficial properties.

For example, the organosulfur compounds from onion tend to contain propyls instead of allyls. Just as the compound diallyl disulfide can be oxygenated to allicin, the onion derived compounds di-n-proply disulfide and n-propyl allyl disulfide can be oxygenated to their corresponding thiosulfinates, which may explain their antibiotic effectiveness against *Salmonella typhimurium* and *E. coli* (AM17:903). Similarly, the organosulfur compounds derived from cabbage tend to contain methyl groups, with methyl methanethiosulfinate (MMTSO) showing remarkable antimicrobial properties (JFP60:67).

A survey of the nematicidal activity of various sulfur compounds from *Allium* grayi Regel and *Allium* fistulosum L. var. *caespiitosum* concluded that those which have a disulfide, trisulfide, thiosulfinate, or thiosulfonate group are potential nematicides and antimicrobials (ABC52:2383). The most effective compound found was dipropylthiosulfinate $CH_3CH_2CH_2S—S(O)CH_2CH_2CH_3$.

In general, it is expected that membrane permeable mercapto radicals containing up to 5 carbon atoms will share many of the properties that are attributed to allyl mercaptan, diallyl disulfide, and SAMC in this description. Therefore, these constitute alternative substances that may be utilized according to the teachings of this patent application. (Studies of radioprotective substances have shown that thiol compounds with more than 5 carbon atoms are ineffective in protecting animals from radiation exposure. The Applicant notes that thiols that are larger than this are likely to eventually form mixed disulfides with glutathione which can be expected to be excreted from cells by the GS-X pump.)

The requirement of the present invention for the *allium* related compound to be able to metabolize into membrane permeable thiol, disulfide (or mixed disulfide), and thiosulfinate (or mixed thiosulfinate) compounds can be satisfied by a variety of organosulfur compounds in various compositions. Allyl mercaptan, diallyl disulfide and SAMC have the advantage that they are known derivatives of garlic, a vegetable that has been successfully consumed by billions of people over thousands of years. And the metabolites from garlic (such as allicin) have been extensively investigated by researchers. However, the present invention is intended to also apply to the more general class of compounds that have been presented in this section.

10. POTENTIALLY RESTRICTIVE PRIOR ART

The potentially restrictive prior art can be evaluated from two perspectives. Prior art involving the personal care or medicinal application of compounds with similar molecular structures (should such prior art exist) can be distinguished from the present invention by criteria such as the new personal care and medicinal applications of these compounds that are taught herein, the method of administration, and the dosage range. Conversely, prior art involving the use of unrelated compounds for similar personal care or medicinal applications can be distinguished from the novel compounds that are taught herein, their methods of administration, and their dosage ranges. In other words, the present invention involves both new ways to use old compounds, and new compounds to use for old applications, as can be seen from the following consideration of potentially restrictive prior art.

10.1 Methods for Removing the Smell of Alliums from Foodstuffs.

Some research has been published on techniques for removing the smell of *allium*-specific volatile sulfur compounds from foods (JAFC50:3856). The researchers concentrated on identifying foods that could "capture" the volatile compounds, and a wide variety of types of foods were tested, with prune, burdock, basil, eggplant, and mushroom being shown by gas chromatography to be able to capture 100% of the odorous compounds.

Further investigation of the mechanism of capture by phenolic compounds (e.g. those in mushrooms) indicated that the addition of thiols to phenolic compounds is catalyzed by enzymes present in raw foods (they term this "enzymatic deodorization"). They further determined that dislufides could be degraded by heating and propose that the degradation products could also be removed by performing an enzymatic addition reaction to o-quinone after heating. The third mechanism of capture that they describe is the affinity to molecules either due to hydrophobicity or by the trapping by porous polymers present in foods.

This prior art is not restrictive relative to the present invention because no attempt was made to preserve the medicinal properties of the volatile sulfur compounds, or to even establish the nutritional qualities of the resulting food products. The authors did not teach the desirability of preserving the integrity of the organosulfur groups while eliminating their volatility, e.g. via the bonding to significantly larger molecules (a method taught by the Applicant). The method that they teach (covalent bonding to phenols) does not produce a compound that would be expected to metabolize to membrane permeable thiols, disulfides, or mixed disulfides.

10.2 Prior Art Drugs
10.2.1 Radioprotective drugs

Various thiols and disulfides (along with various other chemical substances) have been studied for their radioprotective properties (RR2:392). Most sulfhydryl compounds tested were inactive, but the amino acids cysteine, homocysteine, cysteamine, and the peptide glutathione (along with their disulfides) have been found to be effective. Amino acids are not membrane permeable, so they do not constitute *allium* related compounds as defined herein.

The experimental use of even the best radioprotective drugs have shown that their effectiveness is limited to a protection of about 2 to 1 (e.g. the toxicity of radiation exposure is cut in half) and in order to achieve this level of protection a massive dose needs to have been administered within a few minutes before the radiation exposure. Thus, the prior art use of radioprotective compounds is not related to personal care as defined in this patent application.

Therefore, although these compounds relate in some ways to those utilized by the present invention, they constitute non-restrictive prior art when considering the teachings and claims presented herein.

10.2.2 Other Drugs that Metabolize to *allium* Related Compounds

There are other drugs that metabolize to thiols or disulfides. For example, the 1,3-thiazolidine ring system has attracted considerable interest over the years in relation to its occurrence as the initial structural unit in a variety of biologically and pharmacologically relevant compounds (BBA1073:416).

A characteristic feature of the 1,3-thiazolidine ring system is its facility to hydrolytic cleavage, resulting in an opening of the ring and exposing an SH group (BBA1073:416).

However, these compounds are not known to produce oxidation products that are membrane permeable and therefore are not relevant prior art.

Another example is provided by the analysis of the metabolism of the lipid-lowering drug probucol (a molecule that contains sulfur, but not in the form of a disulfide) (JLR-PAW30:1703). The authors propose that during the breakdown of spiroquinone to diphenoquinone (the author's proposed active ingredient in a free radical scavenger cycle) there is also produced (as a side effect, in the opinion of the authors) the disulfide $CH_3SSCH_3$. The Applicant notes that the authors do not ascribe any medicinal properties to disulfide $CH_3SSCH_3$ although they propose its existence.

The Applicant notes that if the disulfide $CH_3SSCH_3$ is produced, it would have the properties (including membrane permeability) of the *allium* related compounds that are taught in the present patent application. Therefore, this compound would fall within the present teachings, but the mere existence of this compound in nature, in the absence of the teachings or claims of others, does not constitute restrictive prior art.

It is not the intention of the Applicant to limit the use of any prior art drug for any prior art medicinal application. Therefore if, for example, the active metabolite of probucol was determined to be the disulfide $CH_3SSCH_3$ this would not, in and of itself, limit the future application of probucol for other known prior art applications of $CH_3SSCH_3$.

10.2.3 Allimax Creme

Allimax creme uses allicin as its active ingredient. As discussed above, allicin is a relatively reactive oxidant which could be damaging to skin if used in large quantities. Presumably, the concentration in this produce (5%) is low enough to avoid irritation. The half-life of allicin is normally relatively short (weeks to months), although the manufacturer claims to have developed a proprietary method to stabilize it.

However, allicin is neither a membrane permeable thiol nor a membrane permeable disulfide or mixed disulfide, therefore it is not restrictive prior art relative to the present invention.

10.2.4 Other Fungicidal Skin Ointments

Several fungicidal skin ointments (lotions, cremes, etc.) are available which contain anti-fungal agents such as calcipotriol, betamethasome dipropionate, salicylic acid (BJD39: 655), ketoconazole (AFP61:2703) or flurbiprofen (LAM37: 158). However, in each case the active ingredient is neither a membrane permeable thiol nor a membrane permeable disulfide or mixed disulfide, therefore they are not restrictive prior art relative to the present invention.

10.2.5 Other Antioxidant Skin Lotions Using Organosulfur Compounds

The U.S. Pat. No. 5,296,500 teaches and claims the use of N-acetyl-L-cysteine as a method for regulating wrinkles and/ or atrophy in mammalian skin. However, the active ingredient is neither a membrane permeable thiol nor a membrane permeable disulfide or mixed disulfide, therefore they are not restrictive prior art relative to the present invention.

10.2.6 Other Compositions for Oral Use that Incorporate Organosulfur Compounds

The U.S. Pat. No. 4,486,403 teaches and claims the use of the amino acid cysteine as a method to prevent the formation of dental carries (cavities).

The U.S. Pat. No. 5,906,811 teaches and claims the use of glutathione as an intra-oral-antioxidant.

However, in each case the active ingredient is neither a membrane permeable thiol nor a membrane permeable disulfide or mixed disulfide, therefore they are not restrictive prior art relative to the present invention.

What is claimed is:

1. A method of therapeutic treatment of a host suffering from a skin condition which can benefit from treatment with a membrane permeable antioxidant, said condition selected from the group consisting of:
   (a) sunburn,
   (b) dermatitis due to poison oak or poison ivy,
   (c) free radical damage, and
   (d) arsenicosis
   said method comprising topically applying to skin of said host a composition comprising a membrane permeable antioxidant and a dermatologically acceptable carrier suitable for topical application to the skin, wherein the membrane permeable antioxidant is a therapeutically effective amount of an allium related compound selected from the group consisting of allyl mercaptan, n-propylmercaptan, diallyl disulfide, di-n-propyl disulfide, n-propyl allyl disulfide and combinations thereof, and wherein the allium related compound is sufficiently bound to the carrier to be non-volatile, but said binding is readily broken upon application to the skin.

2. A method of therapeutic treatment of a host suffering from a skin condition which can benefit from treatment with a membrane permeable antioxidant, said condition selected from the group consisting of:
   (a) sunburn,
   (b) dermatitis due to poison oak or poison ivy,
   (c) free radical damage, and
   (d) arsenicosis
   said method comprising topically applying to skin of said host a composition comprising a membrane permeable antioxidant and a dermatologically acceptable carrier suitable for topical application to the skin, wherein the membrane permeable antioxidant is a therapeutically effective amount of an allium related compound selected from the group consisting of allyl mercaptan, n-propylmercaptan, diallyl disulfide, di-n-propyl disulfide, n-propyl allyl disulfide and combinations thereof, and wherein the allium related compound is the sole active ingredient in said composition that is effective for treating said condition selected from the group consisting of: (a) sunburn, (b) dermatitis due to poison oak or poison ivy, (c) free radical damage, and (d) arsenicosis. said binding is readily broken upon application to the skin.

3. The method of claim 1 or claim 2, wherein said treatment is for sunburn and said allium related compound and carrier are applied to the skin in a therapeutically effective amount for use as an anti-sunburn agent.

4. The method of claim 1 or claim 2, wherein said treatment is for dermatitis from poison oak or poison ivy and said allium related compound and carrier are applied to the skin in a therapeutically effective amount for use as an anti-poison-oak or anti-poison ivy agent.

5. The method of claim 1 or claim 2, wherein said treatment is for reducing free radical damage to the skin of the host and said allium related compound and carrier are applied to the skin in a therapeutically effective amount for use as an antioxidant agent.

6. The method of claim 1 or claim 2, wherein said treatment is for arsenicosis and said allium related compound and carrier are applied to the skin in a therapeutically effective amount for use as an anti-arsenicosis agent.

7. The method of claim 1 or claim 2, wherein said allium related compound is di-n-propyl disulfide.

8. The method of claim 3, wherein the composition consists essentially of a concentration of ⅓ ml of diallyl sulfide added to 31.0 ml of a suitable dermatologically acceptable carrier.

9. The method of claim 4, wherein the composition consists essentially of a concentration of ⅓ ml of diallyl sulfide added to 31.0 ml of a suitable dermatologically acceptable carrier.

10. The method of claim 1 or claim 2, wherein the allium related compound is derived from garlic oil.

11. The method of claim 1 or claim 2, wherein the allium related compound is derived from onion oil.

* * * * *